United States Patent [19]

Baschang et al.

[11] Patent Number: 4,711,879
[45] Date of Patent: * Dec. 8, 1987

[54] ACYLATED SUGAR DERIVATIVES, PROCESSES FOR THEIR MANUFACTURE, AND THEIR USE

[75] Inventors: Gerhard Baschang, Bettingen, Switzerland; Albert Hartmann, Grenzach, Fed. Rep. of Germany; Oskar Wacker, Basel, Switzerland

[73] Assignee: Ciba-Geigy Corporation, Ardsley, N.Y.

[*] Notice: The portion of the term of this patent subsequent to Feb. 3, 2004 has been disclaimed.

[21] Appl. No.: 928,493

[22] Filed: Nov. 7, 1986

Related U.S. Application Data

[63] Continuation of Ser. No. 739,269, May 29, 1985, Pat. No. 4,640,911.

[30] Foreign Application Priority Data

May 29, 1984 [CH] Switzerland ............ 2635/84

[51] Int. Cl.[4] ............ A61K 31/70; C08G 18/08
[52] U.S. Cl. ............ 514/42; 536/53
[58] Field of Search ............ 514/42; 536/53

[56] References Cited

U.S. PATENT DOCUMENTS

| | | | |
|---|---|---|---|
| 4,082,735 | 4/1978 | Jones et al. | 260/112.5 R |
| 4,082,736 | 4/1978 | Jones et al. | 260/112.5 R |
| 4,256,735 | 3/1981 | Durette et al. | 260/112.5 R |
| 4,314,998 | 2/1982 | Yamamuka et al. | 260/112.5 R |
| 4,315,913 | 2/1982 | Durette | 260/112.5 R |
| 4,368,190 | 1/1983 | Shen et al. | 260/112.5 R |
| 4,396,607 | 8/1983 | Lefrancier et al. | 260/112.5 R |
| 4,406,889 | 9/1983 | Hartmann et al. | 260/112.5 R |
| 4,640,911 | 2/1987 | Baschang et al. | 514/42 |

FOREIGN PATENT DOCUMENTS 014984 3/1980 European Pat. Off. .

OTHER PUBLICATIONS

M. Parant, et al., J. Infectious Diseases, 142:708–715, (1980).
Chem. Abstr. 99:98973m, (1983), p. 41.
Chem. Abstr. 92:191389r, (1980), p. 61.

Primary Examiner—Delbert R. Phillips
Attorney, Agent, or Firm—Michael W. Glynn; Irving M. Fishman

[57] ABSTRACT

There are described sugar derivatives of the formula I

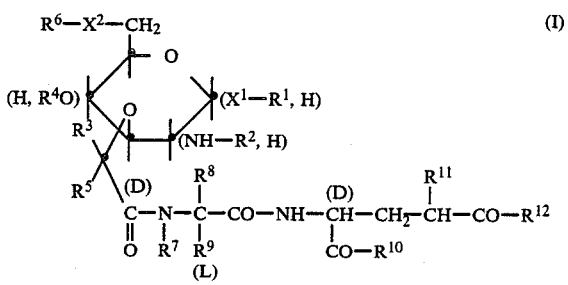

that have immuno-stimulating action and that contain as inventive element at least one radical $A^1$ or $A^2$. These radicals $A^1$ and $A^2$, which may be constituents of the radicals $R^1$, $R^2$, $R^4$, $R^6$, $R^9$, $R^{10}$ or $R^{12}$ according to formula I, are defined as follows:

$A^1$ represents lower alkanoyl that is substituted by aryl, heteroaryl or heteroarylthio and that may be additionally substituted by an ethylene radical which, with the above-mentioned aryl or heteroaryl substituent, forms a five-membered ring or represents ortho- or ortho/meta-substituted aroyl. $A^2$ represents lower alkoxy substituted by aryl, heteroaryl or heteroarylthio.

Also described are processes for the manufacture of the compounds of the formula I and novel intermediates.

25 Claims, No Drawings

ACYLATED SUGAR DERIVATIVES, PROCESSES FOR THEIR MANUFACTURE, AND THEIR USE

This is a continuation of application Ser. No. 739,269 filed on May 29, 1985, now U.S. Pat. No. 4,640,911.

The invention relates to sugar derivatives of the formula I

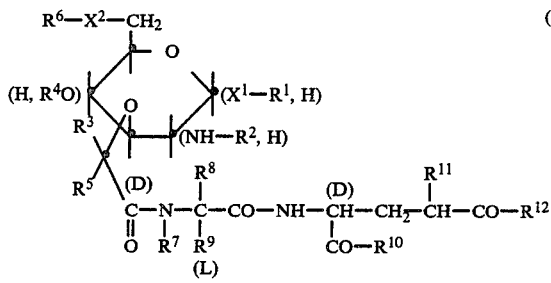

in which the sugar moiety is derived from D-glucose, D-mannose or D-galactose, $X^1$ represents oxygen, sulphur or the group NH, $X^2$ represents oxygen or the group NH, $R^1$, $R^4$ and $R^6$ each represents, independently of the others, hydrogen, lower alkanoyl, a radical of the formula Ia,

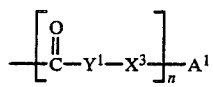

in which n represents 0 or 1, $Y^1$ represents unsubstituted or substituted alkylene which may be interrupted by carbonylimino or carbonyloxy, $X^3$ represents oxygen or the group NH and $A^1$ represents lower alkanoyl that is substituted by aryl, heteroaryl or heteroarylthio and that may be additionally substituted by an ethylene radical which, with the above-mentioned aryl or heteroaryl substituent, forms a five-membered ring, or represents ortho- or ortho/meta-substituted aroyl, or $R^1$, $R^4$ and $R^6$ each represents, independently of the others, a radical of the formula Ib

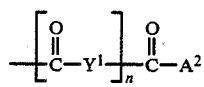

in which n and $Y^1$ have the meanings mentioned above and $A^2$ represents lower alkoxy substituted by aryl, heteroaryl or heteroarylthio, or $R^1$ alternatively represents unsubstituted or substituted benzyl, $R^2$ represents unsubstituted or hydroxy-substituted lower alkanoyl, unsubstituted or substituted benzoyl or one of the above-mentioned radicals of the formulae Ia and Ib, $R^3$ represents hydrogen, lower alkyl or cycloalkyl and $R^5$ represents hydrogen, or $R^3$ and $R^5$ together represent lower alkylidene, cycloalkylidene, unsubstituted or substituted benzylidene, $R^7$ represents hydrogen or lower alkyl, or $R^7$ and $R^9$ together represent trimethylene, $R^8$ represents hydrogen or lower alkyl, $R^9$ represents hydrogen or lower alkyl that is unsubstituted or substituted by hydroxy, mercapto, lower alkylthio, carboxy, lower alkoxycarbonyl, carbamoyl or by a radical of the formula Ic, Id, Ie or If

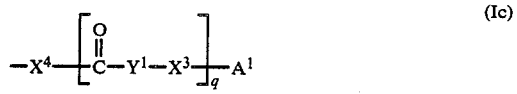

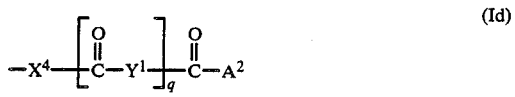

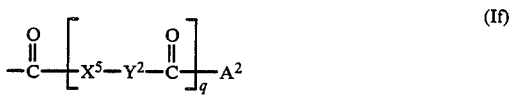

in which q represents 0 or 1, $X^4$ represents oxygen or sulphur and $X^5$ and $X^6$ each represents, independently of the other, oxygen or the group NH, and the other substituents have the meanings mentioned above, $R^{10}$ and $R^{12}$ each represents, independently of the other, lower alkoxy, hydroxy, amino, lower alkylamino that is substituted by carboxy, carbamoyl or by lower alkoxycarbonyl and that may be additionally substituted by amino, hydroxy, carboxy, 2-aminoethylthio, 2-aminoethoxy and/or by the sulpho group —$SO_3H$, a radical of the formula Ig,

in which $Y^2$ represents unsubstituted or substituted alkylene in which a methylene group may have been replaced by oxygen, sulphur or sulphinyl and which may be interrupted by carbonylimino or carbonyloxy, and in which $X^5$, $X^6$ and $A^1$ have the meanings mentioned above, or a radical of the formula Ih,

in which q, $X^5$, $Y^2$ and $A^2$ have the meanings mentioned above, and $R^{11}$ represents hydrogen, carboxy, lower alkoxycarbonyl or carbamoyl, the compounds of the formula I having a minimum of one and a maximum of three radicals $A^1$ and/or $A^2$, and to salts of such compounds having at least one saltforming group, to processes for the manufacture of ing these compounds, and to the use of these compounds in a method for the therapeutic treatment of the human or animal body or for the manufacture of pharmaceutical preparations.

In the formula I, the substituents —NH—$R^2$ and —$OR^4$ are in the α- or β-configuration and assume the positions of the corresponding hydroxy groups of D-glucose, D-mannose or D-galactose.

The sugar derivatives of the formula I may be in the form of isomeric mixtures or pure isomers. The substituent $X^1$—$R^1$ is in the α- and/or β-configuration(s). The configuration at the atoms C—$R^3$, C—$R^9$ and C—CO—$R^{10}$ is, in the case of asymmetrical substitution, (D), (L) and (D), respectively, as shown in formula I.

Lower alkanoyl $R^1$, $R^4$ and $R^6$ is preferably acetyl.

Alkylene is a bivalent, saturated hydrocarbon radical, preferably has up to and including 18, especially up to and including 12, more especially up to and including 10, and very especially up to and including 7, carbon atoms and is straight-chained or branched, the two bonds originating from the same carbon atom or from any two different carbon atoms, preferably the two terminal carbon atoms of the chain. The term therefore also includes alkylidene radicals, the two free valencies of which must originate from the same carbon atom. Alkylene is, for example, lower alkylidene, such as ethylidene, propylidene or 2-methylpropylidene, or mono- or oligo-methylene, for example methylene, dimethylene, trimethylene, tetramethylene, pentamethylene or hexamethylene.

Substituted alkylene contains, especially, free or esterified carboxy, for example benzyloxycarbonyl or lower alkoxycarbonyl, amino, lower alkanoylamino, hydroxy and/or lower alkanoyloxy as substituent(s).

Carbonylimino preferably represents the group —CO—NH—, but also the group —NH—CO—.

Carbonyloxy preferably represents the group —CO—O—, but also the group —O—CO—.

As examples of substituted alkylene $Y^1$ there may be mentioned: 2-carboxyethylidene or 2-methylpropylidene. As examples of substituted alkylene $Y^2$ there may be mentioned: 1-carboxy-di-, -tetra- or -pentamethylene or 2-hydroxytrimethylene. As examples of optionally substituted alkylene $Y^2$ in which a methylene group may have been replaced by oxygen, sulphur or sulphinyl and which may be interrupted by carbonylimino or carbonyloxy there may be mentioned: 1-carboxy-3-oxapentamethylene

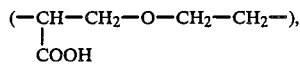

1-benzyloxycarbonyl-3-thiapentamethylene, 4-(ethylidenecarbonyl-imino)-n-butyl [—CH(CH₃)—CONH—(CH₂)₄—], 3-(ethylidenecarbonylimino)-2-hydroxypropyl, 2-acetoxy-3-(ethylidene-carbonylimino)-propyl, 3-[(4-aminopentylidene)-carbonylimino]-2-hydroxypropyl or 1-benzyloxycarbonyl-2-(ethylene-1-sulphinyl)-dimethylene

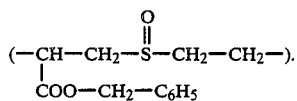

In accordance with the above definitions, alkylene interrupted by carbonylimino represents, for example, the radical —CH(CH₃)—CO—NH—(CH₂)₄—.

Aryl is especially substituted phenyl or naphthyl, there being mentioned as substituent of the phenyl radical especially the following: lower alkyl, especially 2-methylpropyl which is preferably in the para-position, substituted lower alkyl, for example hydroxybenzyl in the meta-position, halogen, for example chlorine or fluorine, hydroxy, lower alkoxy, such as, especially, methoxy, cycloalkyl, such as, especially, cyclohexyl, phenyl, heterocyclyl, such as, especially, 1-oxo-2-isoindolinyl or 2,5-dihydro-1H-pyrrol-1-yl, unsubstituted or substituted amino, such as, especially, unsubstituted or substituted phenylamino, for example 2,6-dichlorophenylamino, 2,6-dichloro-4-fluorophenylamino or 2,3-dimethylphenylamino, and/or aromatic acyl, such as, especially, benzoyl. Optionally substituted naphthyl is especially 6-methoxynaphth-2-yl.

Heteroaryl is especially unsubstituted or, preferably, substituted heterocyclyl that is unsaturated to a maximum extent and has 6 or preferably 5 ring members and from 1 to 4, preferably 1 or 2, hetero atoms, such as, preferably, nitrogen, oxygen and/or sulphur; in the case of a five-membered heterocycle having 2 hetero atoms, the hetero atoms are preferably in the 1,3-position with respect to one another. Heteroaryl is also above-mentioned heterocyclyl having 5 or 6 ring members that contains one or two fused-on and optionally substituted phenyl radicals, for example carbazol2-yl, especially 6-chlorocarbazol-2-yl, or indol-3-yl, especially 1-(4-chlorobenzoyl)-5-methoxy-2-methylindol3-yl or 1-benzoyl-5-methoxy-2-methylindol-3-yl.

Heteroaryl is also above-mentioned heterocyclyl having 5 or 6 ring members that contains, in addition to a fused-on phenyl radical, a fused-on pyridine radical, for example 5H-[1]benzopyrano[2,3-b]pyridin-7-yl.

Heteroaryl having one hetero atom is preferably, for example, pyrrolyl which may be substituted, for example, by lower alkyl, such as methyl, and/or by aromatic acyl, for example benzoyl or 4-methylbenzoyl, for example 1-methyl-5-(4-methylbenzoyl)-pyrrol-2-yl.

As preferred heteroaryl radicals having two hetero atoms there may be mentioned unsubstituted or, preferably, substituted 1,3-oxazol-2-yl, 1,3-diazol-2-yl or 1,3-thiazol-2-yl. Substituents of the above-mentioned heteroaryl radicals are preferably phenyl radicals that are unsubstituted or substituted, for example by methoxy, such as, for example, 4-methoxyphenyl, a heteroaryl radical preferably being substituted by two such phenyl radicals which are preferably in the ortho position with respect to one another. Substituted heteroaryl is thus, for example, 4,5-di-(4-methoxyphenyl)-1,3-oxazol-2-yl, -diazol-2-yl or -thiazol-2-yl.

Heteroarylthio has the above-mentioned heteroaryl radicals and is, for example, 1,3-oxazole-2-thio, 1,3-diazole-2-thio or 1,3-thiazole-2-thio substituted as described above, for example 4,5-di-(4-methoxy- phenyl)-1,3-thiazole-2-thio.

Substituted lower alkanoyl $A^1$ is preferably substituted acetyl, propionyl or 2-methylpropionyl, and the substituents are preferably in the 2-position.

The ethylene radical as an additional substituent of a lower alkanoyl radical $A^1$ is also preferably in the 2-position.

Lower alkanoyl $A^1$ that is additionally substituted by an ethylene radical which, with the aryl substituent, such as, for example, a phenyl substituent, forms a five-membered ring, is preferably hydrindene-1carbonyl (indan-1-carbonyl), for example 5-cyclohexyl-6-chlorohydrindene-1-carbonyl.

Lower alkanoyl $A^1$ that is additionally substituted by an ethylene radical which, with the heteroaryl substituent, such as, for example, a pyrrole, furan or thiophene substituent, forms a five-membered ring, is, for example, 3H-1,2-dihydropyrrolo[a]pyrrole-1-carbonyl, for example (d,l)-5-benzoyl-3H-1,2-dihydropyrrolo[a]pyrrole-1-carbonyl of the formula Iaα.

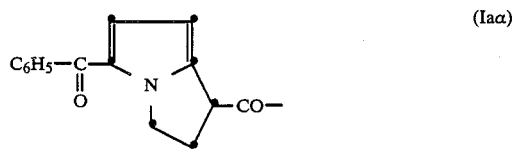

Ortho-substituted aroyl $A^1$ is preferably benzoyl ortho-substituted by an unsubstituted or, preferably, substituted amino group, the amino group preferably being substituted by a phenyl radical, for example a phenyl radical carrying a lower alkyl substituent, such as, especially, a methyl substituent. Orthosubstituted aroyl is thus, for example, 2-(2,3-dimethylphenyl)-aminobenzoyl. Ortho/meta-substituted aroyl $A^1$ is preferably benzoyl that is substituted in the ortho position, preferably the 2-position, by hydroxy and in the meta position, preferably the 5-position, by unsubstituted or substituted, preferably halo-substituted, for example fluoro-substituted, phenyl. Ortho/meta-substituted aroyl is thus, for example, 5-(2,4-difluorophenyl)-2-hydroxybenzoyl.

Substituted lower alkoxy $A^2$ is preferably substituted ethoxy, especially 2-substituted ethoxy, substituted propoxy, especially 3-substituted propoxy, or substituted 2-methylpropoxy, especially 2-substituted 2-methylpropoxy.

Substituted benzyl $R^1$ is especially benzyl that is substituted in the phenyl moiety by lower alkyl, hydroxy, lower alkoxy or halogen.

Lower alkanoyl $R^2$ is preferably acetyl or propionyl. Hydroxy-substituted lower alkanoyl $R^2$ preferably carries the hydroxy group in the 2-position and is especially glycolyl.

Substituted benzoyl $R^2$ carries especially lower alkyl, lower alkoxy, halogen, lower alkanoyloxy and/or lower alkanoylamino as substituent(s) of the phenyl moiety.

$R^2$ is preferably unsubstituted benzoyl.

Lower alkyl $R^3$ is preferably $C_{1-3}$-alkyl, especially methyl, ethyl or n-propyl. Lower alkylidene $R^3 + R^5$ is preferably unsubstituted or $C_{1-3}$-alkyl-substituted methylene, for example methylene, ethylidene, n-propylidene or n-butylidene, or optionally substituted benzylidene, for example benzylidene that is halogenated or substituted by lower alkyl in the phenyl radical, such as 4-chlorobenzylidene or 4-methylbenzylidene.

Cycloalkylidene $R^3 + R^5$ is preferably cyclopentylidene or cyclohexylidene.

Lower alkyl $R^7$ is preferably $C_{1-3}$-alkyl, especially methyl.

Lower alkyl $R^9$ is preferably methyl, ethyl, isopropyl, 2-methylpropyl or sec.-butyl.

Lower alkyl $R^9$ substituted by hydroxy, mercapto, lower alkylthio, carboxy or carbamoyl is preferably correspondingly substituted $C_{1-2}$-alkyl, for example hydroxymethyl, 1-hydroxyethyl, mercaptomethyl, 2-methylthioethyl, carboxymethyl, 2-carboxyethyl, carbamoylmethyl or 2-carbamoylethyl.

Lower alkoxycarbonyl $R^{11}$ is preferably ($C_{1-4}$-alkoxy)-carbonyl, for example methoxycarbonyl, ethoxycarbonyl or n-butoxycarbonyl.

Lower alkoxy $R^{10}$ or $R^{12}$ is preferably $C_{1-4}$-alkoxy, for example methoxy, ethoxy or n-butoxy.

Lower alkylamino $R^{10}$ or $R^{12}$ that is substituted by carboxy, carbamoyl or lower alkoxycarbonyl and that may be additionally substituted by amino, hydroxy, carboxy, 2-aminoethylthio, 2-aminoethoxy and/or by the sulpho group —$SO_3H$, is preferably substituted by carboxy, carbamoyl or lower alkoxycarbonyl in the 1-position and is, for example, the following, substituted in the 1-position in the above manner: ethylamino, n-propylamino, 2-methylpropylamino, 3-methylbutylamino, 2-methylbutylamino, 5-aminopentylamino, 4-aminobutylamino, 2-hydroxyethylamino, 2-carboxyethylamino, 2-carboxypropylamino, 6-amino-6-carboxyethylamino, 2-(2-aminoethylthio)-ethylamino, 2-(2-aminoethoxy)-ethylamino or 2-sulphoethylamino, the abovementioned substituted lower alkylamino radicals $R^{10}$ or $R^{12}$ that are derived from alanine, α-aminobutyric acid, valine, leucine, isoleucine, lysine, thialysine and oxalysine preferably having the (L)-configuration.

Alkylene $Y^2$ in which a methylene group has been replaced by oxygen or sulphur is preferably 3-oxapentamethylene or 3-thiapentamethylene.

Salt-forming groups in a compound of the formula I are acidic groups, for example free carboxy or sulphonic acid groups, or basic groups, such as, especially, free amino groups. Depending on the type of salt-forming group, the compounds of the formula I form metal or ammonium salts or acid addition salts. Salts of a compound of the formula I are preferably pharmaceutically acceptable and non-toxic, for example alkali metal or alkaline earth metal salts, for example sodium, potassium, magnesium or calcium salts, or salts with ammonia or suitable organic amines-aliphatic, cycloaliphatic, cycloaliphatic-aliphatic or araliphatic primary, secondary or tertiary mono-, di- or polyamines and also heterocyclic bases being especially suitable for the salt formation-such as lower alkylamines, for example triethylamine, hydroxy-lower alkylamines, for example 2-hydroxyethylamine, bis-(2-hydroxyethyl)-amine, 2-hydroxyethyldiethylamine or tri(2-hydroxyethyl)-amine, basic aliphatic esters of carboxylic acids, for example 4-aminobenzoic acid 2-diethylaminoethyl ester, lower alkyleneamines, for example 1-ethylpiperidine, cycloalkylamines, for example dicyclohexylamine, or benzylamines, for example N,N'-dibenzylethylenediamine, and also bases of the pyridine type, for example pyridine, collidine or quinoline. Compounds of the formula I having at least one basic group can form acid addition salts, for example with inorganic acids, such as hydrochloric acid, sulphuric acid or phosphoric acid, or with suitable organic carboxylic or sulphonic acids, for example trifluoroacetic acid, and with amino acids, such as arginine and lysine. If several acidic or basic groups are present, mono- or poly-salts can be formed. Compounds of the formula I having an acidic group, for example a free carboxy group, and a free basic group, for example an amino group, may also be in the form of internal salts, that is to say in zwitterionic form, or one part of the molecule may be in the form of an internal salt and another part may be in the form of a normal salt.

For isolation or purification it is also possible to use pharmaceutically unacceptable salts. However, only the pharmaceutically acceptable non-toxic salts are used therapeutically and these are therefore preferred.

The aim of the present invention is to provide novel pharmacologically active compounds having a novel action profile with respect to the totality of their pharmacological actions.

The compounds of the formula I have valuable pharmacological properties, especially a pronounced immuno-modulating, especially immuno-stimulating, action.

In vivo, the compounds of the formula I also increase manifestations of cell-mediated immunity, as is shown, for example, in the following test in which the increase in the delayed type hypersensitivity to bovine serum albumin (BSA) is determined in guinea pigs:

On day 0, Pirbright guinea pigs are immunised with 1 mg of BSA and various amounts of a compound of the formula I in incomplete Freund's adjuvant by injecting 0.1 ml of this antigen/adjuvant mixture into each of the hind paws. Three weeks later skin reactions are induced by the intracutaneous injection of 100 μg of BSA in 0.1 ml of buffered physiological sodium chloride solution (PBS) into the depilated flank of each animal and quantified on the basis of the reaction volume which is calculated 24-48 hours later with reference to the surface area of erythema and the increase in skin thickness. After 24-48 hours (delayed type reaction) a significant antigen-specific increase in the reaction volume is observed which is a measure of cell-mediated immunity The $ED_{50}$ values for the compounds of the formula I are, in the above-mentioned test, in the range of from 1 to 300 ug/animal.

The compounds of the formula I also increase mitogenity, as is shown, for example, in the following test:

Suspensions of highly enriched B-lymphocytes (splenocytes of congenitally athymic nu/nu mice) are incubated in the presence of a compound of the formula I for 3 days in 0.2 ml cultures in a $CO_2$ incubator. The incorporation of $^3H$-thymidine into the lymphocytes during the last 18 hours of the culture period is taken as a measure of the proliferation activity. It is found that compounds of the formula I are mitogenic with respect to B-lymphocytes in doses as low as 200 nanogram/ml.

The compounds of the formula I also have antitumour properties. These are based on their ability, for example incorporated in multilamellar liposomes or in phosphate-buffered physiological sodium chloride solution (PBS), to activate macrophages in such a manner that these endogenous defence cells are capable of killing tumour cells (cytotoxicity) or of hindering their growth (cytostasis). The inducement of tumoricidal and tumoristatic alveolar macrophages in rats in vitro and in situ can be demonstrated, for example, in the following test:

Alveolar macrophages are obtained by washing the lungs with culture medium. These macrophages are activated either by injecting the test substances into the rats (intravenously or intranasally, in situ activation) or by a 24-hour preliminary incubation with a compound of the formula I in a $CO_2$ incubator (in vitro activation). The macrophages activated in this manner are then incubated for a further 72 hours with tumour cells.

In order to measure tumoricidal activities of the macrophages, the tumour cells are labelled with $^{125}I$-iododeoxyuridine before the 72-hour incubation. The number of tumour cells that have not been killed can be measured, after washing away the radioactivity released by lysed tumour cells, on the basis of the radioactivity that remains.

In order to ascertain tumoristatic activities of the macrophages, $^3H$-thymidine is added to the cultures 8 hours before the end of the 72-hour incubation period, and afterwards the $^3H$-thymidine incorporation into the tumour cells is measured. In vitro, the substances, both when dissolved in PBS and when incorporated in liposomes, are able to induce tumoricidal alveolar macrophages in rats in doses as low as 20 nanogram/0.2 ml culture. In rats, a single intravenous administration of the compounds incorporated in liposomes at a dose of 160 μg/animal causes the inducement of tumoricidal and tumoristatic alveolar macrophages. In addition, a single intranasal administration of the substances in PBS at a dose of 25 μg/rat causes the inducement of tumoristatic alveolar macrophages.

In comparison with known muramyl peptides, the compounds of the formula I have greatly reduced undesired side effects and they are especially much less pyrogenic. This finding is of great importance since the administration of a pyrogenic substance may possibly cause thermal shock which is why safe use is ensured only under constant medical supervision, and certain forms of administration, such as intravenous administration, are out of the question.

The test for pyrogenity can be carried out in rabbits in accordance with the instructions given in the European Pharmacopoeia, Volume 2, pages 56 to 59 (1971). According to this test, for example N-propionyl- desmethylmuramyl-L-alanyl-D-isoglutaminyl-L-alanine-3-{2-[2-(2,6-dichlorophenylamino)-phenyl]-acetylamino}-2-hydroxypropylamide is not pyrogenic at a dose of 5 mg/kg i.v.

The compounds of the formula I can therefore be used especially as immunostimulants in warm-blooded animals, including human beings, for example as adjuvants in the development of novel inoculants or in the improvement of conventional inoculants and for the treatment of tumour diseases.

Those compounds of the formula I in which $R^1$, $R^4$ and $R^6$ represent lower alkanoyl, for example 1,4,6-tri-O-acetyl-N-propionyldesmethylmuramyl-L-alanyl-D-isoglutaminyl-L-alanine-{2-acetoxy-3-[d-2-(6-methoxy- naphth-2-yl)-propionylamino]-propyl}-amide, or in which $R^1$ represents optionally substituted benzyl, are surprisingly also outstandingly suitable for the prophylaxis and treatment of virus infections, as is apparent from tests on animals.

In these animal tests, animals, such as mice or guinea pigs, are infected with the most varied types of viruses at a dose that is lethal to all or the great majority of the untreated (control) animals, for example $LD_{80-90}$, and the course of the infection is observed in the untreated control animals in comparison with animals treated with one of the above-mentioned compounds or a salt thereof before, simultaneously with or after infection.

It is found that a prophylactic effect is achieved even when the compounds of the formula I in which $R^1$, $R^4$ and $R^6$ represent lower alkanoyl or $R^1$ represents optionally substituted benzyl, are administered several days up to some weeks, for example four weeks, before infection, and that a therapeutic effect is still achieved when the compounds are administered several days, for example one week, after infection.

These compounds of the formula I are effective in as low a dosage range as from 0.0001 mg/kg to 0.1 mg/kg in the above-mentioned test in mice.

Also noteworthy is the broad viral spectrum against which the above-mentioned compounds are effective.

The compounds of the formula I in which $R^1$, $R^4$ and $R^6$ represent lower alkanoyl or $R^1$ represents optionally substituted benzyl, can be used especially for the prophylaxis and treatment of diseases caused by the viruses specified below [for nomenclature see J. L. Melnick, Prog. med. Virol. 26, 214-232 (1980) and 28, 208-221 (1982)]:

DNA viruses with cubic symmetry and naked nucleocapsid, DNA viruses with encapsulated virion and RNA viruses with cubic symmetry and those with helical symmetry of the capsid.

These compounds of the formula I are preferably used in the case of DNA viruses with encapsulated virion and cubic symmetry of the capsid, in the case of RNA viruses with cubic symmetry of the capsid and naked virion and in the case of RNA viruses with helical symmetry of the capsid, in which the nucleocapsid capsule is positioned at the surface membrane, but also in the case of adenoviridae, poxviridae and coronaviridae, such as, especially, human corona viruses.

These compounds of the formula I are used especially in the case of herpesviridae, picornaviridae and myxo viruses, but also in the case of mastadeno viruses, such as, especially, human adeno viruses, in the case of chordopoxvirinae, such as, chiefly, orthopox viruses, such as, especially, for example, vaccinia viruses, in the case of reoviridae, above all (especially human) rota viruses, and in the case of caliciviridae and rhabdoviridae, such as, especially, vesiculo viruses in humans and also in horses, cattle and pigs.

These compounds of the formula I are used chiefly in the case of alpha-herpesvirinae, such as varicella viruses, for example human varicella-zoster viruses, rhino viruses, cardio viruses and ortho-myxoviridae, but also in the case of beta-herpesvirinae, such as, especially, human cytomegalo viruses, in the case of aphtho viruses, especially aphtho viruses in animals with cloven hooves, such as, especially, cattle, and in the case of para-myxoviridae, such as, especially, pneumo viruses, for example respiratory syncytial viruses in humans, and such as, also, morbilli viruses or para-myxo viruses, such as para-influenza viruses, for example human parainfluenza viruses, including Sendai viruses, and in the case of arbo viruses or vesiculo viruses, for example *Vesicular stomatitis* viruses.

These compounds of the formula I are used very especially in the case of simplex viruses, for example human Herpes simplex viruses of types 1 and 2, in the case of human encephalomyocarditis viruses, in the case of influenza viruses, such as, especially, influenza A and influenza B viruses, in the case of vaccinia and parainfluenza viruses and very especially in the case of the viruses mentioned in the Examples.

These compounds of the formula I can be used for the prophylaxis and treatment of virus infections, especially in warm-blooded animals, including humans, by administering them enterally or parenterally, especially together with suitable adjuncts or carriers. They are preferably applied to the mucous membranes, for example intranasally, rectally or vaginally, or to the conjunctiva of the eye, or orally. However, the antiviral effect also occurs in the case of administration by other routes, for example subcutaneously, intravenously or intramuscularly, or in the case of application to normal skin.

The dosage of the active ingredient depends, inter alia, on the species of warm-blooded animal, the organism's resistance, the method of administration and the type of virus. There is relatively little relationship between the dosage and the effect.

For prevention, a single dose of from approximately 0.01 mg to approximately 10 mg, preferably from 0.05 to 1 mg, for example 0.2 mg, of active ingredient is administered to a warm-blooded animal of approximately 70 kg body weight, for example a human. The prophylactic effect of this dose lasts for several weeks. If necessary, for example when there is an increased risk of infection, the administration of this dose can be repeated.

The therapeutic dose for warm-blooded animals of approximately 70 kg body weight is from 0.1 mg to 25 mg, preferably from 0.1 to 1 mg, for example 0.5 mg, especially in the case of oral administration. The dose in the case of topical, especially intranasal, administration is up to ten times lower. If necessary, the administration of these compounds of the formula I can be repeated until there is an improvement in the illness. Often, however, a single administration is sufficient.

The invention relates especially to sugar derivatives of the formula I in which the sugar moiety is derived from D-glucose, D-mannose or D-galactose, $X^1$ represents oxygen, sulphur or the group NH, $X^2$ represents oxygen or the group NH, $R^1$, $R^4$ and $R^6$ each represents, independently of the others, hydrogen, lower alkanoyl, a radical of the formula Ia,

(Ia)

in which n represents 0 or 1, $Y^1$ represents unsubstituted or substituted alkylene which may be interrupted by carbonylimino or carbonyloxy, $X^3$ represents oxygen or the group NH and $A^1$ represents lower alkanoyl that is substituted by aryl, heteroaryl or heteroarylthio and that may be additionally substituted by an ethylene radical which, with the above-mentioned aryl or heteroaryl substituent, forms a five-membered ring, or represents ortho- or ortho/meta-substituted aroyl, or $R^1$, $R^4$ and $R^6$ each represents, independently of the others, a radical of the formula Ib

(Ib)

in which n and $Y^1$ have the meanings mentioned above and $A^2$ represents lower alkoxy substituted by aryl, heteroaryl or heteroarylthio, $R^2$ represents unsubstituted or hydroxy-substituted lower alkanoyl or one of the above-mentioned radicals of the formulae Ia and Ib, $R^3$ represents hydrogen, lower alkyl or cycloalkyl and $R^5$ represents hydrogen, or $R^3$ and $R^5$ together represent lower alkylidene or cycloalkylidene, $R^7$ represents hydrogen or lower alkyl, or $R^7$ and $R^9$ together represent trimethylene, $R^8$ represents hydrogen or lower alkyl, $R^9$ represents hydrogen or lower alkyl that is unsubstituted or substituted by hydroxy, mercapto, lower alkylthio, carboxy, lower alkoxycarbonyl, carbamoyl or by a radical of the formula Ic, Id, Ie or If

(Ic)

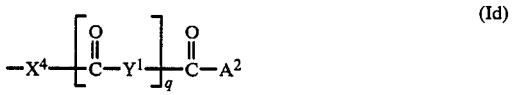
(Id)

(Ie)

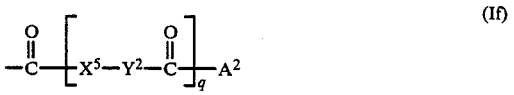
(If)

in which q represents 0 or 1, $X^4$ represents oxygen or sulphur and $X^5$ and $X^6$ each represents, independently of the other, oxygen or the group NH, and the other substituents have the meanings mentioned above, $R^{10}$ and $R^{12}$ each represents, independently of the other, lower alkoxy, hydroxy, amino, lower alkylamino that is substituted by carboxy, carbamoyl or by lower alkoxycarbonyl and that may be additionally substituted by amino, hydroxy, carboxy, 2-aminoethylthio, 2-aminoethoxy and/or by the sulpho group —$SO_3H$, a radical of the formula Ig,

in which $Y^2$ represents unsubstituted or substituted alkylene in which a methylene group may have been replaced by oxygen or sulphur and which may be interrupted by carbonylimino or carbonyloxy, and in which $X^5$, $X^6$ and $A^1$ have the meanings mentioned above, or a radical of the formula Ih,

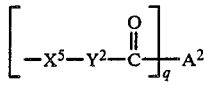

in which q, $X^5$, $Y^2$ and $A^2$ have the meanings mentioned above, and $R^{11}$ represents hydrogen, carboxy or carbamoyl, the compounds of the formula I having a minimum of one and a maximum of three radicals $A^1$ and/or $A^2$, and to salts of such compounds having at least one saltforming group.

Preferred are compounds of the formula I in which the sugar moiety is derived from D-glucose, that is to say in which the substituents —NH—$R^2$ and —$OR^4$ are in the α-configuration, and salts of such compounds having at least one salt-forming group.

Also preferred are the above-mentioned compounds of the formula I in which $R^3$ represents hydrogen, lower alkyl or, together with $R^5$, optionally $C_{1-3}$-alkyl-substituted methylene or optionally substituted benzylidene, especially compounds of this type in which $R^2$ represents benzoyl.

The invention relates especially to the above-mentioned sugar derivatives of the formula I in which $A^1$ represents the acyl radical of a carboxylic acid selected from the group consisting of 6-chloro-5-cyclohexylindan-1-carboxylic acid (clindanac), 2-[4,5-bis-(4-methoxyphenyl)-oxazol-2-yl]-propionic acid, 2-(5-chloro-4-cyclohexyl-2-hydroxyphenyl)-acetic acid, 2[4,5-bis-(4-methoxyphenyl)-oxazol-2-yl]-2-methylpropionic acid, 2-(3-fluoro-4-phenylphenyl)-propionic acid (flurbiprofen), (±)-5-benzoyl-3H-1,2-dihydropyrrolo[a]pyrrole-1-carboxylic acid, 2-[4-(1,3-dihydro-1-oxo-2H-isoindol-2-yl)-phenyl]-propionic acid (indoprofen), 2-{2-[(2,6-dichlorophenyl)-amino]-phenyl}phenyl)-amino]-5-fluorophenyl}-acetic acid, 2-(2,3-dimethylphenyl)-aminobenzoic acid, 2-[4,5-bis-(4-methoxyphenyl)-imidazol-2-yl]-2-methylpropionic acid, 2-{2-[(2,6-dichlorophenyl)-amino]-5-fluorophenyl}acetic acid, 2-(3-benzoylphenyl)-propionic acid (ketoprofen), 2-S-[4,5-bis-(4-methoxyphenyl)-thiazol-2-yl]-mercaptoacetic acid, 3-S-[4,5-bis-(4-methoxyphenyl)thiazol-2-yl]-mercaptopropionic acid, 2-{2-[(2,6-dichloro-4-fluorophenyl)-amino]-phenyl}-acetic acid, 5-(2,4-difluorophenyl)-2-hydroxybenzoic acid (diflunisal), 2-(6-chloro-9H-carbazol-2-yl)-propionic acid (carprofen), 2-(4-isobutylphenyl)-propionic acid (ibuprofen), 1-(4-chlorobenzoyl)-5-methoxy-2-methylindol-3-ylacetic acid (indomethacin), 2-(6-methoxynaphth-2-yl)-pro-pionic acid (naproxen), 2-[3-chloro-4-(3-pyrrolin-1-yl)-phenyl]-propionic acid (pirprofen), 2-(5H-[1]benzopyrano[2,3-b]pyridin-7-yl)-propionic acid (pranoprofen), 5-(4-methylbenzoyl)-1-methylpyrrol-2-ylacetic acid (tolmetin) and 2-[4,5-bis-(4-methoxyphenyl)-oxazol-2-yl]-acetic acid, and to salts of such compounds having at least one salt-forming group.

The invention relates very especially to the above-mentioned compounds of the formula I in which $A^2$ represents substituted lower alkoxy selected from the group consisting of 2-[4,5-bis-(4-methoxyphenyl) thiazol-2-ylthio]-ethoxy, 2-[4,5-bis-(4-methoxyphenyl)imidazol-2-yl]-2-methylpropoxy and 3-[4,5-bis-(4-methoxyphenyl)-thiazol-2-ylthio]-propoxy, and to salts of such compounds having at least one salt-forming group.

The invention relates more especially to the above-mentioned compounds of the formula I in which $X^1$ and $X^2$ represent oxygen, $R^2$ represents unsubstituted or hydroxy-substituted $C_{2-4}$-alkanoyl or a radical of the formula Ia or Ib as defined above, $R^3$ represents hydrogen or lower alkyl, $R^5$, $R^7$ and $R^8$ represent hydrogen, $R^9$ represents lower alkyl that is unsubstituted or substituted by hydroxy, mercapto, methylthio or by a radical of the formula Ic, Id, Ie or If as defined above, $R^{10}$ represents hydroxy or amino, $R^{11}$ represents hydrogen, $R^{12}$ represents lower alkoxy, hydroxy, amino or a radical of the formula Ig or Ih as defined above, and the other substituents have the meanings mentioned above, it being necessary for the compounds of the formula I to have a radical $A^1$ or $A^2$, and to pharmaceutically acceptable salts of such compounds having at least one salt-forming group.

The invention relates very especially to the above-mentioned compounds of the formula I that have a radical of the formula Ia, Ib, Ic, Id, Ie, If, Ig or Ih in which $Y^1$ or $Y^2$ represents unsubstituted or hydroxy- or carboxy-substituted alkylene that has up to 12 carbon atoms and may be interrupted by carbonylimino or carbonyloxy, and the other substituents have the meanings mentioned above, and to pharmaceutically acceptable salts of such compounds having at least one salt-forming group.

The invention relates especially to the above-mentioned compounds of the formula I that have a radical of the formula Ia, Ic, Ie or Ig in which $A^1$ represents the acyl radical of indomethacin, ketoprofen, naproxen, ibuprofen or, preferably, diclofenac, and the other substituents have the meanings mentioned above, and to pharmaceutically acceptable salts of such compounds having at least one salt-forming group.

Especially preferred are compounds of the formula I in which the sugar moiety is derived from D-glucose, $X^1$ and $X^2$ represent oxygen, $R^1$ represents hydrogen or lower alkanoyl, $R^2$ represents lower alkanoyl or benzoyl, $R^3$ represents hydrogen or lower alkyl or, together with $R^5$, a lower alkylidene radical that is unsubstituted or substituted by optionally halosubstituted phenyl, $R^4$ represents hydrogen or lower alkanoyl, $R^5$ represents hydrogen or, together with $R^3$, a lower alkylidene radical that is unsubstituted or substituted by optionally halo-substituted phenyl, $R^6$ represents hydrogen, lower alkanoyl or a radical of the formula Ia, in which n represents 1, $Y^1$ represents unsubstituted or carboxy-substituted lower alkylidene, $X^3$ represents NH and $A^1$ represents 2-{2-[(2,6-dichlorophenyl)-amino]-phenyl}-acetyl, $R^7$ and $R^8$ represent hydrogen, $R^9$ represents lower alkyl, $R^{10}$ represents amino, lower alkoxy or a radical of the formula Ig in which $X^5$ represents NH, $Y^2$ represents a lower alkylene radical which may be interrupted by carbonylimino and substituted by hydroxy, $X^6$ represents NH and $A^1$ represents 2-(6-methoxynaphth-2-yl)-propionyl, $R^{11}$ represents hydrogen or lower alkoxycarbonyl, and $R^{12}$ represents lower alkoxy, hydroxy, amino, a radical of the formula Ig in which $X^5$ represents NH, $Y^2$ represents $C_{2-10}$-alkylene that is unsubstituted or substituted by hydroxy, lower alkanoyloxy, amino, carboxy and/or by benzyloxycarbonyl, and in which a methylene group may have been replaced by oxygen, sulphur, sulphinyl

or carbonylimino

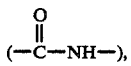

$X^6$ represents NH or oxygen and $A^1$ represents 2-{2-[(2,6-dichlorophenyl)-amino]-phenyl}-acetyl, 1-benzoyl-5-methoxy-2-methylindol-3-ylacetyl, 2-(6-methoxynaphth-2-yl)-propionyl, 2-(4-isobutylphenyl)-propionyl, 2-[3-(hydroxybenzyl)phenyl]-propionyl, 2-(3-benzoylphenyl)-propionyl, 2-[3-chloro-4-(pyrrol-1-yl)-phenyl]-propionyl, 1-(4-chlorobenzoyl)-5-methoxy-2-methylindol-3-ylacetyl, 2-[3-chloro-4-(3-pyrrolin-1-yl)-phenyl]-propionyl or 2-[4,5-bis-(4-methoxyphenyl)-oxazol-2-yl]-propionyl, or $R^{10}$ represents a radical of the formula Ih in which q represents 1, $X^5$ represents NH, $Y^2$ represents lower alkylene and $A^2$ represents 2-[4,5-bis-(4-methoxyphenyl)-thiazol-2-ylthio]ethoxy, with the proviso that the compounds contain one and only one radical $A^1$ or $A^2$, and to pharmaceutically acceptable salts of such compounds having at least one salt-forming group. More especially preferred are the above-mentioned compounds in which $Y^1$ represents 2-carboxyethylidene or 2-methylpropylidene or $Y^2$ represents di- or tetra-methylene, ethylidene, 1-carboxydimethylene, 1-carboxytetramethylene, 1-carboxypentamethylene, 2-hydroxytrimethylene, 1-carboxy-3-oxapentamethylene

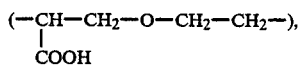

1-benzyloxycarbonyl-3-thiapentamethylene, 4-(ethylidenecarbonylimino)-n-butyl [—CH(CH₃)—CONH—(CH₂)₄—], 3-(ethylidenecarbonylimino)-2-hydroxypropyl, 2-acetoxy-3-(ethylidenecarbonylimino)propyl, 3-[(4-aminopentylidene)-carbonylimino]-2hydroxypropyl or 1-benzyloxycarbonyl-2-(ethylene-1-sulphinyl)-dimethylene

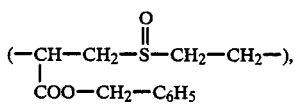

and to pharmaceutically acceptable salts of such compounds having at least one salt-forming group. The invention relates preferably to the above-mentioned compounds of the formula I in which the radical $A^1$ is other than the acyl radical of indomethacin. The invention relates first and foremost to the compounds described in the Examples and to pharmaceutically acceptable salts of such compounds having at least one salt-forming group. The invention also relates to the novel compounds of the formula II (which can be used both as intermediates and as end products)

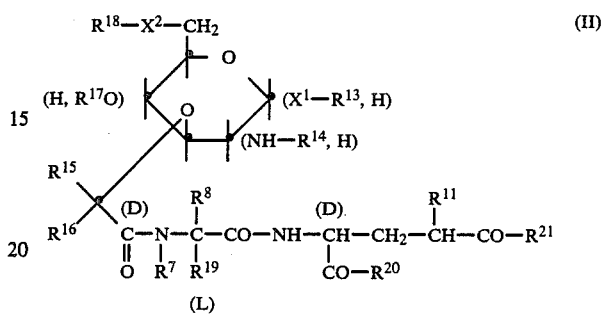

in which the sugar moiety is derived from D-glucose, D-mannose or D-galactose, $X^1$, $X^2$, $R^7$, $R^8$ and $R^{11}$ have the meanings mentioned above, $R^{13}$, $R^{17}$ and $R^{18}$ each represents, independently of the others, hydrogen or lower alkanoyl, or $R^{13}$ alternatively represents unsubstituted or substituted benzyl, $R^{14}$ represents unsubstituted or hydroxy-substituted lower alkanoyl or unsubstituted or substituted benzoyl, $R^{15}$ represents cycloalkyl and $R^{16}$ represents hydrogen, or $R^{15}$ and $R^{16}$ together represent lower alkylidene, cycloalkylidene or unsubstituted or substituted benzylidene, $R^{19}$ represents hydrogen or lower alkyl that is unsubstituted or substituted by hydroxy, mercapto, lower alkylthio, carboxy, lower alkoxycarbonyl or by carbamoyl, $R^{20}$ and $R^{21}$ each represents, independently of the other, lower alkoxy, hydroxy, amino, or lower alkylamino that is substituted by carboxy, carbamoyl or by lower alkoxycarbonyl and that may be additionally substituted by amino, hydroxy, carboxy, 2-aminoethylthio, 2-aminoethoxy and/or by the sulpho group —SO₃H, to salts of these compounds having at least one salt-forming group, to processes for their manufacture, and to their use as intermediates for the manufacture of the compounds of the formula I and as immunostimulants.

The invention relates especially to those compounds of the formula II in which $R^{13}$, $R^{17}$ and $R^{18}$ each represents, independently of the others, hydrogen or lower alkanoyl, $R^{14}$ represents unsubstituted or hydroxy-substituted lower alkanoyl, $R^{15}$ represents cycloalkyl and $R^{16}$ represents hydrogen, or $R^{15}$ and $R^{16}$ together represent lower alkylidene or cycloalkylidene.

The compounds of the formula II are manufactured in a manner known per se, for example analogously to the manner described in German Offenlegungsschrift No. 26 55 500, a possible starting material being obtained, for example, by reacting a compound of the formula III

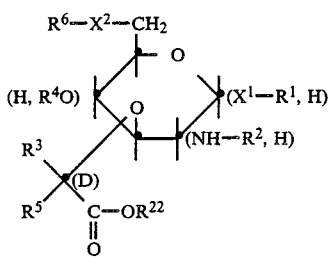
(III)

in which $R^3$ and $R^5$ represent hydrogen and $R^{22}$ represents an aliphatic, aromatic or aliphatic radical, for example methyl, and the other substituents have the meanings mentioned above, with a base that is capable of splitting off one of the radicals $R^3$ and $R^5$ in the form of a $H\oplus$ion, for example with sodium hydroxide, sodium amide or lithium hydride, then reacting the resulting carbanion with a ketone, eliminating water from the resulting intermediate and linking on the peptide sequence.

The invention also relates to the novel intermediate obtained according to the above process sequence after eliminating water.

The compounds of the formula I are also manufactured in a manner known per se.

Process variant (a)

Compounds of the formula I in which at least one of the radicals $R^{10}$ and $R^{12}$ is a radical of the formula Ig or Ih, or salts of such compounds having at least one salt-forming group, are obtained, for example, as follows: a compound of the formula IV

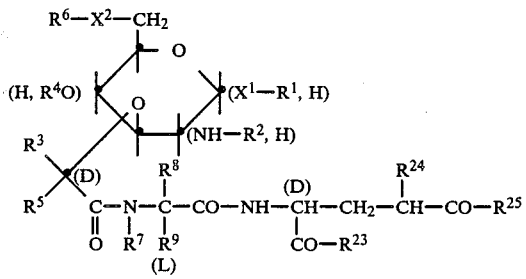
(IV)

in which at least one of the radicals $R^{23}$ and $R^{25}$ is hydroxy and the other of the radicals $R^{23}$ and $R^{25}$ is hydroxy protected by a carboxy protecting group, or is lower alkoxy, amino, lower alkylamino that is substituted by lower alkoxycarbonyl or by protected carboxy and that may be additionally substituted by amino, hydroxy, 2-aminoethylthio, 2-aminoethoxy, protected carboxy or by a sulpho group that is optionally present in protected form, or is a radical, as defined above, of the formula Ig or Ih, $R^{24}$ represents hydrogen, carbamoyl or protected carboxy, and the other substituents have the meanings mentioned above (carboxy and amino groups present in a compound of the formula IV and, if necessary, hydroxy and other functional groups, with the exception of the group participating in the reaction, being in protected form), or a reactive carboxylic acid derivative of a compound of the formula IV, is reacted in one step or in stages with a compound of the formula V $$H-[X^5-Y^2-X^7]_r-A^3 \quad (V)$$

in which $X^5$ and $Y^2$ have the meanings mentioned above, $A^3$ has the above-mentioned meaning of $A^1$ or $A^2$, $X^7$ has the above-mentioned meaning of $X^6$ if $A^3$ represents $A^1$, or $X^7$ represents a carbonyl group if $A^3$ represents $A^2$, and r represents 1 if A3 represents $A^1$, or r has the above-mentioned meaning of q if $A^3$ represents $A^2$, or with a reactive derivative of a compound of the formula V, protecting groups present are removed and, if desired, a resulting compound of the formula I having at least one salt-forming group is converted into a salt.

Protecting groups and the manner in which they are introduced and removed are described, for example, in "Protective Groups in Organic Chemistry", Plenum Press, London, New York 1973, and in "Methoden der organischen Chemie", Houben-Weyl, 4th Edition, Vol. 15/1, Georg-Thieme-Verlag, Stuttgart 1974 and in Theodora W. Greene, "Protective Groups in Organic Synthesis", John Wiley & Sons, New York 1981. It is characteristic of protecting groups that they can be readily removed, that is to say without undesired secondary reactions taking place, for example by solvolysis, reduction, photolysis or alternatively under physiological conditions Hydroxy-protecting groups are, for example, acyl radicals, such as optionally substituted, for example halo-substituted, lower alkanoyl, such as 2,2-dichloroacetyl, or acyl radicals of carbonic acid semi-esters, especially tert.-butoxycarbonyl, optionally substituted benzyloxycarbonyl or diphenylmethoxycarbonyl, for example 4-nitrobenzyloxycarbonyl, or 2-halo-lower alkoxycarbonyl, such as 2,2,2-trichloroethoxycarbonyl, also trityl or formyl, or organic silyl or stannyl radicals, also readily removable etherifying groups, such as tert.-lower alkyl, for example tert.-butyl, 2-oxa- or 2-thia-aliphatic or -cycloaliphatic hydrocarbon radicals, especially 1-lower alkoxy-lower alkyl or 1-lower alkylthio-lower alkyl, for example methoxymethyl, 1-methoxyethyl, 1-ethoxyethyl, methylthiomethyl, 1-methylthioethyl or 1-ethylthioethyl, or 2-oxa- or 2-thia-cycloalkyl having 5 or 6 ring atoms, for example tetrahydrofuryl or 2-tetrahydropyranyl or corresponding thia analogues, and also optionally substituted 1-phenyl-lower alkyl, such as optionally substituted benzyl or diphenylmethyl, there being suitable as substituents of the phenyl radicals, for example, halogen, such as chlorine, lower alkoxy, such as methoxy, and/or nitro.

Carboxy groups are customarily protected in esterified form, such ester groupings being readily cleavable under mild conditions. Carboxy groups protected in this manner contain as esterifying groups especially lower alkyl groups that are branched in the 1-position or suitably substituted in the 1- or 2-position. Preferred carboxy groups in esterified form are, inter alia, tert.-lower alkoxycarbonyl, for example tert.-butoxycarbonyl, arylmethoxycarbonyl having one or two aryl radicals, these being phenyl radicals optionally mono- or poly-substituted, for example, by lower alkyl, such as tert.-lower alkyl, for example tert.-butyl, lower alkoxy, such as methoxy, hydroxy, halogen, for example chlorine, and-/or by nitro, such as benzyloxycarbonyl optionally substituted, for example, as mentioned above, for example 4-methoxybenzyloxycarbonyl or 4-nitrobenzyloxycarbonyl, or diphenylmethoxycarbonyl optionally substituted, for example, as mentioned above, for example diphenylmethoxycarbonyl or di-(4-methoxyphenyl)-methoxycarbonyl, 1-lower alkoxy-lower alkoxycarbonyl, such as methoxymethoxycarbonyl, 1-methoxyethoxycarbonyl or 1-ethoxymethoxycarbonyl, 1-lower alkylthio-lower alkoxycarbonyl, such as 1-methylthiomethoxycarbonyl or 1-ethylthioethoxycarbonyl, aroylmethoxycarbonyl in which the aroyl group represents benzoyl optionally substituted, for example, by halogen, such as bromine, for example phenacyloxycarbonyl, 2-halo-lower alkoxycarbonyl, for example 2,2,2-trichloroethoxycarbonyl, 2-bromoethoxycarbonyl or 2-iodoethoxycarbonyl, or 2-(trisubstituted silyl)-ethoxycarbonyl in which each of the substituents, independently of the others, represents an aliphatic, araliphatic, cycloaliphatic or aromatic hydrocarbon radical that is optionally substituted, for example, by lower alkyl, lower alkoxy, aryl, halogen and/or by nitro, such as corresponding optionally substituted lower alkyl, phenyl-lower alkyl, cycloalkyl or phenyl, for example 2-tri-lower alkylsilylethoxycarbonyl, 2-trimethylsilylethoxycarbonyl or 2-(di-n-butylmethylsilyl)-ethoxycarbonyl, or 2-triarylsilylethoxycarbonyl, such as 2-triphenylsilylethoxycarbonyl.

The organic silyl or stannyl radicals mentioned hereinbefore and hereinafter preferably contain lower alkyl, especially methyl, as substituent of the silicon or tin atoms. Corresponding silyl or stannyl groups are especially tri-lower alkylsilyl, especially trimethylsilyl, also dimethyl-tert.-butylsilyl, or correspondingly substituted stannyl, for example tri-n-butylstannyl.

Preferred protected carboxy groups are tert.-lower alkoxycarbonyl, such as tert.-butoxycarbonyl, and especially benzyloxycarbonyl or diphenylmethoxycarbonyl optionally substituted, for example, as mentioned above, such as 4-nitrobenzyloxycarbonyl, and more especially 2-(trimethylsilyl)-ethoxycarbonyl.

A protected amino group can be, for example, in the form of a readily cleavable acylamino, arylmethylamino, etherified mercaptoamino, 2-acyl-lower alk-1-enylamino, silylamino or stannylamino group or in the form of an azido group.

In a corresponding acylamino group, acyl is, for example, the acyl radical of an organic carboxylic acid having, for example, up to 18 carbon atoms, especially an alkanecarboxylic acid optionally substituted, for example, by halogen or aryl, or of benzoic acid optionally substituted, for example, by halogen, lower alkoxy or nitro, or of a carbonic acid semi-ester. Such acyl groups are, for example, lower alkanoyl, such as formyl, acetyl or propionyl, halo-lower alkanoyl, such as 2-haloacetyl, especially 2-chloro-, 2-bromo-, 2-iodo-, 2,2,2-trifluoro- or 2,2,2-trichloro-acetyl, benzoyl optionally substituted, for example, by halogen, lower alkoxy or by nitro, for example benzoyl, 4-chlorobenzoyl, 4-methoxybenzoyl or 4-nitrobenzoyl, or lower alkoxycarbonyl that is branched in the 1-position of the lower alkyl radical or suitably substituted in the 1- or 2-position, especially tert.-lower alkoxycarbonyl, for example tert.-butoxycarbonyl, arylmethoxycarbonyl having one or two aryl radicals that are preferably phenyl optionally mono- or polysubstituted, for example, by lower alkyl, especially tert.-lower alkyl, such as tert.-butyl, lower alkoxy, such as methoxy, hydroxy, halogen, for example chlorine, and/or by nitro, such as optionally substituted benzyloxycarbonyl, for example 4-nitrobenzyloxycarbonyl, or substituted diphenylmethoxycarbonyl, for example benzhydryloxycarbonyl or di-(4-methoxyphenyl)-methoxycarbonyl, aroylmethoxycarbonyl in which the aroyl group preferably represents benzoyl optionally substituted, for example, by halogen, such as bromine, for example phenacyloxycarbonyl, 2-halo-lower alkoxycarbonyl, for example 2,2,2-trichloroethoxycarbonyl, 2-bromoethoxycarbonyl or 2-iodoethoxycarbonyl, or 2-(tri-substituted silyl)ethoxycarbonyl in which each of the substituents, independently of the others, represents an aliphatic, araliphatic, cycloaliphatic or aromatic hydrocarbon radical that has up to 15 carbon atoms and is optionally substituted, for example, by lower alkyl, lower alkoxy, aryl, halogen or by nitro, such as corresponding optionally substituted lower alkyl, phenyl-lower alkyl, cycloalkyl or phenyl, for example 2-tri-lower alkylsilylethoxycarbonyl, such as 2-trimethylsilylethoxycarbonyl or 2-(di-n-butylmethylsilyl)ethoxycarbonyl, or 2-triarylsilylethoxycarbonyl, such as 2-triphenylsilylethoxycarbonyl.

Further acyl radicals coming into consideration as amino-protecting groups are also corresponding radicals of organic phosphoric, phosphonic or phosphinic acids, such as di-lower alkylphosphoryl, for example dimethylphosphoryl, diethylphosphoryl, di-n-propylphosphoryl or diisopropylphosphoryl, dicycloalkylphosphoryl, for example dicyclohexylphosphoryl, optionally substituted diphenylphosphoryl, for example diphenylphosphoryl, di-(phenyl-lower alkyl)-phosphoryl that is optionally substituted, for example, by nitro, for example dibenzylphosphoryl or di-(4-nitrobenzyl)-phosphoryl, optionally substituted phenoxyphenylphosphonyl, for example phenoxyphenylphosphonyl, di-lower alkylphosphinyl, for example diethylphosphinyl, or optionally substituted diphenylphosphinyl, for example diphenylphosphinyl.

In an arylmethylamino group that is a mono-, dior especially tri-arylmethylamino group, the aryl radicals are especially optionally substituted phenyl radicals. Such groups are, for example, benzylamino, diphenylmethylamino and especially tritylamino.

An etherified mercapto group in an amino group protected by such a radical is especially arylthio or aryl-lower alkylthio in which aryl is especially phenyl that is optionally substituted, for example, by lower alkyl, such as methyl or tert.-butyl, lower alkoxy, such as methoxy, halogen, such as chlorine, and/or by nitro. A corresponding amino-protecting group is, for example, 4-nitrophenylthio.

In a 2-acyl-lower alk-1-en-1-yl radical that may be used as an amino-protecting group, acyl is, for example, the corresponding radical of a lower alkanecarboxylic acid, of benzoic acid that is optionally substituted, for example, by lower alkyl, such as methyl or tert.-butyl, lower alkoxy, such as methoxy, halogen, such as chlorine, and/or by nitro, or especially of a carbonic acid semi-ester, such as a carbonic acid lower alkyl semi-ester. Corresponding protecting groups are especially 1-lower alkanoylprop-1-en-2-yl, for example 1-acetylprop-1-en-2-yl, or 1-lower alkoxycarbonylprop-1-en-2-yl, for example 1-ethoxycarbonylprop-1-en-2-yl.

An amino group can also be protected in protonated form; as corresponding anions there come into consideration especially those of strong inorganic acids, such as hydrohalic acids, for example the chlorine or bromine anion, or organic sulphonic acids, such as p-toluenesulphonic acid.

Preferred amino-protecting groups are acyl radicals of carbonic acid semi-esters, especially tert.-butoxycarbonyl, or benzyloxycarbonyl or diphenylmethoxycarbonyl each of which is optionally substituted, for example as indicated, for example 4-nitrobenzyloxycarbonyl, or 2-halo-lower alkoxycarbonyl, such as 2,2,2-trichloroethoxycarbonyl, also trityl or formyl.

A mercapto group, such as, for example, in cysteine, can be protected especially by S-alkylation with optionally substituted alkyl radicals, by thioacetal formation, S-acylation or by establishing asymmetrical disulphide groupings. Preferred mercapto-protecting groups are, for example, benzyl optionally substituted in the phenyl radical, for example by methoxy or nitro, such as 4-methoxybenzyl, diphenylmethyl optionally substituted in the phenyl moiety, for example by methoxy, such as 4,4'-dimethoxydiphenylmethyl, triphenylmethyl, trimethylsilyl, benzylthiomethyl, tetrahydropyranyl, acylaminomethyl, benzoyl, benzyloxycarbonyl or aminocarbonyl, such as ethylaminocarbonyl.

The reaction is preferably carried out by reacting the compound of the formula IV in the form of an activated carboxylic acid derivative with the compound of the formula V, it also being possible for the activation of the carboxylic acid of the formula IV to be carried out in situ in the presence of a compound of the formula V.

Activated carboxylic acid derivatives of a compound of the formula IV are especially reactive activated esters or reactive anhydrides, also reactive cyclic amides; reactive derivatives of acids of the formula IV can also be formed in situ.

Activated esters of acids are especially esters that are unsaturated at the linking carbon atom of the esterifying radical, for example of the vinyl ester type, such as actual vinyl esters (which can be obtained, for example, by transesterification of a corresponding ester with vinyl acetate; activated vinyl ester method), carbamoylvinyl esters (which can be obtained, for example, by treating the corresponding acid with an isoxazolium reagent; 1,2-oxazolium or Woodward method), or 1-lower alkoxyvinyl esters (which can be obtained, for example, by treating the corresponding acid with a lower alkoxyacetylene; ethoxyacetylene method), or esters of the amidino type, such as N,N'-disubstituted amidino esters (which can be obtained, for example, by treating the corresponding acid with a suitable N,N'-disubstituted carbodiimide, for example N,N'-dicyclohexyl carbodiimide; carbodiimide method), or N,N-disubstituted amidino esters (which can be obtained, for example, by treating the corresponding acid with an N,N-disubstituted cyanamide; cyanamide method), suitable aryl esters, especially phenyl esters suitably substituted by electron-attracting substituents (which can be obtained, for example, by treating the corresponding acid with a suitably substituted phenol, for example 4-nitrophenol, 4-methylsulphonylphenol, 2,4,5-trichlorophenol, 2,3,4,5,6-pentachlorophenol or 4-phenyldiazophenol, in the presence of a condensation agent, such as N,N'-dicyclohexyl carbodiimide; activated aryl esters method), cyanomethyl esters (which can be obtained, for example, by treating the corresponding acid with chloroacetonitrile in the presence of a base; cyanomethyl esters method), thioesters, especially phenylthioesters optionally substituted, for example, by nitro (which can be obtained, for example, by treating the corresponding acid with thiophenols that are optionally substituted, for example, by nitro, inter alia with the aid of the anhydride or carbodiimide method; activated thioesters method), or amino or amido esters (which can be obtained, for example, by treating the corresponding acid with an N-hydroxyamino or N-hydroxyamido compound, for example N-hydroxysuccinimide, N-hydroxypiperidine, N-hydroxyphthalimide or 1-hydroxybenzotriazole, for example according to the anhydride or carbodiimide method; activated N-hydroxyesters method), or silyl esters (which can be obtained, for example, by treating the corresponding acid with a silylating agent, for example hexamethyldisilazane).

Anhydrides of acids of the formula IV may be symmetrical or, preferably, mixed anhydrides of these acids, for example anhydrides with inorganic acids, such as acid halides, especially acid chlorides (which can be obtained, for example, by treating the corresponding acid with thionyl chloride, phosphorus pentachloride or oxalyl chloride; acid chloride method), azides (which can be obtained, for example, from a corresponding acid ester by way of the corresponding hydrazide and the treatment of the latter with nitrous acid; azide method), anhydrides with carbonic acid semiderivatives, such as with corresponding esters, for example carbonic acid lower alkyl semi-esters (which can be obtained, for example, by treating the corresponding acid with haloformic acid lower alkyl esters, such as chloroformic acid lower alkyl esters, or with a 1-lower alkoxycarbonyl-2-lower alkoxy-1,2-dihydroquinoline, for example 1-lower alkoxycarbonyl-2-ethoxy-1,2-dihydroquinoline; mixed 0-alkylcarbonic acid anhydrides method), or anhydrides with dihalogenated, especially dichlorinated, phosphoric acid (which can be obtained, for example, by treating the corresponding acid with phosphorus oxychloride; phosphorus oxychloride method), or anhydrides with organic acids, such as mixed anhydrides with organic carboxylic acids (which can be obtained, for example, by treating the corresponding acid with an optionally substituted lower alkanecarboxylic acid halide or phenylalkanecarboxylic acid halide, for example phenylacetic acid chloride, pivalic acid chloride or trifluoroacetic acid chloride; mixed carboxylic acid anhydrides method) or with organic sulphonic acids (which can be obtained, for example, by treating a salt, such as an alkali metal salt, of the corresponding acid with a suitable organic sulphonic acid halide, such as lower alkanesulphonic acid chloride or arylsulphonic acid chloride, for example methane- or p-toluene-sulphonic acid chloride; mixed sulphonic acid anhydrides method), and symmetrical anhydrides (which can be obtained, for example, by condensing the corresponding acid in the presence of a carbodiimide or of 1-diethylaminopropine; symmetrical anhydrides method).

Suitable cyclic amides are especially amides having five-membered diazacycles of aromatic character, such as amides with imidazoles, for example imidazole (which can be obtained, for example, by treating the corresponding acid with N,N'-carbonyldiimidazole; imidazolide method), or pyrazoles, for example 3,5-dimethylpyrazole (which can be obtained, for example, by way of the acid hydrazide by treatment with acetylacetone; pyrazolide method).

As mentioned, derivatives of acids of the formula IV can also be formed in situ. For example, N,N'-disubstituted amidino esters can be formed in situ by reacting a mixture of the starting material of the formula V and the acid of the formula IV in the presence of a suitable N,N-disubstituted carbodiimide, for example N,N'-dicyclohexyl carbodiimide It is also possible to form amino or amido esters of acids of the formula IV in the presence of the starting material of the formula V to be acylated by reacting a mixture of the corresponding acid and amino starting materials in the presence of an N,N'-disubstituted carbodiimide, for example N,N'-dicyclohexyl carbodiimide, and an N-hydroxyamine or N-hydroxyamide, for example N-hydroxysuccinimide, optionally in the presence of a suitable base, for example 4-dimethylaminopyridine.

Alternatively, process variant a) can be carried out by reacting the acid IV with a reactive derivative of a compound of the formula V.

A derivative of a compound of the formula V in which the radical $H-X^5$ is the group NH and in which the amino group participating in the reaction is in reactive form can be manufactured, for example, by reaction with a phosphite, for example diethyl chlorophosphite, 1,2-phenylene chlorophosphite, ethyl dichlorophosphite, ethylene chlorophosphite or tetraethyl pyrophosphite. A reactive form of a compound of the formula V is, for example, also a carbamic acid halide or an isocyanate, in a compound of the formula V the amino group participating in the reaction being bonded to halocarbonyl, for example chlorocarbonyl, or being in the form of an isocyanate group; in the latter case only compounds of the formula I that carry a hydrogen atom at the nitrogen atom of the amide group formed by the reaction can be obtained.

A derivative of a compound of the formula V in which the group $H-X^5$ is hydroxy in reactive form is, for example, a halide. In this case it is also possible, for example, to react a metal salt, such as an alkali metal salt, preferably a caesium salt, of a carboxylic acid of the formula V with the mentioned halide. The reaction between the compounds of the formulae IV and V can, if r represents 1, as mentioned above, also be carried out in stages as follows: the compound of the formula IV is first reacted with a compound of the formula Va

$$H-X^5-Y^2-X^6-H \qquad (Va)$$

in which the substituents have the meanings mentioned above, or with a derivative of this compound in which the group $H-X^5-$ is in reactive form, the group $X^6-H$ if necessary being protected by a protecting group, any protecting group present for the group $X^6-H$ is removed and then the resulting intermediate of the formula IVa

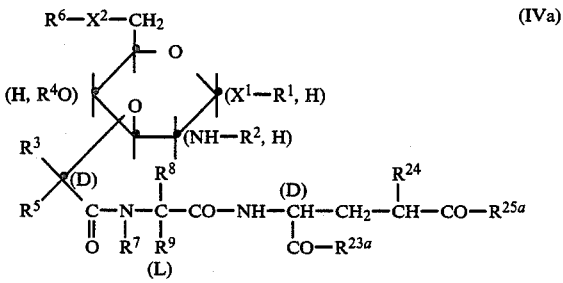

(IVa)

in which at least one of the radicals $R^{23a}$ and $R^{25a}$ is a radical of the formula $-X^5-Y^2-X^6-H$ in which the substituents have the meanings mentioned above, and the other of the radicals $R^{23a}$ and $R^{25a}$ has the above-mentioned meaning of $R^{23}$ or $R^{25}$, as the case may be, and the other substituents have the meanings mentioned above (amino and/or hydroxy groups in a compound of the formula IVa, with the exception of the group participating in the reaction, being in protected form), or a reactive derivative of a compound of the formula IVa, is reacted with a carboxylic acid of the formula $A^1-OH$ in which $A^1$ has the meaning mentioned above (amino and/or hydroxy groups present therein and, if necessary, other functional groups, with the exception of the group participating in the reaction, being in protected form), or with a reactive carboxylic acid derivative of a carboxylic acid of the formula $A^1-OH$, protecting groups present are removed and, if desired, a resulting compound of the formula I having at least one salt-forming group is converted into a salt.

Alternatively, a compound of the formula IV can first be reacted with a compound of the formula Vb,

$$H-X^5-Y^2-\overset{\overset{\displaystyle O}{\|}}{C}-OH \qquad (Vb)$$

in which the substituents have the meanings mentioned above, carboxy groups present in a compound of the formula Vb preferably being in protected form, or with a derivative of this compound in which the group $H-X^5-$ is in reactive form, and then the resulting intermediate of the formula IVb

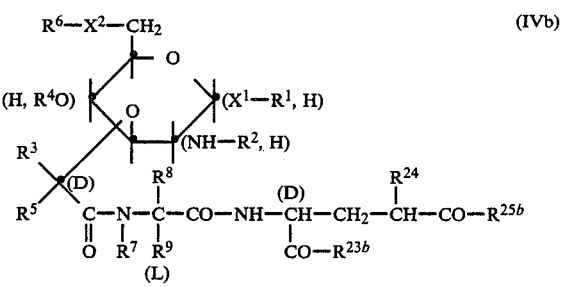

(IVb)

in which at least one of the radicals $R^{23b}$ and $R^{25b}$ is a radical of the formula

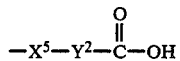

$$-X^5-Y^2-\overset{\overset{\displaystyle O}{\|}}{C}-OH$$

in which the substituents have the meanings mentioned above, and the other of the radicals $R^{23b}$ and $R^{25b}$ has the above-mentioned meaning of $R^{23}$ or $R^{25}$, as the case may be, and the other substituents have the meanings mentioned above (functional groups present in a compound of the formula IVb, such as, especially, amino, hydroxy and/or carboxy groups, with the exception of the group participating in the reaction, if necessary being in protected form), or a reactive carboxylic acid derivative of a compound of the formula IVb, is reacted with a compound of the formula $H-A^2$ in which $A^2$ has the meaning mentioned above (functional groups present therein, such as, especially, amino, hydroxy and/or carboxy groups, with the exception of the group participating in the reaction, if necessary being in protected form), or with a reactive derivative thereof, protecting groups present are removed and, if desired, a resulting compound of the formula I having at least one salt-forming group is converted into a salt.

The invention also relates to those embodiments of the process in which a compound of the formula IVa or IVb obtained in any manner is used as the starting material.

The removal of the protecting groups, for example the carboxy-, amino-, hydroxy- or mercapto-protecting groups, is carried out in a manner known per se, for example by means of solvolysis, especially hydrolysis, alcoholysis or acidolysis, or by means of reduction, especially hydrogenolysis or chemical reduction, optionally in stages or simultaneously, it also being possible to use enzymatic methods.

Thus, tert.-lower alkoxycarbonyl, or lower alkoxycarbonyl substituted in the 2-position by an organic silyl group or in the 1-position by lower alkoxy or lower alkylthio, or optionally substituted diphenylmethoxycarbonyl can be converted into free carboxy, for example, by treatment with a suitable acid, such as formic acid or trifluoroacetic acid, optionally with the addition of a nucleophilic compound, such as phenol or anisole. Optionally substituted benzyloxycarbonyl can be freed, for example, by hydrogenolysis, that is to say by treatment with hydrogen in the presence of a metallic hydrogenation catalyst, such as a palladium catalyst. In addition, suitably substituted benzyloxycarbonyl, such as 4-nitrobenzyloxycarbonyl, can be converted into free carboxy by chemical reduction, for example by treatment with an alkali metal dithionite, for example sodium dithionite, or with a reducing metal, for example zinc, or a reducing metal salt, such as a chromium(II) salt, for example chromium(II) chloride, usually in the presence of an agent that yields hydrogen and that, together with the metal, is capable of producing nascent hydrogen, such as an acid, especially a suitable carboxylic acid, such as a lower alkanecarboxylic acid optionally substituted, for example, by hydroxy, for example acetic acid, formic acid, glycolic acid, diphenylglycolic acid, lactic acid, mandelic acid, 4-chloromandelic acid or tartaric acid, or an alcohol or thiol, water preferably being added. By treatment with a reducing metal or metal salt, as described above, it is also possible to convert 2-halolower alkoxycarbonyl (optionally after conversion of a 2-bromo-lower alkoxycarbonyl group into a corresponding 2-iodo-lower alkoxycarbonyl group) or aroylmethoxycarbonyl into free carboxy, it being possible to cleave aroylmethoxycarbonyl also by treatment with a nucleophilic, preferably salt-forming, reagent, such as sodium thiophenolate or sodium iodide. Substituted 2-silylethoxycarbonyl can also be converted into free carboxy by treatment with a salt of hydrofluoric acid yielding the fluoride anion, such as an alkali metal fluoride, for example sodium or potassium fluoride, in the presence of a macrocyclic polyether ("Crown ether"), or with a fluoride of an organic quaternary base, such as tetra-lower alkylammonium fluoride or tri-lower alkylarylammonium fluoride, for example tetraethylammonium fluoride or tetrabutylammonium fluoride, in the presence of an aprotic polar solvent, such as dimethyl sulphoxide or N,N-dimethylacetamide. Carboxy esterified by an organic silyl group, such as tri-lower alkylsilyl, for example trimethylsilyl, can be freed in customary manner by solvolysis, for example by treatment with water, an alcohol or an acid.

A protected amino group is freed in a manner known per se and, depending on the nature of the protecting groups, by various methods, but preferably by solvolysis or reduction. 2-halo-lower alkoxycarbonylamino (optionally after conversion of a 2-bromo-lower alkoxycarbonylamino group into a 2-iodo-lower alkoxycarbonylamino group), aroylmethoxycarbonylamino or 4-nitrobenzyloxycarbonylamino can be cleaved, for example, by treatment with a suitable chemical reducing agent, such as zinc in the presence of a suitable carboxylic acid, such as aqueous acetic acid. Aroylmethoxycarbonylamino can also be cleaved by treatment with a nucleophilic, preferably salt-forming, reagent, such as sodium thiophenolate, and 4-nitrobenzyloxycarbonylamino also by treatment with an alkali metal dithionite, for example sodium dithionite. Optionally substituted diphenylmethoxycarbonylamino, tert.-lower alkoxycarbonylamino or 2-trisubstituted silylethoxycarbonylamino can be freed by treatment with a suitable acid, for example formic acid or trifluoroacetic acid, optionally substituted benzyloxycarbonylamino can be freed, for example, by hydrogenolysis, that is to say by treatment with hydrogen in the presence of a suitable hydrogenation catalyst, such as a palladium catalyst, optionally substituted triarylmethylamino or formylamino can be freed, for example, by treatment with an acid, such as a mineral acid, for example hydrochloric acid, or an organic acid, for example formic, acetic or trifluoroacetic acid, optionally in the presence of water, and an amino group protected by an organic silyl group can be cleaved, for example, by hydrolysis or alcoholysis. An amino group protected by 2-haloacetyl, for example 2-chloroacetyl, can be freed by treatment with thiourea in the presence of a base, or with a thiolate salt, such as an alkali metal thiolate, of thiourea, and by subsequent solvolysis, such as alcoholysis or hydrolysis, of the reuslting condensation product. An amino group protected by 2substituted silylethoxycarbonyl can also be converted into the free amino group by treatment with a salt of hydrofluoric acid yielding fluoride anions, as indicated above in connection with the freeing of a correspondingly protected carboxy group.

Amino protected in the form of an azido group is converted into free amino, for example, by reduction, for example by catalytic hydrogenation with hydrogen in the presence of a hydrogenation catalyst, such as platinum oxide, palladium or Raney nickel, or alternatively by treatment with zinc in the presence of an acid, such as acetic acid. The catalytic hydrogenation is preferably carried out in an inert solvent, such as a halogenated hydrocarbon, for example methylene chloride, or alternatively in water or a mixture of water and an organic solvent, such as an alcohol or dioxan, at approximately from 20° C. or 25° C., or alternatively while cooling or heating A hydroxy or mercapto group protected by a suitable acyl group, an organic silyl group or by optionally substituted 1-phenyl-lower alkyl is freed analogously to a correspondingly protected amino group. A hydroxy or mercapto group protected by 2,2-dichloroacetyl is freed, for example, by basic hydrolysis, and a hydroxy or mercapto group etherified by tert.-lower alkyl or by a 2-oxa- or 2-thia-aliphatic or -cycloaliphatic hydrocarbon radical is freed by acidolysis, for example by treatment with a mineral acid or a strong carboxylic acid, for example trifluoroacetic acid. Two hydroxy groups that are together protected by a preferably substituted methylene group, such as by lower alkylidene, for example isopropylidene, cycloalkylidene, for example cyclohexylidene, or benzylidene, can be freed by acid solvolysis, especially in the presence of a mineral acid or a strong organic acid.

If several protected functional groups are present, the protecting groups may, if desired, be so chosen that more than one such group can be removed at the same time, for example by acidolysis, such as by treatment with zinc and acetic acid, or by hydrogen and a hydrogenation catalyst, such as a palladium-on-carbon catalyst.

Salts of compounds of the formula I having at least one salt-forming group can be manufactured in a manner known per se. For example, salts of compounds of the formula I can be formed by treatment with metal compounds, such as alkali metal salts of suitable organic carboxylic acids, for example the sodium salt of α-ethylcaproic acid, or with inorganic alkali or alkaline earth metal compounds, such as corresponding hydroxides, carbonates and bicarbonates, such as sodium or potassium hydroxide, carbonate or bicarbonate or with corresponding calcium compounds or with ammonia or suitable organic amines, preferably stoichiometric amounts or a small excess of the salt-forming agent being used. Acid addition salts of compounds of the formula I that contain salt-forming basic groups are obtained in customary manner, for example by treatment with an acid or a suitable anion exchange reagent. Internal salts of compounds of the formula I that contain acidic and basic salt-forming groups can be formed, for example, by neutralising salts, such as acid addition salts, to the isoelectric point, for example with weak bases, or by treatment with liquid ion exchangers.

Salts can be converted in customary manner into the free compounds; metal and ammonium salts can be converted, for example, by treatment with suitable acids, and acid addition salts can be converted, for example, by treatment with a suitable basic agent.

Mixtures of isomers can be separated into the individual isomers in a manner known per se, for example by fractional crystallisation, chromatography etc, and racemates can be separated in a manner known per se into the optically active antipodes, for example with the formation of derivatives with optically active compounds and separation of the resulting diastereoisomeric mixtures.

Process variant (b)

Compounds of the formula I in which at least one of the radicals $R^1$, $R^2$, $R^4$ and $R^6$ is a radical of the formula Ia or Ib are obtained, for example, as follows: a compound of the formula VI

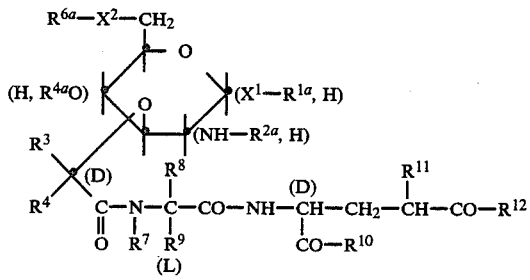

(VI)

in which a minimum of one and a maximum of three of the radicals, $R^{1a}$, $R^{2a}$, $R^{4a}$ and $R^{6a}$ is(are) hydrogen and the other(s) of the radicals $R^{1a}$, $R^{2a}$, $R^{4a}$ and $R^{6a}$ have the above-mentioned meanings of the radicals $R^1$, $R^2$, $R^4$ and $R^6$, respectively, and the other substituents have the meanings mentioned above, (hydroxy, amino or mercapto groups present in a compound of the formula VI, with the exception of the group(s) participating in the reaction, and, if necessary, other functional groups being in protected form), or a reactive derivative of a compound of the formula VI, is reacted in one step or in stages with a carboxylic acid of the formula VII

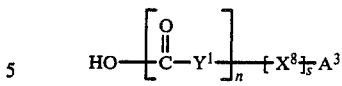

(VII)

in which $Y^1$ and n have the meanings mentioned above, $A^3$ has the above-mentioned meaning of $A^1$ or $A^2$, $X^8$ has the above-mentioned meaning of $X^3$ if $A^3$ represents $A^1$, or $X^8$ represents a carbonyl group if $A^3$ represents $A^2$, and s has the above-mentioned meaning of n if $A^3$ represents $A^1$, or s represents 1 if $A^3$ represents $A^2$, (functional groups present in a compound of the formula VII, with the exception of the group participating in the reaction, if necessary being in protected form), or with a reactive derivative of a compound of the formula VII, protecting groups present are removed and, if desired, a resulting compound of the formula I having at least one salt-forming group is converted into a salt.

Protecting groups for the mentioned functional groups are those described in process variant (a). The protection of carboxy groups in a compound of the formula VI is necessary, for example, if a mixture of the compounds of the formulae VI and VII is activated in situ, for example by the addition of dicyclohexyl carbodiimide.

A reactive derivative of a compound of the formula VI is, for example, a compound in which the hydroxy or amino group participating in the reaction is in reactive form, for example as described in process variant (a).

Functional groups in a compound of the formula VII the protection of which may be necessary, are, for example, amino, hydroxy, mercapto and other carboxy groups. Whether protection is necessary depends on the manner in which the reaction is carried out in each individual case (see below).

A reactive derivative of a carboxylic acid of the formula VII is a carboxylic acid dervative analogous to those described in process variant a) for compound IV. Protection of functional groups, such as, especially, amino groups, in a compound of the formula VII is generally necessary if this compound is reacted, for example, in the form of an activated ester, anhydride or amide with a compound of the formula VI.

The reaction of a compound of the formula VI with a compound of the formula VII can, as described above, also be carried out in stages. In that case the compound of the formula VI can first be reacted with a compound of the formula VIIa

(VIIa)

in which the substituents have the meanings mentioned above, (functional groups present in a compound of the formula VIIa, with the exception of the carboxy group participating in the reaction, if necessary being in protected form), or with a reactive acid derivative thereof, a protected group —$X^3$—H can be freed and the resulting intermediate of the formula VIa

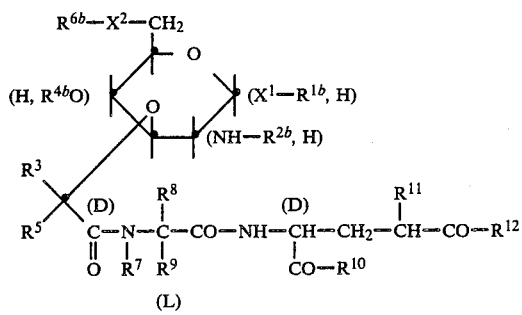

(VIa)

(L)

in which a minimum of one and a maximum of three of the radicals $R^{1b}$, $R^{2b}$, $R^{4b}$ and $R^{6b}$ is (are) a radical of the formula

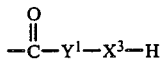

and the other(s) of the radicals $R^{1b}$, $R^{2b}$, $R^{4b}$ and $R^{6b}$ have the meanings given above for the radicals $R^1$, $R^2$, $R^4$ and $R^6$, respectively, and the other substituents have the meanings mentioned above, (hydroxy, amino or mercapto groups present in a compound of the formula VIa, with the exception of the group(s) participating in the reaction, and, if necessary, other functional groups being in protected form), or a reactive derivative of a compound of the formula VIa, can be reacted with a carboxylic acid of the formula $HO—A^1$ in which $A^1$ has the meaning mentioned above, functional groups present therein, with the exception of the carboxy group participating in the reaction, if necessary being in protected form), or with a reactive acid derivative thereof, protecting groups present can be removed and, if desired, a resulting compound of the formula I having at least one salt-forming group can be converted into a salt.

Alternatively, the compounds of the formula VI can first be reacted with a compound of the formula VIIb

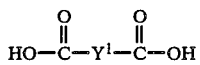   (VIIb)

in which $Y^1$ has the meaning mentioned above and in which the carboxy group on the right-hand side is, if necessary, (for example if the compound of the formula VIIb is asymmetrical) in protected form, or with a reactive acid derivative thereof, a protected carboxy group can be freed and then the resulting intermediate of the formula VIb

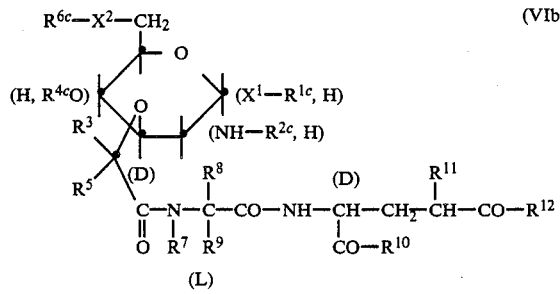   (VIb)

(L)

in which a minimum of one and a maximum of three of the radicals $R^{1c}$, $F^{2c}$, $R^{4c}$ and $R^{6c}$ is(are) the radical

in which $Y^1$ has the meaning mentioned above, and the other(s) of the radicals $R^{1c}$, $R^{2c}$, $R^{4c}$ and $R^{6c}$ have the above-mentioned meanings of the radicals $R^1$, $R^2$, $R^4$ and $R^6$, respectively, and the other substituents have the meanings mentioned above, (functional groups present in a compound of the formula VIb, with the exception of the group(s) participating in the reaction, if necessary being in protected form), or a reactive acid derivative of a compound of the formula VIb, can be reacted with a compound of the formula $H—A^2$ in which $A^2$ has the meaning mentioned above, (functional groups present therein, with the exception of the group participating in the reaction, if necessary being in protected form), or with a reactive derivative thereof, protecting groups present can be removed and, if desired, a resulting compound of the formula I having at least one salt-forming group can be converted into a salt.

The invention also relates to those embodiments of the process in which a compound of the formula VIa or VIb obtained in any manner is used as the starting material. The above-mentioned reactions are carried out in a manner analogous to that described in process variant (a).

Process variant (c)

Compounds of the formula I in which the radical $R^9$ is lower alkyl that is substituted by a radical, as defined above, of the formula Ic or Id, or their salts, are obtained, for example, as follows: a compound of the formula I in which the radical $R^9$ is hydroxy- or mercapto-substituted lower alkyl, (hydroxy, mercapto and amino groups present in a compound of the formula I and, if desired, other functional groups, with the exception of the functional group participating in the reaction, being in protected form), or a reactive derivative thereof, is reacted in one step or in stages with a carboxylic acid of the formula VIII

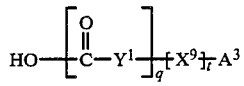   (VIII)

in which $Y^1$ and g have the meanings mentioned above, $A^3$ has the above-mentioned meaning of $A^1$ or $A^2$, $X^9$ has the above-mentioned meaning of $X^3$ if $A^3$ represents $A^1$, or $X^9$ represents a carbonyl group if $A^3$ represents $A^2$, and t has the above-mentioned meaning of g if $A^3$ represents $A^1$, or g represents 1 if $A^3$ represents $A^2$, (functional groups present in a compound of the formula VIII, with the exception of the group participating in the reaction, if necessary being in protected form), or with a reactive derivative of a compound of the formula VIII, protecting groups present are removed and, if desired, a resulting compound of the formula I having at least one salt-forming group is converted into a salt.

A reactive derivative of a compound of the formula I in which the radical $R^9$ is lower alkyl substituted by hydroxy is, for example, a halide, for example a chloride, bromide or iodide, which can be reacted, for example, with the caesium salt of a compound of the formula VIII.

As described above, the reaction can also be carried out in stages. In that case the compound of the formula I in which the radical $R^9$ is hydroxy- or mercapto-substituted lower alkyl (hydroxy, mercapto and amino groups present in a compound of the formula I and, if desired, other functional groups, with the exception of the functional group participating in the reaction, being in protected form), or a reactive derivative thereof, can first be reacted with a compound of the formula VIIa

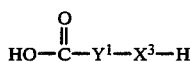
(VIIa)

in which the substituents have the meanings mentioned above, (functional groups present in a compound of the formula VIIa, with the exception of the carboxy group participating in the reaction, if necessary being in protected form), or with a reactive acid derivative thereof, a protected group $-X^3-H$ can be freed and the resulting intermediate of the formula IXa

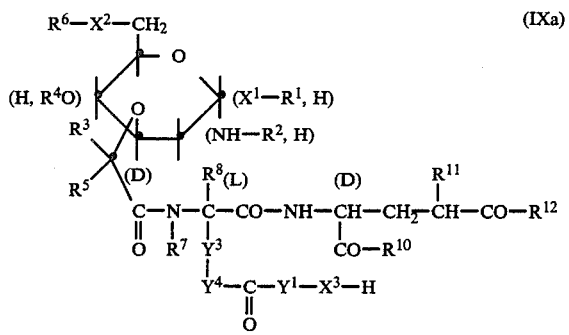
(IXa)

in which $Y^3$ represents lower alkylene and the other substituents have the meanings mentioned above, (functional groups present in a compound of the formula IXa, with the exception of the group participating in the reaction, if necessary being in protected form), or a reactive derivative of a compound of the formula IXa, can be reacted with a carboxylic acid of the formula $HO-A^1$ in which $A^1$ has the meaning mentioned above, (functional groups present therein, with the exception of the carboxy group participating in the reaction, if necessary being in protected form), or with a reactive acid derivative thereof, protecting groups present can be removed and, if desired, a resulting compound of the formula I having at least one salt-forming group can be converted into a salt.

Alternatively, the compound of the formula I in which the radical $R^9$ is hydroxy- or mercapto-substituted lower alkyl, (hydroxy, mercapto and amino groups present in a compound of the formula I and, if desired, other functional groups, with the exception of the functional group participating in the reaction, being in protected form), or a reactive derivative thereof, can first be reacted with a compound of the formula VIIb

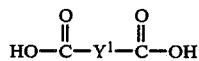
(VIIb)

in which $Y^1$ has the meaning mentioned above and in which the carboxy group on the right-hand side is, if necessary, (for example if the compound of the formula VIIb is asymmetrical) in protected form, or with a reactive acid derivative thereof, a protected carboxy group can be freed and then the resulting intermediate of the formula IXb

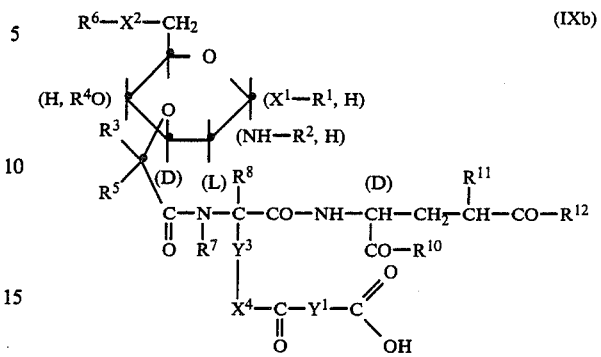
(IXb)

in which $Y^3$ represents lower alkylene and the other substituents have the meanings mentioned above, (functional groups present in a compound of the formula IXb, with the exception of the group participating in the reaction, if necessary being in protected form), or a reactive carboxylic acid derivative of a compound of the formula IXb, can be reacted with a compound of the formula $H-A^2$ in which $A^2$ has the meaning mentioned above, (functional groups present therein, with the exception of the group participating in the reaction, if necessary being in protected form), or with a reactive derivative thereof, protecting groups present can be removed and, if desired, a resulting compound of the formula I having at least one salt-forming group can be converted into a salt.

The invention also relates to those embodiments of the process in which a compound of the formula IXa or IXb obtained in any manner is used as the starting material. The above-mentioned reactions are carried out in a manner analogous to that described in process variant (a).

Process variant (d)

Compounds of the formula I in which the radical $R^9$ is lower alkyl that is substituted by a radical, as defined above, of the formula Ie or If, or their salts, are obtained, for example, as follows: a compound of the formula I in which the radical $R^9$ is lower alkyl substituted by carboxy, (carboxy groups present in a compound of the formula I and, if desired, other functional groups, with the exception of the functional group participating in the reaction, being in protected form), or a reactive carboxylic acid derivative thereof, is reacted in one step or in stages with a compound of the formula V

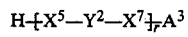
(V)

in which $X^5$ and $Y^2$ have the meanings mentioned above, $A^3$ has the above-mentioned meaning of $A^1$ or $A^2$, $X^7$ has the above-mentioned meaning of $X^6$ if $A^3$ represents $A^1$, or $X^7$ represents a carbonyl group if $A^3$ represents $A^2$, and r represents 1 if $A^3$ represents $A^1$, or r has the above-mentioned meaning of g if $A^3$ represents $A^2$, or with a reactive derivative of a compound of the formula V, protecting groups present are removed and, if desired, a resulting compound of the formula I having at least one salt-forming group is converted into a salt.

As described above, the reaction can also be carried out in stages. In that case the compound of the formula I in which the radical $R^9$ represents lower alkyl substituted by carboxy, (carboxy groups present in a compound of the formula I and, if desired, other functional groups, with the exception of the functional group participating in the reaction, being in protected form), or a reactive carboxylic acid derivative thereof, can first be reacted with a compound of the formula Va

in which the substituents have the meanings mentioned above, or with a derivative of this compound in which the group $H-X^5-$ is in reactive form, the group $X^6-H$ if necessary being protected by a protecting group, any protecting group present for the group $X^6-H$ can be removed and then the resulting intermediate of the formula IXc

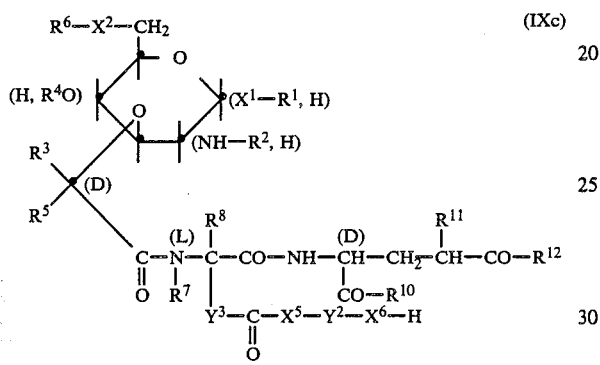

in which $Y^3$ represents lower alkylene and the other substituents have the meanings mentioned above, (functional groups present in a compound of the formula IXc, with the exception of the group participating in the reaction, if necessary being in protected form), or a reactive derivative of a compound of the formula IXc, can be reacted with a compound of the formula $H-A^2$ in which $A^2$ has the meaning mentioned above, (functional groups present therein, with the exception of the group participating in the reaction, if necessary being in protected form), or with a reactive derivative thereof, protecting groups present can be removed and, if desired, a resulting compound of the formula I having at least one salt-forming group can be converted into a salt.

The invention also relates to those embodiments of the process in which a compound of the formula IXb or IXc obtained in any manner is used as the starting material. The above-mentioned reactions are carried out in a manner analogous to that described in process variant (a).

Process variant (e)

A further process variant for the manufacture of a compound of the formula I is characterised in that, in a compound of the formula I in which the substituents have the meanings mentioned above, but in which at least one functional group is protected by a readily removable protecting group, this(these) protecting group(s) is(are) removed.

The protecting groups and the manner in which they are introduced and removed are described in process variant (a). Functional groups that may be protected are especially hydroxy, carboxy and amino groups, also mercapto groups and, optionally, sulpho groups. Any of these functional groups in a molecule of the formula I may be protected, especially the groups $-X^1-H$ in the 1-position of the sugar moiety, $-OH$ in the 4-position of the sugar moiety, $-X^2-H$ in the 6-position of the sugar moiety and free carboxy groups represented by or contained in the radicals $-COR^{10}$, $R^{11}$ and/or $-COR^{12}$.

Process variant (f)

A further process variant for the manufacture of a compound of the formula I is characterised in that a compound of the formula X

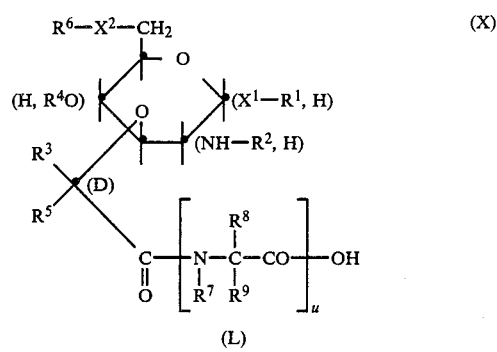

in which the index u has the meaning mentioned below and the substituents have the meanings mentioned above, (amino and other carboxy groups present in a compound of the formula X and, if necessary, other functional groups, with the exception of the group participating in the reaction, being in protected form), or a reactive acid derivative of a compound of the formula X, is reacted with a compound of the formula XI

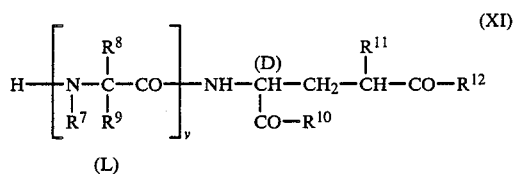

in which the index v represents 1 if, in a compound of the formula X, u represents 0, or in which v represents 0 if u represents 1, and the substituents have the meanings mentioned above, (carboxy and other amino groups present in a compound of the formula XI and, if necessary, other functional groups, with the exception of the group participating in the reaction, being in protected form), or with a reactive derivative of a compound of the formula XI, protecting groups present are removed and, if desired, a resulting compound of the formula I having at least one salt-forming group is converted into a salt.

The reaction is carried out analogously to process variant (a).

Process variant (g)

A further process variant for the manufacture of a compound of the formula I in which the sugar moiety is derived from D-glucose, $X^1$ and $X^2$ represent oxygen, $R^1$, $R^4$ and $R^6$ represent hydrogen and $R^2$ represents unsubstituted or substituted benzoyl, is characterised in that, in a furanose compound of the formula XII,

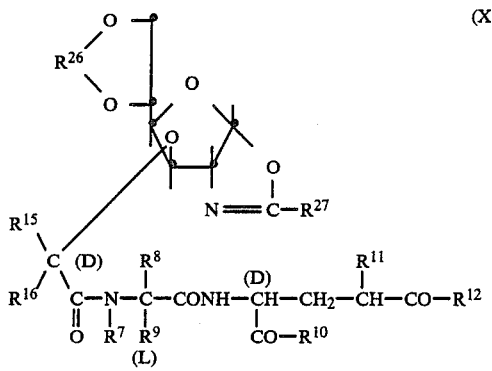

(XII)

in which $R^{26}$ represents a bivalent hydroxy-protecting group and $R^{27}$ represents unsubstituted or substituted phenyl, and the other substituents have the meanings given above, the oxazoline and the dioxolan rings are opened.

Bivalent hydroxy-protecting groups $R^{26}$ are especially optionally substituted alkylidene or cycloalkylidene groups. Alkylidene is especially lower alkylidene, such as isopropylidene, and cycloalkylidene is especially cyclopentylidene or cyclohexylidene. As substituents of the alkylidene radicals there may be mentioned especially aromatic radicals, for example phenyl radicals.

The substituents of substituted phenyl $R^{27}$ correspond to those of substituted benzoyl $R^2$.

The ring-opening operation is preferably carried out with dilute acid, best at a pH of from 2 to 4, for example 3, as a one-pot reaction in a manner known per se, for example with 50% acetic acid, an acidic ion exchanger, especially one having sulphonic acid groups, such as Amberlite IR-120 (a styrene resin having strongly acidic sulpho groups) or Dowex 50 (polystyrenesulphonic acids) or a strong inorganic or organic acid, such as hydrochloric acid, hydrobromic acid, sulphuric acid or a sulphonic acid, for example methanesulphonic acid, or a phenylsulphonic acid that is optionally substituted in the aromatic ring, such as p-toluenesulphonic acid, or trifluoroacetic acid. If the operation is carried out in the presence of water, a free hydroxy group is obtained in the 1-position of the glucopyranose.

The starting compound of the formula XII is obtained if the side chain is introduced into a compound of the formula XIII

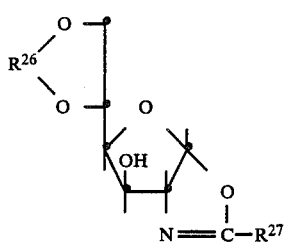

(XIII)

in which the substituents have the meanings mentioned above, in one or more stages, for example via a compound of the formula XIV

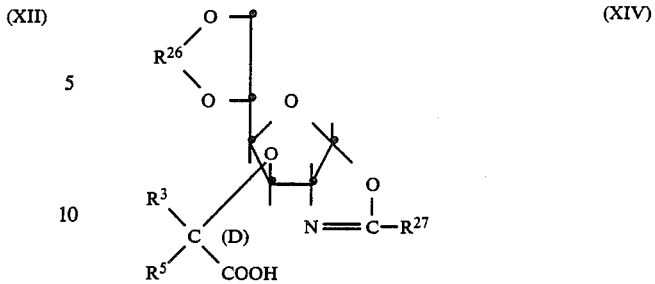

(XIV)

in which the substituents have the meanings given above.

Compounds of the formula XIV in which $R^3$ represents cycloalkyl and $R^5$ represents hydrogen, or in which $R^3$ and $R^5$ together represent lower alkylidene, cycloalkylidene or unsubstituted or substituted benzylidene, and their salts and reactive acid derivatives are novel and the present invention also relates to these as intermediates for the manufacture of the compounds of the formula I via the compounds of the formula XII. The reactive acid derivatives are analogous to those mentioned in process variant (a).

The intermediates of the formula XIV in which $R^3$ and $R^5$ together represent lower alkylidene, especially optionally lower alkyl-substituted methylene, or optionally substituted benzylidene are manufactured, for example, by reacting a compound of the formula XIII with diazophosphonoacetic acid triethyl ester in the presence of rhodium diacetate, and reacting the resulting compound of the formula XV

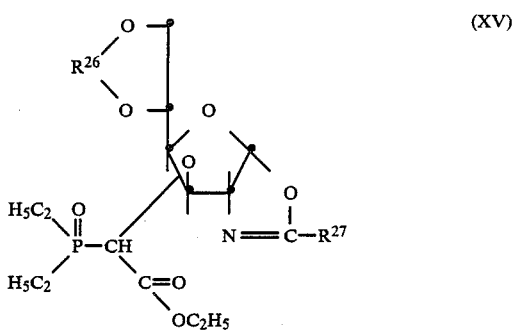

(XV)

in which the substituents have the meanings mentioned above, with the desired aldehyde, for example paraformaldehyde, for the manufacture of the methylene compound, on the lines of a Wittig-Horner reaction in the presence of a suitable base, for example diazabicycloundecene, and then hydrolysing the resulting carboxylic acid ethyl ester.

The compounds of the formula XIV in which $R^3$ represents cycloalkyl and $R^5$ represents hydrogen are obtained, for example, in a manner known per se by reacting a compound of the formula XIII with an α-cycloalkyl-α-bromoacetic acid derivative and a strong base, for example sodium hydride.

The processes described above, including the processes for removing protecting groups and the additional process steps are carried out in a manner known per se, for example in the presence or absence of solvents and diluents, if necessary in the presence of condensation agents or catalysts, at reduced or elevated temperature, for example in a temperature range of from approximately −20° C. to approximately 150° C., in a closed vessel and/or in an inert gas atmosphere, for example a nitrogen atmosphere.

Taking into account all the substituents in the molecule, there should be used, if necessary, for example if readily hydrolysable radicals are present, particularly mild reaction conditions, such as short reaction times, the use of mild acidic or basic agents in a low concentration, stoichiometric quantity ratios, and the choice of suitable catalysts, solvents, temperature and/or pressure conditions.

The invention also relates to those embodiments of the process in which a compound obtainable as intermediate at any stage of the process is used as starting material and the remaining process steps are carried out or the process is interrupted at any stage or a starting material is formed under the reaction conditions or is used in the form of a reactive derivative or salt. The starting materials used are preferably those which, according to the process, result in the compounds described above as being especially valuable.

The present invention also relates to novel starting materials and/or intermediates and to processes for their manufacture. The starting materials used and the reaction conditions chosen are preferably those which result in the compounds described in this Application as being especially preferred.

The pharmaceutically acceptable compounds of the present invention can be used, for example, for the manufacture of pharmaceutical preparations that contain a pharmaceutically effective amount, for example an amount sufficient for immunostimulation, of the active ingredient together or in admixture with a significant amount of inorganic or organic, solid or liquid pharmaceutically acceptable carriers.

The pharmaceutical preparations according to the invention are for enteral, such as oral or rectal, and parenteral, such as intraperitoneal, intramuscular or intravenous, administration to warm-blooded animals and contain the pharmacological active ingredient alone or together with a pharmaceutically acceptable carrier.

The carriers may be inorganic or organic and solid or liquid. For example, there are used tablets or gelatine capsules that contain the active ingredient together with diluents, for example lactose, dextrose, sucrose, mannitol, sorbitol, cellulose and/or glycerine, and/or lubricants, for example silica, talc, stearic acid or salts thereof, such as magnesium or calcium stearate, and/or polyethylene glycol. Tablets may also contain binders, for example magnesium aluminium silicate, starches, such as corn, wheat or rice starch, gelatine, methylcellulose, sodium carboxymethylcellulose and/or polyvinylpyrrolidone, and, if desired, disintegrators, for example starches, agar, alginic acid or a salt thereof, such as sodium alginate, and/or effervescent mixtures, or adsorbents, colourings, flavourings and sweeteners. The pharmacologically active compounds of the present invention can also be used in the form of parenterally administrable preparations or in the form of infusion solutions. Such solutions are preferably isotonic aqueous solutions or suspensions, it being possible, for example in the case of lyophilised preparations that contain the active ingredient alone or together with a carrier, for example mannitol, for these to be manufactured before use. The mentioned solutions or suspensions may contain viscosity-increasing substances, such as sodium carboxymethylcellulose, carboxymethylcellulose, dextran, polyvinylpyrrolidone or gelatine. The pharmaceutical preparations may be sterilised and/or contain adjuncts, for example preservatives, stabilisers, wetting agents and/or emulsifiers, solubilisers, salts for regulating the osmotic pressure and/or buffers. The present pharmaceutical preparations which, if desired, may contain other pharmacologically active ingredients, such as antibiotics, are manufactured in a manner known per se, for example by means of conventional mixing, granulating, confectioning, dissolving or lyophilising processes, and contain approximately from 0.001% to 99%, especially from approximately 0.01% to approximately 10%, more especially from 0.1% to 5%, of the active ingredient(s), an active ingredient concentration of less than 1% being especially suitable for preparations that are to be applied topically.

Pharmaceutical preparations according to the invention may be, for example, in dosage unit form, such as dragées, tablets, capsules, suppositories or ampoules.

Pharmaceutical preparations for oral administration can be obtained by combining the active ingredient with solid carriers, optionally granulating a resulting mixture and processing the mixture or granulate, if desired or necessary after the addition of suitable adjuncts, to form tablets or dragée cores. It is also possible to incorporate them into synthetic carriers that release the active ingredients, or allow them to diffuse, in a controlled manner.

The manufacture of injection preparations is carried out in customary manner under antimicrobial conditions, as is the filling into ampoules or phials and the sealing of the containers.

The dosage of the active ingredient depends on various factors, such as the mode of administration, species, the resistance of the organism and, to a decisive extent, on the nature of the disease to be treated. For example, the daily doses in the case of oral administration to warm-blooded animals weighing approximately 70 kg are approximately from 0.0001 to 0.1 g, a dose of less than 0.001 g being used especially to prevent the formation of metastases after the removal of the primary tumour.

The following Examples serve to illustrate the invention. Temperatures are given in degrees Centigrade. $R_f$ values are, unless otherwise indicated, determined on silica gel thin-layer plates (Merck, Darmstadt, Germany).

The composition of solvent mixtures is, unless otherwise indicated, given in parts by volume (v/v). In the case of optical rotation, the concentration, c, of the substance in the solvent (mixture) is given as a percentage (weight/volume).

Abbreviations

Boc=tert.-butoxycarbonyl
MeOH=methanol
PTFE=polytetrafluoroethylene
m.p.=melting point
THF=tetrahydrofuran

EXAMPLE 1

1.51 g (3.75 mmol) of 2-{2-[(2,6-dichlorophenyl)amino]-phenyl}-acetic acid 3-amino-2-hydroxypropylamide hydrochloride are dissolved in 50 ml of chloroform/methanol/water (70:30:5). 0.784 ml (5.63 mmol) of triethylamine, dissolved in 10 ml of the above mixture, is added dropwise thereto and, while stirring well at room temperature, 3.80 g (approximately 4.5 mmol) of the N-hydroxysuccinimide ester of N-acetylmuramyl-L-alanyl-D-isoglutamine (approximately 70% strength; additionally contains N-hydroxysuccinimide and dicyclohexylurea) are added in the form of a solid (three portions). After 1½ hours the suspension is filtered and the filtrate is concentrated to dryness by evaporation at 30°. The crude product, which is obtained in the form of a yellowish oil, is purified by being subjected twice to chromatography over silica gel 60 [particle size 0.063–0.200 mm (70–230 mesh ASTM)]in chloroform/methanol/water (70:30:5), first at a ratio of product to silica gel of 1:50 (15 ml fractions) and then of 1:90 (8 ml fractions). The pure fractions are collected. The residue remaining after the solvent has been concentrated by evaporation is taken up in 100 ml of a 1:1 mixture of water that has been distilled twice and tert.-butanol; the solution is passed through a millipore filter (PTFE, 0.2 μm) and lyophilised. N-acetylmuramyl-L-alanyl-D-isoglutamine-3-{2-[2-(2,6-dichlorophenylamino)-phenyl]acetylamino}-2-hydroxypropylamide. 1.94 H$_2$O is obtained in the form of a colourless powder; $[\alpha]_D^{20}=-24°$ (c=0.908; methanol), R$_f$=0.29 (chloroform:methanol:water=70:30:5), R$_f$=0.49 (acetonitrile:water=3:1), R$_f$=0.30 (n-butanol:acetic acid:water=75:7.5:21).

EXAMPLE 2

0.200 g (0.187 mmol) of N-acetylmuramyl-L-alanyl-D-isoglutaminyl-Ne-Boc-L-lysine-3-{2-[2-(2,6-dichloro-phenylamino)-phenyl]-acetylamino}-2-hydroxypropylamide is dissolved in 2 ml of 99% trifluoroacetic acid cooled to 0°. After standing for 5 minutes at the same temperature the solution is diluted with 20 ml of methylene chloride and the whole is concentrated to dryness by evaporation at room temperature (3 times); the oily residue is then taken up in 15 ml of absolute dioxan and the whole is lyophilised. The crude product (0.135 g) is purified by flash chromatography [W. Clark Still et al., J. Org. Chem. 43, 2923–2925 (1978)] over 50 g of silica gel 60 [particle size 0.040–0.063 mm (230–400 mesh ASTM)]in ethyl acetate/acetic acid/water/methanol (67:10:23:12, 5 ml fractions). The fractions containing the product are combined and the solvent is concentrated by evaporation. The residue is taken up in 10 ml of water that has been distilled twice and is filtered over 30 ml of a weakly basic ion exchanger that is in the form of an acetate (DOWEX 3, 20/50 mesh) in order to remove trifluoroacetic acid. The whole is then washed with 70 ml of water that has been distilled twice, the combined eluates are filtered through a millipore filter (0.2 μm), 20 ml of absolute dioxan are added and the whole is lyophilised. N-acetylmuramyl-L-alanyl-D-isoglutaminyl-L-lysine-3-{2-[2-(2,6-dichlorophenylamino)-phenyl]acetylamino}-2-hydroxypropylamide is obtained in the form of an extremely hygroscopic, colourless powder; $[\alpha]_D^{20}=+4$ (c=0.362; methanol), R$_f$=0.40 (ethyl acetate:acetic acid:water:methanol=67:10:23:12), R$_f$=0.20 (chloroform:methanol:water:acetic acid=70:40:10:5).

The starting material is obtained as follows: Stage 2.1: 0.62 ml (4.44 mmol) of triethylamine is added dropwise to a solution of 3.75 g (7.48 mmol) of N$^\alpha$-benzyloxycarbonyl-N$^\epsilon$-tert.-butoxycarbonyl-L-lysine-p-nitrophenyl ester and 1.80 g (4.44 mmol) of 2-[2-(2,6-dichlorophenylamino)-phenyl]-acetic acid 3-amino-2-hydroxypropylamide in 20 ml of dimethylformamide/chloroform (9:1) and the whole is allowed to react while stirring for 3 hours at 30°. The resulting suspension is concentrated by evaporation and the residue is triturated 4 times, each time with 50 ml of ethyl acetate which has been saturated with water. The insoluble material is filtered off and the combined ethyl acetate phases are dried after being washed several times with water. The residue remaining after concentration by evaporation is taken up in 5 ml of dimethylformamide, 50 ml of ethyl acetate are added and the product is precipitated by the addition in portions of 250 ml of petroleum ether and then the same procedure is repeated. N$^\alpha$-benzyloxycarbonyl-N$^\epsilon$-tert.-butoxycarbonyl-L-lysine-3-{2-[2-(2,6-dichlorophenylamino)-phenyl]-acetylamino}-2-hydroxypropylamide remains behind in the form of a colourless, amorphous powder; $[\alpha]_{546}^{20}{}_{nm}=-2°$ (c=0.478; dimethylformamide), R$_f$=0.86 (acetonitrile:water=3.1), R$_f$=0.95 (chloroform:methanol:water=70:30:5), R$_f$=0.44 (chloroform:isopropanol:acetic acid=70:8:2).

Stage 2.2: 1.80 g (2.46 mmol) of N$^\alpha$-benzyloxycarbonyl-N$^\epsilon$-tert.-butoxycarbonyl-L-lysine-3-{2-[2-(2,6-dichlorophenylamino)-phenyl]-acetylamino}-2-hydroxypropylamide are dissolved in 100 ml of 1,2-dimethoxyethane/dimethylformamide (9:1) and after the addition of 0.40 g of palladium-on-carbon (10%) the whole is treated for 1¼ hours with hydrogen. The catalyst is filtered off, the filtrate is concentrated by evaporation at 30° in a rotary evaporator and the residue is lyophilised after being taken up in 100 ml of dioxan/water (7:3). N$^\epsilon$-tert.-butoxycarbonyl-L-lysine-3-{2-[2-(2,6-dichlorophenylamino)-phenyl]-acetylamino}-2hydroxypropylamide is obtained in the form of a colourless powder which is immediately processed further; R$_f$=0.52 (acetonitrile:water=3:1), R$_f$=0.66 (ethyl acetate:n-butanol:pyridine:acetic acid:water=42:21:21:6:10).

Stage 2.3: 1.195 g (2 mmol) of N$^\epsilon$-Boc-L-lysine-3-{2-[2-(2,6-dichlorophenylamino)-phenyl-acetylamino}-2-hydroxypropylamide are dissolved in 50 ml of dimethylformamide/chloroform (4:1) and, while stirring at room temperature, 2.10 g (approximately 2.4 mmol) of the N-hydroxysuccinimide ester of N-acetylmuramyl-L-alanyl-D-isoglutamine (approximately 70% strength) are added thereto in the form of a solid in several portions. The pH value of the reaction solution is maintained at approximately 7 by the dropwise addition of a 5% solution of triethylamine in chloroform. After stirring for 16 hours, the resulting suspension is concentrated to dryness by evaporation at 30° and the residue is stirred well twice with 100 ml of ethyl acetate/water (1:1) each time. The insoluble material is filtered off with suction and dried (0.91 g) and subjected to flash chromatography (1:100, 5 ml fractions; 0.4 bar) over silica gel 60 (particle size 0.04–0.063 mm), first with chloroform and then with chloroform/methanol mixtures (95:5 to 60:40). The fractions containing the product are collected. The residue remaining after concentration of the solvent mixture by evaporation is taken up in 50 ml of absolute dioxan and lyophilised. N-acetylmuramyl-L-alanyl-D-dioxan isoglutaminyl-N$^\epsilon$-Boc-L-lysine-3-{2-[2-(2,6-dichlorophenyl)-aminophenyl]-acetylamino}-2-hydroxypropylamide is obtained in the form of a colourless powder; $[\alpha]_D^{20}=+15°$ (c=0.196; methanol), R$_f$=0.39 (chloroform:methanol:water=70:30:5), R$_f$=0.66 (ethyl acetate:n-butanol:pyridine:acetic acid:water=42:21:21:6:10).

EXAMPLE 3

0.250 g (0.40 mmol) of N-acetylmuramyl-L-alanyl-D-isoglutaminyl-L-lysine is dissolved in 10 ml of absolute dimethylformamide and, while stirring, firstly 0.056 ml (0.40 mmol) of triethylamine and then 0.237 g (0.60 mmol) of the N-hydroxysuccinimide ester of 2-[2-(2,6-dichlorophenylamino)-phenyl]-acetic acid are added. After standing for 8 hours at room temperature the solution is concentrated by evaporation under a high vacuum in a rotary evaporator. The residue (0.28 g) remaining after triturating several times with ethyl acetate is purified in customary manner by chromatography over 20 g of silica gel 60 (particle size 0.04–0.063 mm) in chloroform/methanol/water (70:30:5) (0.6 ml fractions). The pure fractions are collected and dissolved in 12 ml of water that has been distilled twice; the solution is filtered through a millipore filter (0.2 μm) and lyophilised. N-acetylmuramyl-L-alanyl-D-isoglutaminyl-N$^\epsilon$-{2-[2-(2,6-dichlorophenyl-amino)-phenyl]-acetyl}-L-lysine.3.3 H$_2$O is obtained in the form of a colourless powder; $[\alpha]_D^{20} = +26°$ (c=0.364; methanol), $R_f=0.17$ (chloroform:methanol:-water=70:30:5), $R_f=0.22$ (n-butanol:acetic acid:-water=75:7.5:21), $R_f=0.28$ (ethyl acetate:n-butanol:-pyridine:acetic acid:water=42:21:21:6:10).

EXAMPLE 4

Analogously to Example 3, from N-acetyldesmethylmuramyl-L-alanyl-D-isoglutaminyl-L-lysine, with excess N-hydroxysuccinimide ester of 2-[2-(2,6-dichlorophenylamino)-phenyl]-acetic acid, there is obtained N-acetyldesmethylmuramyl-L-alanyl-D-isoglutaminyl-N$^\epsilon$-{2-[2-(2,6-dichlorophenylamino)-phenyl]-acetyl}-L-lysine. 2.33 H$_2$O in the form of a colourless powder; $[\alpha]_D^{20} = +4°$ (c=0.569; methanol), $R_f=0.17$ (chloroform:methanol:water=70:30:5), $R_f=0.24$ (n-butanol:acetic acid:water=75:7.5:21), $R_f=0.29$ (ethyl acetate:n-butanol:pyridine:acetic acid:water=42:21:21:6:10).

EXAMPLE 5

300 mg (0.745 mmol) of 2-{2-[(2,6-dichlorophenyl)amino]-phenyl}-acetic acid 4-aminobutylamide hydrochloride, 385 mg (0.78 mmol) of N-acetyldesmethylmuramyl-L-alanyl-D-isoglutamine, 193 mg (1.67 mmol) of N-hydroxysuccinimide, 308 mg (1.49 mmol) of dicyclohexyl carbodiimide and 0.113 ml (0.82 mmol) of triethylamine are dissolved in 8 ml of absolute dimethylacetamide. The clear solution is left to stand for 15 hours at room temperature and is then evaporated to dryness under a high vacuum. The residue is partitioned twice between tetrahydrofuran and saturated aqueous NaCl solution and the organic phase is dried with Na$_2$SO$_4$ and concentrated by evaporation in vacuo. The residue is extracted three times with 30 ml of chloroform (hot) each time and once with hot dimethoxyethane/methanol (9:1). There is thus obtained N-acetyldesmethylmuramyl-L-alanyl-D-isoglutamine-4-{2-[2-(2,6-dichlorophenylamino)-phenyl]-acetylamino}-butylamide; m.p. 176°-178°; $R_f=0.375$ (chloroform:methanol=7:3), $[\alpha]_D^{20} = +17.2°$ (c=1.166; dimethylformamide).

The starting compound is obtained as follows:

Stage 5.1: 1,4-diaminobutane and 2-{2-[(2,6-dichlorophenyl)-amino]-phenyl}-acetic acid p-nitrophenyl ester are allowed to react for 8 hours at room temperature in methylene chloride/methanol (1:1). The reaction solution is then concentrated by evaporation in vacuo, the residue is taken up in tetrahydrofuran and the whole is extracted by shaking with 2N hydrochloric acid. The aqueous phase is extracted three times with diethyl ether to remove nitrophenol and is then saturated with NaCl and extracted with tetrahydrofuran. The organic phase is dried with Na$_2$SO$_4$ and concentrated by evaporation. The residue is triturated with diethyl ether and yields a crystalline powder which is recrystallised from ethyl acetate. 2-{2-[(2,6-dichlorophenyl)-amino]-phenyl}-acetic acid 4aminobutylamide hydrochloride is obtained in the form of its ethyl acetate solvate; m.p. 137°-140°; $R_f=0.177$ (CHCl$_3$:methanol:concentrated aqueous ammonia solution=10:10:0.1).

EXAMPLE 6

1.9 g (4.69 mmol) of 2-{2-[(2,6-dichlorophenyl)amino]-phenyl}-acetic acid 3-amino-2-hydroxypropylamide hydrochloride, 2.65 g (4.47 mmol) of N-propionyldesmethylmuramyl-L-alanyl-D-isoglutaminylalanine hydrate, 0.772 g (6.7 mmol) of N-hydroxysuccinimide, 2.31 g (11.2 mmol) of dicyclohexyl carbodiimide and 0.68 ml of triethylamine are dissolved in 40 ml of absolute dimethylacetamide and allowed to react for 15 hours at room temperature. The solution is then evaporated to dryness in vacuo, the residue is taken up in tetrahydrofuran, the solution is extracted four times by shaking with saturated aqueous NaCl solution, the organic phase is dried with Na$_2$SO$_4$ and the whole is evaporated to dryness. The resulting residue is extracted four times with 50 ml of hot chloroform each time and three times with 30 ml of a hot mixture of 9 parts tetrahydrofuran and 1 part methanol each time. The hot extracts are allowed to cool to room temperature; the substance which has partially dissolved crystallises out again and is filtered off with suction. Colourless crystals of N-propionyldesmethylmuramyl-L-alanyl-D-isoglutaminyl-L-alanine-3-{2-[2-(2,6-dichlorophenylamino)-phenyl]acetylamino}-2-hydroxypropylamide are thus obtained m.p. 192°-198°, $[\alpha]_D^{20} = +9°$ (c=1.12; dimethylformamide), $R_f=0.63$ (CHCl$_3$:MeOH=7:3).

The starting materials are obtained as follows:

Stage 6.1: A solution of 3.5 g (8.4 mmol) of 2-{2-[(2,6-dichlorophenyl)-amino]-phenyl}-acetic acid p-nitrophenyl ester is added dropwise to 2.6 g (28.8 mmol) of 1,3-diaminopropan-2-ol in 10 ml of MeOH. After 5 hours at room temperature the whole is evaporated to dryness in vacuo. The residue is taken up in tetrahydrofuran, 2N hydrochloric acid is added until a pH of 2 is reached and the aqueous phase is extracted three times with diethyl ether to remove nitrophenol. The aqueous phase is saturated with NaCl and the product is extracted with tetrahydrofuran. After drying with Na$_2$SO$_4$, concentrating by evaporation and triturating with diethyl ether, 2-{2-[(2,6-dichlorophenyl)-amino]-phenyl}-acetic acid 3-amino-2-hydroxypropylamide hydrochloride crystallises. The substance takes up water from the air and crystallises with approximately 1.5 mol of water. Decomposition point 92°, $R_f=0.3$ (acetonitrile:water=8:2 on thin-layer plates Opti-UPC$_{12}$, reverse phase, silica gel, Antec AG, CH-4431 Bennwil).

Stage 6.2: From α-benzyl-N-propionyldesmethylmuramyl-L-alanyl-D-isoglutaminyl-L-alanine benzyl ester, by means of catalytic hydrogenation with 10% palladium-on-carbon in tetrahydrofuran/water (4:1) and by lyophilising the aqueous solution which has been freed of catalyst and THF, there is obtained N-propionyldesmethylmuramyl-L-alanyl-D-isoglutaminyl-L-alanine hydrate in the form of a colourless powder; m.p. 141°–150°; $[\alpha]_D^{20} = -10°$ (c=0.943; $H_2O$), $R_f=0.36$ ($CH_3CN$:$H_2O$=3:1).

EXAMPLE 7

1 g (2.43 mmol) of N-{[2-(2,6-dichlorophenylamino)-phenyl]-acetyl}-L-aspartic acid and 0.6 g (3.16 mmol) of N-ethyl-N'-(dimethylaminopropyl)carbodiimide hydrochloride are allowed to react for 3 hours at room temperature in 25 ml of absolute dimethylformamide during which time the anhydride is formed. To this solution there are then added 1.58 g (3.16 mmol) of the sodium salt of N-acetyldesmethyl- muramyl-L-alanyl-D-isoglutamine and 0.37 ml of triethylamine. After a further 6 hours at room temperature the whole is evaporated to dryness in vacuo, the residue is taken up in water, the pH value is adjusted to 3 with 1N hydrochloric acid and the solution is extracted three times with ethyl acetate. After drying the organic phase with $Na_2SO_4$, concentration is carried out by evaporation in vacuo; the residue is dissolved in methanol/dimethoxyethane and reprecipitated. Colourless N-acetyl-6-O-{N-<[2-(2,6-dichlorophenylamino)-phenyl]-acetyl>-asparagin-$\beta$-yl}-desmethylmuramyl-L-alanyl-D-isoglutamine is obtained; m.p. 184° (decomposition), $[\alpha]_D^{20} = +21°$ (c=1.02; dimethylformamide), $R_f=0.266$ ($CHCl_3$:MeOH:$H_2O$=55:45:3).

The starting material is obtained as follows:

Stage 7.1: A solution of 3.9 g of the N-hydroxysuccinimide ester of 2-[2-(2,6-dichlorophenylamino)-phenyl]-acetic acid in dimethylformamide is added dropwise to 2.00 g of the disodium salt of L-aspartic acid in 10 ml of methanol/water (1:1). The solution is concentrated by evaporation in vacuo after one hour at room temperature, the residue is taken up in ethyl acetate and dilute hydrochloric acid and partitioned and the ethyl acetate phase is washed with water, dried with $Na_2SO_4$ and concentrated by evaporation. By trituration of the residue with diethyl ether, crystals of N-{[2-(2,6-dichlorophenylamino)-phenyl]-acetyl}-aspartic acid are obtained; m.p. 157°–160° (decomposition), $R_f=0.17$ ($CHCl_3$:MeOH=1:1).

EXAMPLE 8

3.41 g (7.21 mmol) of L-alanine-4-{2-[2-(2,6-dichlorophenylamino)-phenyl]-acetylamino}-butylamide hydrochloride are dissolved in 60 ml of absolute dimethylformamide, 0.83 ml (7.57 mmol) of N-methylmorpholine are added dropwise and, analogously to Example 1, 7.22 g (8.65 mmol) of N-acetyldesmethylmuramyl-L-alanine-D-isoglutamine N-hydroxysuccinimide ester (approximately 70% strength) are added thereto in three portions. After stirring overnight at room temperature, the whole is evaporated to dryness. The residue is purified firstly analogously to Example 1 by twice being subjected to chromatography over silica gel 60 (1:55; 11 ml fractions) in chloroform/methanol/water [70:30:5 (v/v)] and then by means of reverse phase chromatography (Opti $UPC_{12}$; 40–63 μm; 300:1). A gradient of acetonitrile:water=1:4 to 3:1 (v/v) is used as the eluant. The pure fractions are collected and the solvent is evaporated off. The residue is taken up in 100 ml of water that has been distilled twice and is dissolved by the addition of 20 ml of tert.-butanol. After filtration though a millipore filter (0.45μ) and lyophilisation, N-acetyldesmethylmuramyl-L-alanyl-D-isoglutaminyl-L-alanine-4-{2-[2-(2,6-dichlorophenylamino)-phenyl]-acetylamino}butylamide.2.3 $H_2O$ is obtained in the form of a colourless powder; $[\alpha]_D^{20}= +13.9°$ (c=0.505; dimethylformamide), $R_f=0.32$ (chloroform:methanol:water=70:30:5), $R_f=0.49$ (ethyl acetate:n-butanol:pyridine:acetic acid:water=42:21:21:6:10).

The starting material is obtained as follows:

Stage 8.1: 8.48 g (30 mmol) of N-benzyloxycarbonyl-L-alanine, 5.68 g (49.4 mmol) of N-hydroxysuccinimide and 15.30 g (38 mmol) of 2-{2-[(2,6-dichlorophenyl)amino]-phenyl}-acetic acid 4-aminobutylamide (for manufacture see Stage 5.1) are dissolved in 200 ml of absolute dimethylformamide, 4.19 ml (38 mmol) of N-methylmorpholine are added dropwise and, finally, 10.19 g (49.4 mmol) of dicyclohexyl carbodiimide are added. The whole is stirred at room temperature for 16 hours. The yellow suspension is evaporated to dryness in vacuo at 30° and the residue is taken up in 300 ml of ethyl acetate. The insoluble dicyclohexylurea is filtered off and the ethyl acetate phase is washed in customary manner first with saturated sodium bicarbonate solution (5×100 ml), then with 2N citric acid solution (4×100 ml) and then with water or saturated potassium chloride solution. After drying over sodium sulphate, the solution is concentrated to approximately 150 ml and, while stirring, a total of one liter of diethyl ether is added in portions. The crystals that have separated out are filtered off with suction after standing overnight at −10° C. A second fraction is obtained from the mother liquor. The two fractions are recrystallised together from 35 ml of chloroform/methanol/water (70:30:5) and 600 ml of diethyl ether/petroleum ether (1:1).

N-benzyloxycarbonyl-L-alanine-4-{2-[2-(2,6-dichlorophenylamino)-phenyl]-acetylamino}-butylamide is obtained in the form of a slightly yellowish powder; m.p. 146°–148°, $[\alpha]_D^{20}= -7.5$ (c=0.533; methanol), $R_f=0.50$ (chloroform:isopropanol:acetic acid=70:8:2), $R_f=0.78$ (chloroform:methanol:water=70:30:5).

Stage 8.2: 11.20 g (19.6 mmol) of N-benzyloxycarbonyl-L-alanine-4-{2-[2-(2,6-dichlorophenylamino)-phenyl]-acetylamino}-butylamide are dissolved in 200 ml of methanol, 1 g of palladium-on-carbon (10%) is added and the whole is hydrogenated, the pH value of the solution being kept constant at 4.5 by the addition of 1N hydrochloric acid in methanol. The catalyst is filtered off, the solution is extensively concentrated and, after the addition of 100 ml of absolute dioxan, lyophilised. L-alanine-4-{2-[2-(2,6-dichlorophenylamino)-phenyl]-acetylamino}-butylamide hydrochloride.0.9 dioxan is obtained in the form of a slightly yellowish powder; $R_f=0.43$ (chloroform:methanol:water=70:30:5), $R_f=0.30$ (ethyl acetate:nbutanol:pyridine:acetic acid:water=42:21:21:6:10).

EXAMPLE 9

By the methods described there are obtained N-benzoyldesmethylmuramyl-L-alanyl-D-isoglutaminyl-L-alanine-3-{2-[2-(2,6-dichlorophenylamino)-phenyl]acetylamino}-2-hydroxypropylamide, N-{2-[2-(2,6-dichlorophenylamino)-phenyl]-acetoxy}-acetylmuramyl-L-alanyl-D-isoglutamine, N-acetyl-1-desoxy-1$\beta$-{2-[2-(2,6-dichlorophenylamino)-phenyl]-acetyl}-thiodesmethylmuramyl-L-alanyl-D-isoglutamine methyl ester, N-acetyl-1-desoxy-1$\beta$-{2-[2-(2,6-dichlorophenylamino)-phenyl]-acetyl}-thiodesmethylmuramyl-L-alanyl-D-glutamine methyl ester, N-acetyl-1-desoxy-1$\beta${-2-[2-(2,6-dichlorophenylamino)-phenyl]-acetyl}-aminodesmethylmuramyl-L-alanyl-D-glutamine methyl ester, S-(N-acetyldesmethylmuramyl-L-alanyl-D-isoglutaminyl)-N-{2-[2-(2,6-dichlorophenylamino)-phenyl]-acetyl}-L-cysteine methyl ester, N-acetylmuramyl-L-alanyl-D-isoglutaminyl-L-alanine-3-{2-[2-(2,6-dichlorophenylamino)-phenyl]-acetylamino}-2-hydroxypropylamide, N-acetylmuramyl-L-alanyl-D-isoglutaminyl-L-alanine-2-{2-[2-(2,6-dichlorophenylamino)-phenyl]-acetoxy}-ethylamide, $N^\alpha$-(N-acetylmuramyl-L-alanyl-D-isoglutaminyl)-$N^\beta$-{2-[2-(2,6-dichlorophenylamino)-phenyl]-acetyl}-$\alpha,\beta$-diaminopropionic acid, $N^\alpha$-(N-acetylmuramyl-L-alanyl-D-isoglutaminyl-N-{2-[2-(2,6-dichlorophenylamino)-phenyl]-acetyl}-L-ornithine, N-(N-acetyldesmethylmuramyl-L-alanyl-D-isoglutaminyl)-S-2-{2-[2-(2,6-dichlorophenylamino)-phenylacetylamino}-ethyl-L-cysteine, N-(N-acetylmuramyl-L-alanyl-D-isoglutaminyl)ethyl-L-serine, N-(N-acetylmuramyl-L-alanyl-D-isoglutaminyl)-O-{ 2-[2-(2,6-dichlorophenylamino)-phenyl]acetoxy}-L-serine, N-acetylmuramyl-L-alanyl-D-(γ-methoxycarbonyl)-isoglutaminyl-L-alanine-3-{2-[2-(2,6-dichlorophenylamino)-phenyl]-acetylamino}-2-hydroxypropylamide, N-acetylmuramyl-L-alanyl-D-isoglutaminyl-L-alanine-3-{2-[1-(4-chlorobenzoyl)-5-methoxy-2-methylindol-3-yl]-acetylamino}-2-hydroxypropylamide, N-propionyldesmethylmuramyl-L-alanyl-D-glutamyl-($C_\alpha$)-methyl ester-($C_\gamma$)-L-alanine-3-{2-[1-(4-chlorobenzoyl)-5-methoxy-2-methylindol-3-yl]-acetylamino}-2-hydroxypropylamide, N-propionyldesmethylmuramyl-L-alanyl-D-isoglutaminyl-L-alanine-3-[2-(3-benzoylphenyl)propionylamino]-2-hydroxypropylamide, N-propionyldesmethylmuramyl-L-alanyl-D-isoglutaminyl-L-alanine-3-[2-(6-methoxynaphth-2-yl)-propionylamino]-2-hydroxypropylamide, N-propionyldesmethylmuramyl-L-alanyl-D-isoglutaminyl-L-alanine-3-[2-(4-isobutylphenyl)propionylamino]-2-hydroxypropylamide, N-propionyldesmethylmuramyl-L-alanyl-D-isoglutaminyl-L-alanine-3-{2-[3-chloro-4-(2,5-dihydro-1H-pyrrol-1-yl)-phenyl]propionylamino}-2-hydroxypropylamide and N-acetylmuramyl-L-alanyl-D-isoglutaminyl-L-alanine-3-{2-[3-chloro-4-(2,5-dihydro-1H-pyrrol-1-yl)-phenyl]propionylamino}-2-hydroxypropylamide.

EXAMPLE 10

In a manner analogous to that described in Example 1, 1.68 g (1.78 mmol) of the N-hydroxysuccinimide ester of N-acetylmuramyl-L-alanyl-D-isoglutamine (approximately 60% strength) are added to 0.70 g (1.49 mmol) of L-alanine-2-{2-[2-(2,6-dichlorophenylamino)-phenyl]acetoxy}-ethylamide acetate dissolved in 25 ml of dimethylformamide and the mixture is stirred for five hours at room temperature. The suspension is extensively concentrated at 30° under a high vacuum, absolute dioxan is added and the whole is lyophilised. The reddish residue is purified by chromatography over silica gel (1:50; 7 ml fractions) first in chloroform, then in chloroform/methanol mixtures (9:1, 85:15, 8:2; in each case 500 ml). The fractions containing the product are collected and purified over a second column in the manner described above, but in the system chloroform/methanol/water (70:30:5). The material contained in fractions 20–55 is collected, taken up in 5 ml of chloroform and precipitated by the addition in portions of 100 ml of diethyl ether, and then stirred for one hour at 0°. The precipitate is filtered off, dissolved in twice-distilled water and additions of tert.-butanol and dioxan, filtered through a millipore filter (0.2 μm) and lyophilised.

The compound mentioned in Example 9, N-acetylmuramyl-L-alanyl-D-isoglutaminyl-L-alanine-2-{2-[2-(2,6-dichlorophenylamino)-phenyl]-acetoxy}-ethylamide ($\alpha,\beta$-mixture), is obtained in the form of a colourless powder containing 1.6 mol of water and 2.3 mol of tert.-butanol; $[\alpha]_D^{20} = -22.7° \pm 4.4°$ (c=0.229; dioxan), $R_f$=0.33 (chloroform:methanol:water=70:30:5), $R_f$=0.43 (acetonitrile:water=3:1), $R_f$=0.57 (chloroform:methanol:water:acetic acid=75:27:5:0.5).

The starting material is obtained as follows:

Stage 10.1

8.00 g (25 mmol) of N-benzyloxycarbonyl-L-alanine-N-hydroxysuccinimide ester are dissolved in 40 ml of absolute tetrahydrofuran and, while stirring, 1.53 g (25 mmol) of 2-aminoethanol, dissolved in 10 ml of tetrahydrofuran, are added dropwise thereto. After stirring for 4 hours, the resulting white suspension is filtered, the precipitate is washed with diethyl ether and the filtrate is evaporated to dryness. The residue is partitioned several times between ethyl acetate diethyl ether/petroleum ether and water. The aqueous phase is extensively concentrated, taken up in 80 ml of water that has been distilled twice and lyophilised. N-benzyloxycarbonyl-L-alanine-ethanolamide is obtained in the form of a colourless powder; $[\alpha]_D^{20} = -14° \pm 1°$ (c=0.484; water), $R_f$=0.60 (chloroform:methanol:water=70:30:5), $R_f$=0.77 (ethyl acetate:n-butanol:pyridine:acetic acid:water=42:21:21:6:10).

Stage 10.2

1.97 g (14.6 mmol) of 1-hydroxybenzotriazole, 0.89 g (7.3 mmol) of dimethylaminopyridine and, finally, 1.66 g (8.03 mmol) of dicyclohexyl carbodiimide are added while stirring to 1.94 g (7.3 mmol) of N-benzyloxycarbonyl-L-alanine-ethanolamide and 2.81 g (7.3 mmol) of 2-[(2,6-dichlorophenyl)-N-benzylamino]phenylacetic acid, dissolved in 50 ml of absolute dimethylformamide. After stirring for 16 hours at room temperature, 500 ml of ethyl acetate are added to the suspension and, after stirring for a short time, the precipitate is filtered off. The filtrate is extracted three times in succession with 100 ml of water, saturated sodium bicarbonate solution, 2N citric acid solution and water each time. The residue remaining after evaporation of the solvent is purified by flash chromatography (0.65 bar; cf. Example 2) over 500 g of silica gel, first with chloroform (500 ml), then with chloroform/dimethoxyethane (95:5 and 9:1; 1 liter and 3 liters, respectively). The material contained in fractions 71–150 is collected. For further purification, a portion of the resulting material is purified by reverse-phase chromatography (Opti UPC$_{12}$; 40–63 μm, 1:300) using ethyl acetate as eluant. The pure fractions are collected, taken up in absolute dioxan and lyophilised. N-benzyloxycarbonyl-L-alanine-2-{2-[2(2,6-dichlorophenyl-N-benzylamino)-phenyl]-acetoxy}-ethylamide is obtained in the form of a colourless powder containing 0.36 mol of dioxan; $[\alpha]_{546}^{20}$ nm= +3.6° ±1.1° (c=0.926; dioxan), $R_f$=0.77 (acetonitrile:water=3:1), $R_f$=0.93 (chloroform:methanol:water=70:30:5).

Stage 10.3

After the addition of 0.1 g of palladium-on-carbon (10%), 1.00 g (1.58 mmol) of N-benzyloxycarbonyl-L-alanine-2-{2-[2-(2,6-dichlorophenyl-N-benzylamino)-phenyl]-acetoxy}-ethylamide, dissolved in 20 ml of acetic acid, is treated with hydrogen in customary manner. The catalyst is filtered off and the solution is lyophilised L-alanine-2-{2-[2-(2,6-dichlorophenylamino)-phenyl]-acetoxy}-ethylamide is obtained in the form of the acetate, $R_f=0.38$ (chloroform:methanol:water=70:30:5), $R_f=0.48$ (ethyl acetate:acetic acid:water:methanol=67:10:23:12).

EXAMPLE 11

3.30 g (4.94 mmol) of N-acetylmuramyl-L-alanyl-D-isoglutaminyl-L-ornithine and 2.73 g (6.93 mmol) of the N-hydroxysuccinimide ester of 2-[2-(2,6-dichlorophenylamino)-phenyl]-acetic acid are reacted in a manner analogous to that described in Example 3 and the crude material is purified by chromatography over silica gel (1:28, 5 ml fractions) in the system chloroform:methanol:water (70:30:5). The pure fractions are taken up in 60 ml of water that has been distilled twice, then filtered through a millipore filter (0.2 μm) and lyophilised. $N^\alpha$-(N-acetylmuramyl-L-alanyl-D-isoglutaminyl-$N^\delta$-{2-[2-(2,6-dichlorophenylamino)phenyl]-acetyl}-L-ornithine ($\alpha,\beta$-mixture) is obtained in the form of a colourless powder containing 3 mol of water; $[\alpha]_D^{20}=+20°\pm2.2°$ (c=0.480; methanol), $R_f=0.07$ (chloroform:methanol:water=70:30:5), $R_f=0.20$ (n-butanol:acetic acid:water=75:7.5:21), $R_f=0.27$ (ethyl acetate:n-butanol:pyridine:acetic acid:water=42:21:21:6:10).

The starting material is obtained as follows:
Stage 11.1

4.40 g (11.2 mmol) of $N^\delta$-benzyloxycarbonyl-L-ornithine benzyl ester hydrochloride, dissolved in 50 ml of dimethylformamide, are reacted in a manner analogous to that described in Example 1 with 14.73 g (14.55 mmol) of N-acetylmuramyl-L-alanyl-D-isoglutamine-N-hydroxysuccinimide ester (approximately 60% strength). After 4 hours, 300 ml of ethyl acetate are added dropwise thereto and the suspension is stirred for one hour at 0°. The precipitate is filtered off with suction and washed and then taken up again in 50 ml of dimethylformamide and precipitated (twice) as above. The insoluble material is filtered off, taken up in 35 ml of dimethylformamide and precipitated by the dropwise addition of 500 ml of water. After stirring for two hours at 0°, the precipitate is filtered off with suction, washed and dried; $R_f=0.37$ (n-butanol:acetic acid:water=75:7.5:21), $R_f=0.75$ (ethyl acetate:acetic acid:water:methanol=67:10:23:12).

The crude product, which still contains dicyclohexylurea, is dissolved in 100 ml of glacial acetic acid and, after the addition of 0.70 g of palladium-on-carbon (10%), is hydrogenated. The catalyst is filtered off with suction, the filtrate is concentrated by evaporation, 40 ml of absolute dioxan are added and the whole is lyophilised. The residue is suspended in 200 ml of water that has been distilled twice, the precipitate is filtered off with suction, the aqueous phase is extracted four times with 50 ml of ethyl acetate each time and re-extracted with a little water.

The combined aqueous phases are sterile-filtered (0.45 μm) and lyophilised. N-acetylmuramyl-L-alanyl-D-isoglutaminyl-L-ornithine ($\alpha,\beta$-mixture) is obtained in the form of a colourless powder; $[\alpha]_D^{20}=+13.9°\pm1.6°$ (c=0.624; methanol), $R_f=0.04$ (chloroform:methanol:water=70:30:5), $R_f=0.08$ (ethyl acetate:acetic acid:water:methanol=67:10:23:12).

EXAMPLE 12

4.50 g (8.71 mmol) of $N^\alpha$-benzyloxycarbonyl-$N^\beta$-{2[2-(2,6-dichlorophenylamino)-phenyl]-acetyl}-L-$\alpha,\beta$-diaminopropionic acid are dissolved in 75 ml of glacial acetic acid and hydrogenated in customary manner for 2½ hours. The catalyst is removed and the solution is concentrated under a high vacuum at 30° and then lyophilised; $R_f=0.39$ (n-butanol:acetic acid:water=75:7.5:21). 3.00 g (6.78 mmol) of the crude product, dissolved in 100 ml of absolute dimethylformamide, are reacted analogously to Stage 2.3 with 8.20 g (8.14 mmol) of N-acetylmuramyl-L-alanyl-D-isoglutamine-N-hydroxysuccinimide ester (approximately 60% strength). After stirring for 24 hours at room temperature, the suspension is evaporated to dryness under a high vacuum at 30° and the residue is partitioned between 250 ml of n-butanol and 250 ml of water. The upper phase is extracted twice more with 75 ml of water each time and re-extracted. The combined upper phases are extensively concentrated and the material is precipitated at reduced temperature by the addition in portions of 800 ml of diethyl ether/petroleum ether (1:1). The crude product is purified over silica gel (1:100; 15 ml fractions) in the system chloroform:methanol:water (70:30:5). The material contained in fractions 391-450 after first runnings of one liter is collected and dissolved in the above solvent mixture and the pH is adjusted to 7 by the careful addition of dilute sodium hydroxide solution. The solution is filtered through a millipore filter (PTFE; 0.2 μm) and extensively concentrated; absolute dioxan is added and the whole is lyophilised. The sodium salt of $N^\alpha$-(N-acetylmuramyl-L-alanyl-D-isoglutaminyl-$N^\beta$-{2-[2-(2,6-dichlorophenylamino)-phenyl]-acetyl}-L-$\alpha,\beta$-diaminopropionic acid ($\alpha,\beta$-mixture) is obtained in the form of a colourless powder containing 2.7 mol of water (cf. Example 9); $[\alpha]_D^{20}=+38.3°\pm1.3°$ (c=0.752; methanol), $R_f=0.15$ (n-butanol:acetic acid:water=75:7.5:21), $R_f=0.17$ (chloroform:methanol:water=70:30:5), $R_f=0.27$ (ethyl acetate:n-butanol:pyridine:acetic acid:water=42:21:21:6:10).

The starting material is obtained as follows:
Stage 12.1

4.00 g (11.8 mmol) of $N^\alpha$-benzyloxycarbonyl-L-$\alpha,\beta$-diaminopropionic acid, 1.19 g (11.8 mmol) of triethylamine and 6.02 g (15.3 mmol) of the N-hydroxysuccinimide ester of 2-[2-(2,6-dichlorophenylamino)phenyl]-acetic acid are suspended in 100 ml of a mixture of dimethoxyethane/acetonitrile/water (1:1:1) and stirred for 24 hours at room temperature. The residue remaining after evaporation of the solvent is taken up in 100 ml of ethyl acetate and extracted, first twice with 50 ml of dilute hydrochloric acid each time and then 3 times with 50 ml of cold-saturated sodium bicarbonate solution each time. Further purification is effected by means of alternating shaking: the ethyl acetate solution is extracted 8 times alternately with 50 ml of saturated sodium bicarbonate solution and with 50 ml of water, the corresponding extracts being collected separately. The aqueous phase which contains the product is acidified and the material formed is extracted with ethyl acetate. The organic phase is dried, concentrated to 50 ml and crystallised by the addition in portions of diethyl ether. $N^\alpha$-benzyloxycarbonyl-$N^\beta$-{2-[2-(2,6-dichlorophenylamino)-phenyl]-acetyl}-L-$\alpha,\beta$-diaminopropionic acid is obtained in the form of colourless needles; melting point 188.5°-190°, $[\alpha]_D^{20}=+6.2°\pm1.3°$ (c=0.764; methanol), $R_f=0.39$ (chloroform:methanol:water=70:30:5), $R_f=0.61$ (acetonitrile:water=3:1).

EXAMPLE 13

0.90 g (1.55 mmol) of $N^\epsilon$-{[2-(2,6-dichlorophenylamino)-phenyl]-acetyl}-L-thialysine benzyl ester hydrobromide and 0.217 g (2.1 mmol) of triethylamine, dissolved in 30 ml of dimethylformamide, are reacted analogously to Stage 2.3 at room temperature with 1.70 g (2.01 mmol) of N-acetylmuramyl-L-alanyl-D-isoglutamine-N-hydroxysuccinimide ester (approximately 70% strength). After stirring for 4 hours, the suspension is evaporated to dryness, the residue is suspended in 60 ml of boiled distilled water and, after stirring in an ice bath, the mixture is filtered. The residue is purified by chromatography over silica gel (1:100; 5 ml fractions) in the system chloroform/methanol/water (70:30:5). Fractions 24–44 contain pure material; fractions 45–80 on the other hand also contain oxidised material (=sulphoxide; cf. Example 14). By heating for a short time, the first fraction is dissolved in 80 ml of the solvent mixture used above and then filtered through a millipore filter (PTFE; 0.2 μm). The filtrate is concentrated to approximately 15 ml in a rotary evaporator, 40 ml of absolute dioxan are added thereto and the whole is lyophilised. N-(N-acetylmuramyl-L-alanyl-D-isoglutaminyl)-S-{2-(2,6-dichlorophenylamino)-phenylacetylamino}-ethyl-L-cysteine benzyl ester (60 ,β-mixture) is obtained in the form of a colourless powder containing 1.85 mol of water; $[\alpha]_D^{20} = +16° \pm 2°$ (c=0.497; dimethyl sulphoxide), $R_f$=0.59; sulphoxide: 0.50 (chloroform:methanol:water=70:30:5), $R_f$=0.73; sulphoxide: 0.63 (ethyl acetate:n-butanol:pyridine:acetic acid:water=42:21:21:6:10).

The starting material is obtained as follows:

Stage 13.1

1.27 g (3.00 mmol) of $N^\alpha$-benzyloxycarbonyl-L-thialysine benzyl ester hydrochloride and 0.34 g (3.3 mmol) of triethylamine, dissolved in 18 ml of absolute dimethylformamide, are reacted analogously to Example 3 with 1.53 g (3.9 mmol) of the N-hydroxysuccinimide ester of 2-[2-(2,6-dichlorophenylamino)phenyl]-acetic acid. After stirring for 2 hours at room temperature, the mixture is evaporated to dryness, the residue is taken up in 200 ml of ethyl acetate and the solution is extracted 8 times with 40 ml of water each time. The residue remaining after drying and evaporation of the solvent crystallises on standing at a reduced temperature (−10°). The crystal mass is suspended in 50 ml of methanol, stirred at reduced temperature for 30 minutes and then filtered off and dried. $N^\alpha$-benzyloxycarbonyl-$N^\epsilon$-{2-[(2,6-dichlorophenyl)-amino]-phenylacetyl}-L-thialysine benzyl ester is obtained in the form of colourless crystals; melting point 128°–129° $[\alpha]_D^{20} = -10° \pm 1.4°$ (c=0.714; methanol), $R_f$=0.80 (n-butanol:acetic acid:water=75:7.5:21).

Stage 13.2

1.40 g (2.1 mmol) of $N^\alpha$-benzyloxycarbonyl-$N^\epsilon$-{2-[(2,6-dichlorophenyl)-amino]-phenylacetyl}-L-thialysine benzyl ester are dissolved in 30 ml of dry ethyl acetate and, at reduced temperature while stirring and in the absence of moisture, 60 ml of hydrobromic acid in glacial acetic acid (33% strength) are added. After stirring for 2 hours at room temperature, the brownish reaction solution is cooled in an ice bath and the product is precipitated by the dropwise addition of 200 ml of diethyl ether/petroleum ether (1:1). After stirring at 0° for one hour in the absence of moisture, the precipitate is filtered off, washed well and dried at a high temperature over sodium hydroxide on a carrier (Merck). $N^\epsilon$-{[2-(2,6-dichlorophenylamino)-phenylacetyl}-L-thialysine benzyl ester hydrobromide is obtained in the form of a strongly hygroscopic powder which is immediately processed further; $R_f$=0.15 (chloroform:isopropanol:acetic acid=70:8:2), $R_f$=0.84 (chloroform:methanol:water=70:30:5).

EXAMPLE 14

The mixed fractions 45–80 obtained in Example 13 are dissolved in 4 ml of dimethyl sulphoxide/dimethylformamide (1:1) and, while stirring at reduced temperature, 0.14 ml of 30% hydrogen peroxide solution is added thereto. After standing for 2 days at room temperature, the reaction solution is concentrated to approximately 1 ml under a high vacuum; 10 ml of absolute dioxan are added and the whole is lyophilised. The residue is purified in customary manner by chromatography over silica gel (1:240; 4 ml fractions) in the system chloroform/methanol/water (70:30:5). The material contained in fractions 50–130 is collected and sterile-filtered analogously to Example 13. After the addition of absolute dioxan and lyophilisation, N-(N-acetylmuramyl-L-alanyl-D-isoglutaminyl)-S-{2-(2,6-dichlorophenylamino)-phenylacetylamino}-ethyl-L-cysteine benzyl ester sulphoxide (α,β-mixture) is obtained in the form of a colourless powder containing 2.73 ml of water; $[\alpha]_D^{20} = +11.5° \pm 2.3°$ (c=0.436; dimethyl sulphoxide).

EXAMPLE 15

While stirring at room temperature, 1.56 g (3.0 mmol) of L-alanine-3-{2-[1-benzoyl-5-methoxy-2-methylindol-3-yl]-acetylamino}-2-hydroxypropylamide hydrochloride, containing 0.49 mol of water, and 0.416 ml (3.0 mmol) of triethylamine are added to a solution of 2.79 g (3.2 mmol) of approximately 70% N-acetylmuramyl-L-alanyl-D-isoglutamine-N-hydroxysuccinimide ester in 65 ml of dimethylacetamide.

The resulting yellow solution is stirred for 18 hours at room temperature and then concentrated to dryness by evaporation under a high vacuum at 30°. The residue is taken up in 50 ml of methylene chloride and filtered, and 50 ml of diethyl ether are added to the filtrate. The crystals formed are filtered off with suction and then washed with diethyl ether. The crude product is purified by column chromatography over 370 g of silica gel (Type 60, Merck; 0.063–0.2 mm) in the system chloroform/methanol/water (70:30:5, 15 ml fractions).

Fractions 66–180 are combined and concentrated by evaporation under a high vacuum at 30°. The residue is crystallised twice from chloroform/methanol (1:1, 40 and 50 ml, respectively) with diethyl ether (150 and 100 ml respectively) and the resulting crystals are washed with diethyl ether. N-acetylmuramyl-L-alanyl-D-isoglutaminyl-L-alanine-3-{2-[1-benzoyl-5-methoxy-2-methylindol-3-yl]-acetylamino}-2-hydroxypropylamide (as an anomeric and diastereoisomeric mixture) is obtained in the form of light yellow-coloured crystals having a melting point of 204°–206° (decomposition). This product is dissolved in 200 ml of tert.-butanol/twice-distilled water (1:1) and the resulting solution is filtered through a millipore filter (Fluoropore, PTFE, 0.2 μm) and lyophilised under a high vacuum. The lyophilisate, which still contains tert.-butanol, is dissolved again in 100 ml of water that has been distilled twice, then filtered twice through a millipore filter (Nalgene S; 0.45 and 0.2 μm) and lyophilised again.

N-acetylmuramyl-L-alanyl-D-isoglutaminyl-L-alanine-3-{2-[1-benzoyl-5-methoxy-2-methylindol-3-yl]acetylamino}-2-hydroxypropylamide is obtained in the form of a colourless powder containing 3.05 mol of water; $[\alpha]_D^{20} = +23.5° \pm 2.0°$ (c=0.477; dimethylformamide), $R_f=0.60$ (chloroform:methanol=9:1), $R_f=0.58$ (chloroform:methanol:water=70:30:5).

The starting material is obtained as follows:

Stage 15.1

While stirring at room temperature, 4.54 g (22 mmol) of N,N-dicyclohexyl carbodiimide and 2.53 g (22 mmol) of N-hydroxysuccinimide are added to a solution of 7.156 g (20 mmol) of 1-(p-chlorobenzoyl)-5-methoxy-2-methyl-3-indolylacetic acid in 200 ml of absolute tetrahydrofuran. After 27 hours the N,N-dicyclohexylurea formed is filtered off and the filtrate is concentrated by evaporation at 30° under a high vacuum. The residue is recrystallised from 350 ml of ethyl acetate/isopropanol (1:1).

1-(p-chlorobenzoyl)-5-methoxy-2-methyl-3-indolylacetic acid N-hydroxysuccinimide ester is obtained in the form of colourless crystals having a melting point of 199°–200°; $R_f=0.85$ (chloroform:methanol=9:1).

Stage 15.2

While stirring at room temperature, a solution of 6.4 g (20 mmol) of N-benzyloxycarbonyl-L-alanine-N-hydroxysuccinimide ester in 200 ml of tetrahydrofuran is added dropwise over a period of 45 minutes to a solution of 7.6 g (60 mmol) of 1,3-diamino-2-propanol hydrochloride (Eastman, pract.) in 200 ml of water and the whole is stirred for 17 hours at room temperature. The solution is then concentrated to 50 ml and filtered and the filtrate is evaporated to dryness at 30° under a high vacuum. The resulting residue is purified by column chromatography over 2000 g of silica gel (Type 60, Merck; 0.063–0.2 mm) in the system chloroform/methanol (7:3, 20 ml fractions). Fractions 76–314 are combined and concentrated by evaporation at 30° under a high vacuum. The residue (white foam) crystallises from isopropanol/diethyl ether (1:7). N-benzyloxycarbonyl-L-alanine-3-amino-2-hydroxypropylamide hydrochloride is obtained in the form of colourless crystals that sinter at 96° and melt at from 114°–116°; $[\alpha]_D^{20} = -18.9° \pm 1.0°$ (c=0.975; water), $R_f=0.3$ (chloroform:methanol:water=70:30:5).

Stage 15.3

While stirring at room temperature, 1.39 ml (10.0 mmol) of triethylamine and then, over a period of 45 minutes, a solution of 4.40 g (9.67 mmol) of 1-(p-chlorobenzoyl)-5-methoxy-2-methyl-3-indolylacetic acid N-hydroxysuccinimide ester in 165 ml of tetrahydrofuran are added to a solution of 3.32 g (10.0 mmol) of N-benzyloxycarbonyl-L-alanine-3-amino-2-hydroxypropylamide hydrochloride in 165 ml of tetrahydrofuran/water (3:2). The resulting yellowish solution is stirred for 21 hours at room temperature and then concentrated to dryness by evaporation at 30° under a high vacuum. The solid residue is taken up in 300 ml of ethyl acetate and the resulting solution is extracted twice with 100 ml of 1N hydrochloric acid each time. The ethyl acetate phase is separated off, washed three times with 100 ml of 10% sodium bicarbonate solution each time and four times with 100 ml of water each time, dried over sodium sulphate and concentrated by evaporation at 30° under a high vacuum. After recrystallisation of the residue from 100 ml of ethyl acetate, pure N-benzyloxycarbonyl-L-alanine-3-{2-[1-p-chlorobenzoyl)-5-methoxy-2-methylindol-3-yl]-acetylamino}-2-hydroxypropylamide is obtained in the form of light yellowish crystals having a melting point of 142°–143° and containing 0.31 mol of water; $[\alpha]_D^{20} = +2.4° \pm 0.9°$ (c=1.058; dimethylformamide), $R_f=0.29$ (chloroform:methanol=9:1), $R_f=0.83$ (chloroform:methanol:water=70:30:5), $R_f=0.92$ (chloroform:methanol=7:3).

Stage 15.4

A solution of 4.65 g (7.26 mmol) of N-benzyloxycarbonyl-L-alanine-3-{2-[1-(p-chlorobenzoyl)-5-methoxy-2-methylindol-3-yl]-acetylamino}-2-hydroxypropylamide, containing 0.31 mol of water, in 150 ml of methanol is hydrogenated at room temperature and under normal pressure for 50 minutes using 1.0 g of 10% palladium-on-carbon as catalyst, the pH of the solution falling from an initial 7.3 to 3.5. The catalyst is then filtered off and the filtrate is concentrated by evaporation at 30° under a high vacuum. The residue is dissolved in 20 ml of water, 6.84 ml of 1N hydrochloric acid are added and the whole is again concentrated by evaporation. The resulting foam is stirred with 50 ml of diethyl ether for 1 hour at room temperature, and the crystals formed are filtered off with suction and washed with diethyl ether. L-alanine-3-{2-[1-benzoyl-5-methoxy-2-methylindol-3-yl]-acetylamino}-2-hydroxypropylamide hydrochloride, which, according to a chromatograph, is still slightly impure, is obtained in the form of colourless crystals that decompose at 160° and contain 0.49 mol of water. They are processed without being purified further; $[\alpha]_D^{20} = +11.1° \pm 1.0°$ (c=1.029; dimethylformamide), $R_f=0.57$ (chloroform:methanol:water=70:30:5), $R_f=0.46$ (chloroform:methanol=7:3).

EXAMPLE 16

In a manner analogous to that described in Example 15, from 2.43 g (2.8 mmol) of approximately 70% N-propionyldesmethylmuramyl-L-alanyl-D-glutamic acid ($C_\alpha$)-methyl ester ($C_\gamma$)-N-hydroxy-succinimide ester, 1 34 g (2.57 mmol) of L-alanine-3-{2-[1-benzoyl-5-methoxy-2-methylindol-3-yl]-acetylamino}-2-hydroxypropylamide hydrochloride, containing 0.49 mol of water, and 0.357 ml (2.57 mmol) of triethylamine, there is obtained N-propionyldesmethylmuramyl-L-alanyl-D-glutamic acid ($C_\alpha$)-methyl ester ($C_\gamma$)-L-alanine-3-{2-[1-benzoyl-5-methoxy-2-methylindol-3-yl]-acetylamino}-2-hydroxypropylamide (anomeric and diastereoisomeric mixture) in the form of a colourless powder containing 2.67 mol of water. The substance may also be crystallised from chloroform/methanol/diethyl ether (1:1:10); melting point 149°–151° (decomposition), $[\alpha]_D^{20} = -1.9° \pm 2.3°$ (c=0.427; water), $R_f=0.70$ (chloroform:methanol=7:3), $R_f=0.69$ (chloroform:methanol:water=70:30:5).

EXAMPLE 17

2.55 g (3.0 mmol; 1.175 mmol/g) of N-propionyldesmethylmuramyl-L-alanyl-D-isoglutamine-N-hydroxysuccinimide ester are suspended in 60 ml of dimethylacetamide. While stirring at room temperature, 1.127 g (2.71 mmol) of L-alanine-3-{d-2-[6-methoxy-2-naphthyl]-propionylamino}-2-hydroxypropylamide hydrochloride and 0.376 ml (2.71 mmol) of triethylamine are added to this suspension. After 22 hours the light yellow suspension is concentrated to dryness by evaporation at 30° under a high vacuum. The residue is taken up in 40 ml of methylene chloride and filtered and 40 ml of diethyl ether are added to the resulting clear solution. The colourless crystals formed are filtered off with suction and then washed with diethyl ether. The crude product is purified by column chromatography over 350 g of silica gel (Type 60, Merck; 0.063–0.2 mm) in the system chloroform/methanol/water (70:30:5); 10 ml fractions.

Fractions 64–90 are combined and concentrated by evaporation at 30° under a high vacuum. The residue crystallises from 40 ml of chloroform/methanol (1:1) after the addition of 200 ml of diethyl ether. The crystals are filtered off with suction, then washed with diethyl ether and dissolved in 40 ml of chloroform/methanol (1:1) and the resulting solution is filtered through a millipore filter (Fluoropore, PTFE; 0.2 μm). 200 ml of diethyl ether that has been filtered through a millipore filter (Fluoropore, PTFE; 0.2 μm) are added to the clear filtrate. The crystals formed are filtered off with suction and washed with diethyl ether that has been filtered through a millipore filter. Pure N-propionyldesmethylmuramyl-L-alanyl-D-isoglutaminyl-L-alanine-3-{d-2-[6-methoxy-2-naphthyl]-propionylamino}-2-hydroxypropylamide (anomeric and diastereoisomeric mixture) is obtained in the form of colourless crystals having a melting point of 182°–184° (decomposition) and containing 0.38 mol of water; $[\alpha]_D^{20} = +8.1° \pm 0.9°$ (c=1.105; dimethylformamide), $R_f$=0.27 (n-butanol:acetic acid:water=75:7.5:21), $R_f$=0.49 (chloroform:methanol=7:3), $R_f$=0.53 (chloroform:methanol:water=70:30:5)

The starting material is obtained as follows:

Stage 17.1

In a manner analogous to that described in Stage 15.1, from 5.75 g (25.0 mmol) of d-2-(6-methoxy-2-naphthyl)-propionic acid, 5.67 g (27.5 mmol) of N,N-dicyclohexyl carbodiimide and 3.16 g (27.5 mmol) of N-hydroxysuccinimide in 250 ml of tetrahydrofuran, there is obtained d-2-(6-methoxy-2-naphthyl)-propionic acid N-hydroxysuccinimide ester in the form of colourless crystals having a melting point of 128°–129° (from isopropanol); $[\alpha]_D^{20} = +70.0° \pm 1.0°$ (c=1.017; chloroform), $R_f$=0.54 (chloroform:methanol=95:5), $R_f$=0.88 (chloroform:methanol=9:1), $R_f$=0.92 (chloroform:methanol=7:3).

Stage 17.2

In a manner analogous to that described in Stage 15.3, from 3.32 g (10.0 mmol) of N-benzyloxycarbonyl-L-alanine-3-amino-2-hydroxypropylamide hydrochloride and 3.27 g (10.0 mmol) of d-2-(6-methoxy-2-naphthyl)-propionic acid N-hydroxysuccinimide ester, there is obtained N-benzyloxycarbonyl-L-alanine-3-{d-2-[6-methoxy-2-naphthyl]-propionylamino}-2-hydroxypropylamide in the form of colourless crystals having a melting point of 183°–184° (from ethyl acetate:isopropanol=1;1); $[\alpha]_D^{20} = +8.3° \pm 1.0°$ (c=0.963; methanol), $R_f$=0.63 (chloroform:ethanol=9:1), $R_f$=0.73 (chloroform:methanol=9:1), $R_f$=0.90 (chloroform:methanol=4:1).

Stage 17.3

In a manner analogous to that described in Stage 15.4, from 3.2 g (6.3 mmol) of N-benzyloxycarbonyl-L-alanine-3-{d-2-[6-methoxy-2-naphthyl]-propionylamino}-2-hydroxypropylamide by means of catalytic hydrogenation [1 g of palladium-on-carbon (10% palladium), 10 minutes, room temperature, normal pressure] in methanol, there is obtained L-alanine-3-{d-2-[6-methoxy-2-naphthyl]-propionylamino}-2-hydroxypropylamide hydrochloride in the form of colourless crystals that decompose at 102° and above and contain 0.29 mol of water; $[\alpha]_D^{20} = +32.3° \pm 0.9°$ (c=1.098; methanol), $R_f$=0.31 (chloroform:methanol=4:1), $R_f$=0.33 (chloroform:methanol=7:3), $R_f$=0.58 (chloroform:methanol:water=70:30:5).

EXAMPLE 18

In a manner analogous to that described in Example 17, from 2.34 g (2.75 mmol; 1.175 mmol/g) of N-propionyldesmethylmuramyl-L-alanyl-D-isoglutamine-N-hydroxysuccinimide ester, 0.965 g (2.45 mmol) of L-alanine-3-[2-(4-isobutylphenyl)-propionylamino]-2-hydroxypropylamide hydrochloride, containing 0.43 mol of water, and 0.340 ml (2.45 mmol) of triethylamine in 55 ml of dimethylacetamide, there is obtained N-propionyldesmethylmuramyl-L-alanyl-D-isoglutaminyl-L-alanine-3-[2-(4-isobutylphenyl)-propionylamino]-2-hydroxypropylamide (anomeric and diastereoisomeric mixture) in the form of colourless crystals having a melting point of 181°–183° (decomposition) and containing 0.43 mol of water; $[\alpha]_D^{20} = +13.0° \pm 1.0°$ (c=1.013; dimethylformamide), $R_f$=0.31 (n-butanol:acetic acid:water=75:7.5:21), $R_f$=0.51 (chloroform:methanol:water=70:30:5), $R_f$=0.53 (chloroform:methanol=7:3).

The starting material is obtained as follows:

Stage 18.1

In a manner analogous to that described in Stage 15.1, from 5.15 g (25.0 mmol) of 2-(4-isobutylphenyl)propionic acid, 5.67 g (27.5 mmol) of N,N-dicyclohexyl carbodiimide and 3.16 g (27.5 mmol) of N-hydroxysuccinimide in 250 ml of tetrahydrofuran, there is obtained 2-(4-isobutylphenyl)-propionic acid N-hydroxysuccinimide ester in the form of colourless crystals having a melting point of 96°–97° (from isopropanol); $R_f$=0.45 (chloroform:ethyl acetate=99:1), $R_f$=0.85 (chloroform:methanol=9:1).

Stage 18.2

In a manner analogous to that described in Stage 15.3, from 3.32 g (10.0 mmol) of N-benzyloxycarbonyl-L-alanine-3-amino-2-hydroxypropylamide hydrochloride and 3.04 g (10.0 mmol) of 2-(4-isobutylphenyl)-propionic acid N-hydroxysuccinimide ester, there is obtained N-benzyloxycarbonyl-L-alanine-3-[2-(4-isobutylphenyl)propionylamino]-2-hydroxypropylamide in the form of colourless crystals having a melting point of 127°–128°; $[\alpha]_D^{20} = -9.7° \pm 0.8°$ (c=1.218; methanol), $R_f$=0.50 (chloroform:ethanol=9:1), $R_f$=0.58 (chloroform:methanol=9:1), $R_f$=0.87 (chloroform:methanol=4:1), $R_f$=0.92 (chloroform:methanol:water=70:30:5).

Stage 18.3

In a manner analogous to that described in Stage 15.4, from 3.24 g (6.7 mmol) of N-benzyloxycarbonyl-L-alanine-3-[2-(4-isobutylphenyl)-propionylamino]-2-hydroxypropylamide by means of catalytic hydrogenation [1 g of palladium-on-carbon (10% palladium), 15 minutes, room temperature, normal pressure] in methanol at pH 7 (titration with 1N hydrochloric acid), there is obtained L-alanine-3-[2-(4-isobutylphenyl)propionylamino]-2-hydroxypropylamide hydrochloride in the form of colourless crystals which decompose at 88° and above (triturated with diethyl ether) and contain 0.43 mol of water; $[\alpha]_D^{20} = +8.3° \pm 0.9°$ (c=1.065; methanol), $R_f$=0.30 (chloroform:methanol=4:1), $R_f$=0.58 (chloroform:methanol:water=70:30:5).

EXAMPLE 19

500 mg (0.53 mmol) of N-propionyldesmethylmuramyl-L-alanyl-D-isoglutaminyl-L-alanine-3-{2-[2-(2,6-dichlorophenylamino)-phenyl]-acetylamino}-2-hydroxypropylamide (Example 6) are dissolved in 10 ml of pyridine to which 0.5 ml of acetic anhydride and 5 mg of 4-dimethylaminopyridine has been added. After 18 hours at room temperature 5 ml of MeOH are added and the mixture is evaporated to dryness in vacuo. The residue is extracted twice with 15 ml of ethyl acetate each time; the residue is dissolved in 20 ml of ethanol at 40° and cooled to room temperature and 20 ml of diethyl ether are added thereto. Colourless crystals of 1,4,6-tri-0-acetyl-N-propionyldesmethylmuramyl-L-alanyl-D-isoglutaminyl-L-alanine-3-{2-[2-(2,6-dichlorophenylamino)-phenyl]-acetylamino}-2-hydroxypropylamide having a melting point of 189°–190° are thus obtained; $[\alpha]_D^{20} = +1.8° \pm 1°$ (c=0.987; $CHCl_3$:MeOH=1:1), $R_f$=0.71 ($CHCl_3$:MeOH=8:2).

EXAMPLE 20

In a manner analogous to that described in Example 3, from 1.75 g (2.56 mmol) of N-acetylmuramyl-L-alanyl-D-isoglutaminyl-D,L-oxalysine, 1.01 g (3.07 mmol) of d-2-(6-methoxy-2-naphthyl)-propionic acid N-hydroxysuccinimide ester and 0.26 g (2.56 mmol) of triethylamine, dissolved in 30 ml of dimethylformamide/water (95:5), after chromatography over silica gel (1:60, 10 ml fractions) in the system chloroform/methanol/water (70:30:5), there is obtained N-(N-acetylmuramyl-L-alanyl-D-isoglutaminyl-O-[2-(6-methoxynaphth-2-yl)propionyl]-DL-serine ($\alpha,\beta$-mixture) in the form of a colourless powder containing 2.7 mol of water; $[\alpha]_D^{20} = +5.3° \pm 1.8°$ (c=0.562; water), $R_f$=0.07 (chloroform:methanol:water=70:30:5), $R_f$=0.19 (ethyl acetate:n-butanol:pyridine:acetic acid:water=42:21:21:6:10), $R_f$=0.45 (acetonitrile:water=3:1).

The starting material is obtained as follows:

Stage 20.1

1.05 g (3.71 mmol) of N$^\epsilon$-benzyloxycarbonyl-DL-oxalysine, 1.50 ml (14.43 mmol) of benzyl alcohol and 1.27 g (6.68 mmol) of p-toluenesulphonic acid are dissolved in 50 ml of benzene and the mixture is esterified for 4 hours at 85° by azeotropic removal of the water. The reaction solution is concentrated to approximately 5 ml and diluted with 100 ml of n-butanol/ethyl acetate (1:9) and the solution is extracted 6 times with 20 ml of water each time. The aqueous phase is re-extracted. The combined organic phases are concentrated to approximately 5 ml and, at reduced temperature, crystallised by the addition of 120 ml of ethyl acetate. The precipitate is filtered off. After drying, Ne-benzyloxycarbonyl-DL-oxalysine benzyl ester p-toluenesulphonate remains in the form of colourless crystals; melting point 126°–127°, $R_f$=0.49 (n-butanol:acetic acid:water=75:7.5:21), $R_f$=0.70 (ethyl acetate:n-butanol:pyridine:acetic acid:water=42:21:21:6:10).

Stage 20.2

1.05 g (2.92 mmol) of N$^\epsilon$-benzyloxycarbonyl-DL-oxalysine benzyl ester p-toluenesulphonate, 3.27 g (3.76 mmol) of N-acetylmuramyl-L-alanyl-D-isoglutamine-N-hydroxysuccinimide ester (approximately 70% strength) and 2.93 g (2.92 mmol) of triethylamine, dissolved in 30 ml of dimethylformamide, are reacted analogously to Stage 2.3 for 6 hours at room temperature. The suspension is diluted with 300 ml of ethyl acetate and, after stirring for one hour at 0°, the undissolved material is filtered off. At reduced temperature, the precipitate is suspended 6 times in 40 ml of cold water each time, the undissolved material is filtered off and the aqueous solution is extracted 6 times, each time with 20 ml of n-butanol saturated with water; $R_f$=0.55 (chloroform:isopropanol:acetic acid=70:8:2). The residue and the butanol extract are dissolved in 80 ml of glacial acetic acid and, after the addition of 0.45 g of palladium-on-carbon (10%), the whole is hydrogenated. The catalyst is filtered off and the filtrate is concentrated in vacuo at 30° and lyophilised. The resulting material is suspended in 60 ml of distilled water at reduced temperature and the undissolved material is filtered off. The filtrate is extracted several times with 10 ml of ethyl acetate each time, concentrated to half its volume, filtered through a millipore filter (0.45 μm) and lyophilised. N-acetylmuramyl-L-alanyl-D-isoglutaminyl-DL-oxalysine ($\alpha,\beta$-mixture) is obtained in the form of a colourless powder containing 1 mol of water; $[\alpha]_D^{20} = +20.5° \pm 2.6°$ (c=0.385; water), $R_f$=0.08 (acetonitrile:water=3:1).

EXAMPLE 21

In a manner analogous to that described in Example 19, by acetylating 0.52 g (0.608 mmol) of N-propionyl desmethylmuramyl-L-alanyl-D-isoglutaminyl-L-alanine-3-{d-2-[6-methoxy-2-naphthyl]-propionylamino}-2-hydroxypropylamide (see Example 17), containing 0.38 mol of water, with 345 μl (3.65 mmol) of acetic anhydride in 6 ml of absolute pyridine, with the addition of catalytic amounts of 4-dimethylaminopyridine (20 hours, room temperature), there is obtained (1α,β),4,6-tri-O-acetyl-N-propionyldesmethylmuramyl-L-alanyl-D-isoglutaminyl-L-alanine-3-[d-2-(6-methoxy-2-naphthyl]-propionylamino]-2-acetoxypropylamide (anomeric and diastereoisomeric mixture) in the form of a colourless powder (lyophilisate) containing 2.38 mol of water. Colourless crystals are obtained from chloroform/methanol/diethyl ether; melting point 207°–208° (decomposition), $[\alpha]_D^{20} = +22.6° \pm 2.1°$ (c=0.469; dimethylformamide, $R_f$=0.15 (chloroform:methanol=9:1), $R_f$=0.58 (chloroform:methanol=4:1), $R_f$=0.74 (chloroform:methanol:water=70:30:5).

EXAMPLE 22

In a manner analogous to that described in Example 7, from 3.0 g (3.52 mmol; 1.175 mmol/g) of N-propionyldesmethylmuramyl-L-alanyl-D-isoglutamine-N-hydroxysuccinimide ester and 1.40 g (3.42 mmol) of L-alanine-3-[2-(3-hydroxybenzylphenyl)-propionylamino]-2-hydroxypropylamide, containing 0.45 mol of water, in 70 ml of dimethylacetamide, there is obtained N-propionyldesmethylmuramyl-L-alanyl-D-isoglutaminyl-L-alanine-3-[2-(3-hydroxybenzylphenyl)-propionylamino]-2-hydroxypropylamide (anomeric and diastereoisomeric mixture) in the form of a colourless powder (lyophilisate) containing 2.71 mol of water. The substance crystallises from chloroform/methanol/diethyl ether (10:1:20) in the form of colourless crystals that decompose at 147° and above: $[\alpha]_D^{20} = -9.6° \pm 0.9°$ (c=1.121; water), $R_f$=0.37 (chloroform:methanol=7:3), $R_f$=0.48 (chloroform: methanol:water=70:30:5).

The starting material is obtained as follows:

Stage 22.1

In a manner analogous to that described in Stage 15.1, from 5.06 g (20.0 mmol) of 2-(3-benzoylphenyl)propionic acid, 4.54 g (22.0 mmol) of N,N-dicyclohexyl carbodiimide and 2.53 g (22.0 mmol) of N-hydroxysuccinimide in 250 ml of tetrahydrofuran there is obtained 2-(3-benzoylphenyl)-propionic acid N-hydroxysuccinimide ester in the form of colourless crystals having a melting point of 100°-101° (from ethanol); $R_f=0.55$ (chloroform:ethyl acetate=95:5).

Stage 22.2

In a manner analogous to that described in Stage 15.3, from 3.32 g (10.0 mmol) of N-benzyloxycarbonyl-L-alanine-3-amino-2-hydroxypropylamide hydrochloride and 3.51 g (10.0 mmol) of 2-(3-benzoylphenyl)-propionic acid N-hydroxysuccinimide ester, there is obtained N-benzyloxycarbonyl-L-alanine-3-[2-(3-benzoylphenyl)propionylamino]-2-hydroxypropylamide in the form of a colourless foam containing 0.22 mol of water; $[\alpha]_D^{20}=-7.9\pm0.8°$ (c=1.195; methanol), $R_f=0.45$ (chloroform:methanol=9:1), $R_f=0.94$ (chloroform:methanol=4:1).

Stage 22.3

In a manner analogous to that described in Stage 15.4, from 4.0 g (7.47 mmol) of N-benzyloxycarbonyl-L-alanine-3-[2-(3-benzoylphenyl)-propylamino]-2-hydroxypropylamide containing 0.22 mol of water, by means of catalytic hydrogenation [1 g of palladium-on-carbon (10% palladium), 40 minutes, room temperature, normal pressure] in methanol, after column chromatography of the free base (freed with 1N sodium hydroxide solution) over 400 g of silica gel (Type 60, Merck; 0.063-0.2 mm; chloroform/methanol/water system [70:30:5]), there is obtained L-alanine-3-[2-(3-hydroxybenzylphenyl)-propionylamino]-2-hydroxypropylamide in the form of colourless crystals having a melting point of 135°-136° (decomposition, from isopropanol:-diethyl ether=15:70) and containing 0.45 mol of water; $[\alpha]_D^{20}=+5.9\pm1.0°$ (c=1.018; methanol), $R_f=0.31$ (chloroform:methanol:water=70:30:5), $R_f=0.39$ (n-butanol:acetic acid:water=75:7.5:21).

EXAMPLE 23

0.5 g (0.5 mmol) of 2-phenyl-4,5-[3-O-{vin-1-yl-carbonyl-L-alanyl-D-isoglutaminyl-L-alanyl-4-(2-[2-(2,6-dichlorophenylamino)-phenyl]-acetylamino)-butylamido} -5,6-0-isopropylidene-D-glucofurano]-$\Delta^2$-oxazoline is dissolved in 15 ml of 50% acetic acid and hydrolysed for 6 hours at 50°. The whole is concentrated by evaporation in vacuo to form a resin. This resin is extracted three times with 20 ml of diethyl ether each time, the residue is dissolved in 15 ml of chloroform/methanol (1:9) at 30° and 40 ml of diethyl ether are added thereto. N-2-benzoylamino-2-desoxy-D-glucos-3-O-ylvin-1-yl-carbonyl-L-alanyl-D-isoglutaminyl-L-alanine-4-{2-[2-(2,6-dichlorophenylamino)-phenyl]-acetylamino}-butylamide is obtained in the form of a colourless, microcrystalline compound that melts at 155°-160°;$[\alpha]_D^{20}=+11.5°\pm1°$ (c=0.97; DMSO), $R_f=0.30$ (chloroform:methanol:-water=85:15:0.5).

The starting material is obtained as follows:

0.64 g (1.568 mmol) of 2-phenyl-4,5-[3,O-(1-ethoxycarbonylvinyl)-5,6-O-isopropylidene-D-glucofurano]-$\Delta^2$-oxazoline is dissolved in 10 ml of ethanol, 10 ml of dimethoxyethane and 0.872 ml of 2N sodium hydroxide solution. After 5 hours at room temperature the ester has been hydrolysed and the whole is concentrated by evaporation in vacuo, this being repeated 4 times with 20 ml of toluene each time. The residue is dried for 1 hour at 2.7 Pa (0.02 torr) and 45°, dissolved in 15 ml of absolute N,N-dimethylacetamide and, in succession, 0.46 g (2.22 mmol) of N,N'-dicyclohexyl carbodiimide, 0.3 g (2.22 mmol) of N-hydroxybenzotriazole and, at 0°, 0.133 ml (1.745 mmol) of trifluoroacetic acid are added thereto. After 30 minutes at room temperature, 1.29 g (1.745 mmol) of the trifluoroacetate of L-alanyl-D-isoglutaminyl-L-alanine-4-{2-[2-(2,6-dichlorophenylamino)-phenyl]acetylamino} -butylamide and 0.243 ml of triethylamine are added thereto. After 48 hours at room temperature, this mixture is evaporated to dryness in vacuo. The residue is taken up in 60 ml of ethyl acetate, the organic phase is extracted three times with 50 ml of 5% NaHCO$_3$ solution each time and twice with 50 ml of water each time and the aqueous phases are extracted twice with 50 ml of ethyl acetate each time. After drying the combined organic phases with Na$_2$SO$_4$ and concentration by evaporation in vacuo, a crude product is obtained. This product is extracted three times with 30 ml of hexane each time at 30°. The resin which remains is chromatographed over 100 g of silica gel (Merck, 0.04-0.63 mm) with methylene chloride/methanol (95:5). The fractions containing the desired compound ($R_f=0.62$ (CHCl$_3$:MeOH=85:15)) are concentrated by evaporation and recrystallised by adding a 10% solution in acetonitrile/methanol (1:1) with the same part by volume of diethyl ether. Colourless crystals of 2-phenyl-4,5-[3-O-{vin-1-yl-carbonyl-L-alanyl-D-isoglutaminyl-L-alanyl-4-(2-[2-(2,6-dichlorophenylamino) -phenyl]-acetylamino)-butylamido}5,6-O-isopropylidene-D-glucofurano]-$\Delta^2$-oxazoline having a melting point of 165°-170° (decomposition) are obtained; $[\alpha]_D^{20}=-15.1°\pm1°$ (c=0.962, CHCl$_3$:MeOH=1:1).

The peptide starting material is obtained in known manner by cleaving the tert.-butoxycarbonyl derivative with trifluoroacetic acid. Tert.-butoxycarbonyl-L-alanyl-D-isoglutaminyl-L-alanine-4-{2-[2-(2,6-dichlorophenylamino)-phenyl]-acetylamino}-butylamide, obtained in conventional manner, is a colourless compound having a melting point of 208°-212° (decomposition); $R_f=0.45$ (CHCl$_3$:methanol=9:1).

2-phenyl-4,5-[3,O-(1-ethoxycarbonylvinyl) -5,6-O-isopropylidene-D-glucofurano]-$\Delta^2$-oxazoline is obtained by the Wittig-Horner reaction of paraformaldehyde with 2-phenyl-4,5-[3,O-(ethoxycarbonyldiethylphosphonylmethyl)-5,6-O-isopropylidene-D-glucofurano]-$\Delta^2$-oxazoline and diazabicycloundecene in dimethoxyethane.

500 mg of the above-mentioned phosphonic ester of 2-phenyl-4,5-[3,O-(ethoxycarbonyldiethylphosphonylmethyl)-5,6-O-isopropylidene-D-glucofurano]-$\Delta^2$-oxazoline are dissolved in 5 ml of absolute dimethoxyethane and 85 mg of paraformaldehyde and 170 μl of diazabicycloundecene (DBU) are added thereto. A red suspension is obtained to which, after 3 hours at room temperature, a further 40 mg of paraformaldehyde and 40 μl of DBU are added. The mixture is then evaporated to dryness in vacuo and the residue is filtered over 20 g of silica gel (Merck, 0.04-0.63 mm) with chloroform. The fractions containing the product ($R_f=0.37$ (CHCl$_3$:ethyl acetate=95:5)) are concentrated by evaporation and the residue is recrystallised from ethanol. Colourless crystals of 2-phenyl-4,5-[3,O-(1-ethoxycarbonylvinyl)-5,6-O-isopropylidene-D-glucofurano]-$\Delta^2$-oxazoline having a melting point of 119°-120° are obtained; $[\alpha]_D^{20}=-17.5°\pm1°$ (c=0.892; CHCl$_3$).

The phosphonic ester used as starting material is obtained as follows:

34.5 g of diazophosphonoacetic acid triethyl ester and 0.36 g of rhodium diacetate are added to 20 g of 2-phenyl-4,5-[5,6-O-isopropylidene-D-glucofurano]-$\Delta^2$-oxazoline in 150 ml of toluene. The mixture is heated under a nitrogen atmosphere for 18 hours at 75°-80°, a further 11.5 g of diazo ester are added and the mixture is heated for a further 24 hours. The sugar has then reacted completely. The solution is concentrated by evaporation in vacuo, the residue is taken up in 250 ml of diethyl ether and the whole is extracted by shaking three times with 200 ml of water each time. The aqueous extracts are then extracted by shaking twice with 200 ml of diethyl ether each time. After drying the combined ether solutions over MgSO$_4$, the organic phase is concentrated by evaporation to form a yellow-brown oil. This crude product is chromatographed over 800 g of silica gel (Merck, 0.04–0.63 mm) with methylene chloride:acetone =95:5. 2-phenyl-4,5[3,O-(ethoxycarbonyldiethylphosphonylmethyl)-5,6-O-isopropylidene-D-glucofurano]-Δ$^2$-oxazoline is obtained as a diastereoisomeric mixture in the form of a yellow oil; R$_f$=0.39 and 0.50 (tertiary butyl methyl ether), $[\alpha]_D^{20}$= +21°±2.4° (c=0.424; CHCl$_3$).

EXAMPLE 24

In a manner analogous to that described in Example 17, from 1.19 g (1.4 mmol; 1.175 mmol/g) of N-propionyldesmethylmuramyl-L-alanyl-D-isoglutamine-N-hydroxysuccinimide ester, 0.72 g (1.4 mmol) of L-alanine-3-[2-(3-benzoylphenyl)-propionylamino]-2-hydroxypropylamide trifluoroacetate, containing 0.25 mol of water, and 195 μl (1.4 mmol) of triethylamine in 28 ml of dimethylacetamide, there is obtained N-propionyldesmethylmuramyl-L-alanyl-D-isoglutaminyl-L-alanine-3-[2-(3-benzoylphenyl)-propionylamino]-2-hydroxypropylamide in the form of a colourless powder containing 2.98 mol of water; $[\alpha]_D^{20}$= −11.5°±2.0° (c=0.494; water), R$_f$=0.32 (chloroform:methanol=7:3), R$_f$=0.39 (chloroform: methanol:water=70:30:5).

The starting material is obtained as follows:
Stage 24.1

In a manner analogous to that described in Stage 15.2, from 26.53 g (209 mmol) of 1,3-diamino-2-propanol hydrochloride (Eastman, pract.) and 20.0 g (69.8 mmol) of N-tert.-butoxycarbonyl-L-alanine-N-hydroxysuccinimide ester, after column chromatography over 1000 g of silica gel (Type 60, Merck; 0.063-0.2 mm), in the system chloroform/methanol/water (70:30:5), there is obtained N-tert.-butoxycarbonyl-L-alanine-3-amino-2-hydroxy-propylamide hydrochloride containing 0.56 mol of water; $[\alpha]_D^{20}$= −13.2 ±1.1° (c=0.945; methanol), R$_f$=0.26 (chloroform:methanol:water=70:30:5).

Stage 24.2

While stirring at room temperature, 0.68 ml (4.87 mmol) of triethylamine (density =0.728) and then, over a period of 45 minutes, a solution of 1.72 g (4.87 mmol) of 2-(3-benzoylphenyl)-propionic acid N-hydroxysuccinimide ester in 90 ml of tetrahydrofuran are added to a solution of 1.5 g (4.87 mmol) of N-tert.-butoxycarbonyl-L-alanine-3-amino-2-hydroxypropylamide hydrochloride, containing 0.56 mol of water, in 90 ml of tetrahydrofuran/water (3:2). After stirring for 24 hours at room temperature, the solution is concentrated to 30 ml and the aqueous phase is extracted twice with 200 ml of ethyl acetate each time. The ethyl acetate phases are washed once with 50 ml of 0.1N hydrochloric acid and once with 100 ml of 10% sodium bicarbonate solution and twice with 100 ml of water each time, dried over sodium sulphate and concentrated to dryness by evaporation under a high vacuum at 30°.

2.34 g of a colourless foam are obtained; this foam is dissolved in 50 ml of hot cyclohexane. After cooling the solution, the crude product separates off in the form of a colourless viscous oil. The solvent is decanted off. After decanting off again with 100 ml of pentane, the residue is dried under a high vacuum at 30°.

2.1 g of crude product are obtained in the form of a colourless foam which is purified by column chromatography over 200 g of silica gel (Type 60, Merck; 0.063-0.2 mm) in the system chloroform/methanol (9:1) (10 ml fractions). Fractions 33–50 are combined and concentrated by evaporation under a high vacuum at 30°. 2.05 g of a colourless foam are obtained; this foam is again purified by column chromatography (200 g of silica gel, Type 60, Merck, 0.063–0.2 mm, chloroform/methanol [9:1], 10 ml fractions).

Fractions 36–70 are in turn combined and concentrated by evaporation under a high vacuum at 30°.

2.0 g of a colourless foam are obtained; this foam is suspended in 50 ml of hot diethyl ether. After cooling, 100 ml of pentane are added to the resulting suspension and the mixture is stirred for 2 hours at room temperature. The resulting colourless crystals are filtered off with suction and washed with pentane. N-tert.-butoxycarbonyl-L-alanine-3-[2-(3-benzoylphenyl)propionylamino]-2-hydroxypropylamide is obtained in the form of colourless crystals having a melting point of 76°-78° (decomposition) and containing 0.21 mol of water; $[\alpha]_D^{20}$= −6.6 ±1.1° (c=0.870; methylene chloride), R$_f$=0.31 (chloroform:methanol=9:1), R$_f$=0.60 (chloroform:methanol=4:1), R$_f$=0.70 (chloroform:methanol =7:3).

Stage 24.3

While stirring at 0°, 6.4 ml (83.6 mmol) of trifluoroacetic acid (density=1.49) are added to a solution of 1.59 g (3.17 mmol) of N-tert.-butoxycarbonyl-L-alanine-3-[2-(3-benzoylphenyl)-propionylamino]-2-hydroxypropylamide, containing 0.21 mol of water, in 25 ml of absolute methylene chloride and the resulting solution is stirred for 3 hours at 0°. 60 ml of diethyl ether are then added to the clear colourless solution and the resulting suspension is stirred for 15 minutes at 0°. The colourless crystals formed are filtered off with suction and washed with diethyl ether. 1.45 g of crude product are obtained; this is suspended again in 50 ml of hot diethyl ether. After cooling, the suspension is stirred for a further one hour at room temperature and the resulting crystals are filtered off with suction and washed with diethyl ether. L-alanine-3-[2-(3-benzoylphenyl)-propionylamino]-2-hydroxypropylamide trifluoroacetate is obtained in the form of colourless crystals that decompose at 92° and above and contain 0.25 mol of water; $[\alpha]_D^{20}$= +10.9°±0.9° (c=1.054; methylene chloride), R$_f$=0.12 (chloroform:methanol=4:1), R$_f$=0.17 (chloroform:methanol=7:3), R$_f$=0.23 (chloroform:methanol:water=70:30:5).

EXAMPLE 25

In a manner analogous to that described in Example 17, from 1.7 g (2.0 mmol; 1.175 mmol/g) of N-propionyldesmethylmuramyl-L-alanyl-D-isoglutamine-N-hydroxysuccinimide ester, 0.70 g (1.61 mmol) of L-alanine-3-[2-(3-chloro-4-{pyrrol-1-yl}-phenyl)-propionylamino]-2-hydroxypropylamide hydrochloride, containing 0.35 mol of water, and 223.7 μl (1.61 mmol) of triethylamine in 45 ml of dimethylacetamide under an argon atmosphere, there is obtained N-propionyldesmethylmuramyl-L-alanyl-D-isoglutaminyl-L-alanine-3-[2-(3-chloro-4-{pyrrol-1-yl}-phenyl)-propionylamino]-2-hydroxypropylamide (anomeric and diastereoisomeric mixture) in the form of a colourless powder containing 2.67 mol of water; $[\alpha]_D^{20}=-10.4°\pm1.3°$ (c=0.779; water), $R_f=0.34$ (chloroform:methanol=7:3), $R_f=0.39$ (chloroform:methanol:water=70:30:5).

The starting material is obtained as follows:

Stage 25.1

In a manner analogous to that described in Stage 15.1, from 5.0 g (20.0 mmol) of 2-(3-chloro-4-{pyrrol-1-yl}-phenyl)-propionic acid, 4.54 g (22.0 mmol) of N,N-dicyclohexyl carbodiimide and 2.53 g (22.0 mmol) of N-hydroxysuccinimide in 200 ml of tetrahydrofuran under an argon atmosphere, there is obtained 2-(3-chloro-4-{pyrrol-1-yl}-phenyl)-propionic acid N-hydroxysuccinimide ester; melting point 116°–117° (from isopropanol:ethyl acetate =8:1), $R_f=0.51$ (chloroform:ethyl acetate =9:1), $R_f=0.82$ (chloroform:ethanol =9:1).

Stage 25.2

In a manner analogous to that described in Stage 24.2, from 1.5 g (4.87 mmol) of N-tert.-butoxycarbonyl-L-alanine-3-amino-2-hydroxypropylamide hydrochloride containing 0.56 mol of water, 0.68 ml (4.87 mmol) of triethylamine (density =0.728) and 1.68 g (4.87 mmol) of 2-(3-chloro-4-{pyrrol-1-yl}-phenyl)-propionic acid N-hydroxysuccinimide ester in a total of 180 ml of tetrahydrofuran/water (5:1) under an argon atmosphere, there is obtained N-tert.-butoxycarbonyl-L-alanine-3-[2-(3-chloro-4-{pyrrol-1-yl}-phenyl)-propionylamino]-2-hydroxypropylamide in the form of colourless crystals having a melting point of 75°–77° (decomposition; from cyclohexane:diethyl ether:petroleum ether=5:4:10) and containing 0.42 mol of water; $[\alpha]_D^{20}=-7.1\pm1.1°$(c=0.928; methylene chloride), $R_f=0.63$ (chloroform:methanol =4:1), $R_f=0.72$ (chloroform:methanol:water=70:30:5).

Stage 25.3

At 0°, 25 ml of a solution of approximately 5N hydrochloric acid in ethyl acetate are added to a solution of 1.078 g (2.15 mmol) of N-tert.-butoxycarbonyl-L-alanine-3-[2-(3-chloro-4-{pyrrol-1-yl}-phenyl)-propionylamino]-2-hydroxypropylamide, containing 0.42 mol of water, in 25 ml of ethyl acetate and the whole is then stirred for 2 hours at 0° under an argon atmosphere.

50 ml of diethyl ether are then added to the yellowish solution and the resulting suspension is stirred for 15 minutes at 0° until crystallisation takes place. The crystals are filtered off with suction and washed with diethyl ether. 0.83 g of crude product, which is then suspended in 60 ml of ethyl acetate/diethyl ether (1:2), is obtained. The suspension is stirred for 2 hours at room temperature until crystallisation is complete and then the crystals are filtered off with suction and washed with diethyl ether.

L-alanine-3-[2-(3-chloro-4-{pyrrol-1-yl}-phenyl)-propionylamino]-2-hydroxypropylamide hydrochloride is obtained in the form of colourless crystals that decompose at 179° and above and contain 0.35 mol of water; $[\alpha]_D^{20}=+6.9°\pm3.0°$ (c=0.334; methanol), $R_f=0.32$ (chloroform:methanol:water=70:30:5).

EXAMPLE 26

While stirring at room temperature, 0.638 g (4.0 mmol) of 1-hydroxybenzotriazole (contains approximately 10% water), 0.244 g (2.0 mmol) of 4-dimethylaminopyridine, 1.493 g (4.0 mmol) of 2-[4,5-di-(4-methoxyphenyl)-thiazol-2-ylthio]-ethanol and 0.825 g (4.0 mmol) of N,N-dicyclohexyl carbodiimide are added in succession to a solution of 1.148 g (2.0 mmol) of N-propionyldesmethylmuramyl-L-alanyl-D-isoglutaminyl-L-alanine, containing 0.59 mol of water, in 25 ml of dimethylformamide.

The initially clear, colourless solution is stirred for 22 hours at room temperature. The resulting suspension is then filtered and the filtrate is concentrated to dryness by evaporation under a high vacuum at 30°.

The crude product is obtained in the form of a yellow-coloured foam which is purified by column chromatography over 400 g of silica gel (Type 60, Merck; 0.063–0.2 mm) in the system chloroform/methanol/water (70:30:5) (10 ml fractions).

Fractions 47–74 are combined and concentrated by evaporation under a high vacuum at 30°. The residue (0.9 g) is dissolved in chloroform/methanol (15:2) and 50 ml of diethyl ether are added to the resulting solution. The suspension is stirred for 30 minutes at room temperature until crystallisation is complete and the crystals are then filtered off with suction and washed with diethyl ether. The crystals are then suspended in 20 ml of hot tetrahydrofuran, the resulting suspension is cooled to room temperature, 10 ml of diethyl ether are added and the whole is stirred for 15 minutes until crystallisation is complete. The crystals are filtered off with suction and washed with diethyl ether. 0.62 g of colourless crystals having a melting point of 164°–166 (decomposition) is obtained. These crystals are dissolved in 100 ml of twice-distilled water/tert.-butanol (1:1) while heating gently. The colourless solution is filtered through a millipore filter (Fluoropore, PTFE, 0.2μm) and lyophilised under a high vacuum.

In order to remove the residual tert.-butanol, the lyophilisate is taken up again in 80 ml of twice-distilled water and lyophilised once more.

N-propionyldesmethylmuramyl-L-alanyl-D-isoglutaminyl-L-alanine-2-[4,5-di-(4-methoxyphenyl)-thiazol-2-ylthio]-ethyl ester (anomeric mixture) is obtained in the form of a colourless powder containing 1.99 mol of water; $[\alpha]_D^{20}=-3.0°\pm1.9°$ (c=0.537; methanol), $R_f=0.47$ (chloroform:methanol=7:3), $R_f=0.57$ (chloroform:methanol:water =70:30:5). The compound decomposes in aqueous solution (room temperature, 16 hours: partial decomposition).

EXAMPLE 27

In a manner analogous to that described in Example 23, 2-phenyl-4,5-[3-O-{2-n-propyl-(E,Z)-vin-1-yl-carbonyl-L-alanyl-D-isoglutaminyl-L-alanyl-4-(2-<2-(2,6-dichlorophenylamino)-phenyl>-acetylamino)-butylamido}-5,6-O-isopropylidene-D-glucofurano]-Δ²-oxazoline is hydrolysed with 50% acetic acid and, after analogous working-up, N-benzoyl-(α,β)-glucosaminyl-3-O-(2-n-propyl-(E,Z)-vin-1-ylcarbonyl-L-alanyl-D-isoglutaminyl-L-alanine-4-{2-[2-(2,6-dichlorophenylamino)phenyl]-acetylamino}-butylamide containing 1 mol of water of crystallisation is obtained; melting point 152°–157°, $[\alpha]_D^{20}=+9.7°\pm1.1°$ (c=0.879; DMSO), $R_f=0.39$ (chloroform:methanol:water=85:15:1).

The starting material is obtained analogously to Example 23 in the form of an E,Z-mixture; melting point 176°–179°, $[\alpha]_D^{20}=-8.5°\pm1.1°$ (c=0.944; CHCl₃:MeOH=1:1), $R_f$ (isomer A)=0.35 (CHCl₃:MeOH=9:1), $R_f$ (isomer B)=0.32 (CHCl₃:MeOH=9:1).

In a manner analogous to that described in Example 23, by a Wittig-Horner reaction, 2-phenyl-4,5-[3-O-(1- ethoxycarbonyl-2-n-propyl-(E,Z)-vin-1-yl-5,6-O-isopropylidene-D-glucofurano]-$\Delta^2$-oxazoline is obtained in the form of a colourless oil from the corresponding phosphonic ester with n-butyraldehyde; $R_f=0.38$ (CHCl$_3$), $[\alpha]_D^{20}=-4.1°\pm0.5°$ (c=2.15; CH/Cl$_3$).

EXAMPLE 28

In a manner analogous to that described in Example 23, 0.5 g of 2-phenyl-4,5-[3-O-{2-p-chlorophenyl-(E,Z)-vin-1-ylcarbonyl-L-alanyl-D-isoglutaminyl-L-alanyl-4-(2-<- (2,6-dichlorophenylamino)-phenyl>-acetylamino)butylamido}-5,6-O-isopropylidene-D-glucofurano]-$\Delta^2$-oxazoline is hydrolysed in 20 ml of 50% acetic acid for 6 hours at 40°. The whole is then evaporated to dryness in vacuo and the residue is triturated with 30 ml of diethyl ether and chromatographed over 25 g of silica gel (Merck; 0.04–0.63 mm) using the elution mixture methylene chloride/methanol/water (90:10:0.1). The fractions having $R_f=0.39$ (CHCl$_3$:MeOH:H$_2$O =85:15:1) are concentrated by evaporation. The residue is dissolved in acetonitrile/methanol (7:3) and diethyl ether is added until the solution becomes cloudy. Crystals of N-benzoylglucosaminyl-3-O-(2-p-chlorophenyl-(E, Z)-vin-1-ylcarbonyl-L-alanyl-D-isoglutaminyl-L-alanine-4-{2-[2-(2,6-dichlorophenylamino)phenyl]-acetylamino}-butylamide containing 1.2 mol of water of crystallisation are obtained; melting point 157°–161°, $[\alpha]_D^{20}=+18.8°\pm1°$ (c=0.825; DMSO).

The starting material is obtained analogously to Example 23 as follows:

1 g (1.946 mmol) of 2-phenyl-4,5-[3-O-(1-ethoxycarbonyl-2-p-chlorophenylvin-1-yl-5,6-O-isopropylidene-D-glucofurano]-$\Delta^2$-oxazoline is hydrolysed with sodium hydroxide solution in ethanol. The dry Na$^+$ salt is coupled in analogous manner with 1.53 g of the trifluoroacetate of L-alanyl-D-isoglutaminyl-L-alanine-4-{2-[2-(2,6-dichlorophenylamino)-phenyl]-acetylamino} butylamide and 300 µl of triethylamine. After analogous working-up and chromatography over 300 g of silica gel using the elution mixture methylene chloride/ethanol (95:5), the E and Z isomers of the starting compound of Example 23 are obtained in the form of a mixture from the fractions having $R_f=0.35$ (CHCl$_3$:MeOH=9:1).

The two isomers can be separated by being chromatographed again over a low-pressure column of silica gel (0.04–0.63 mm) with methylene chloride/methanol/water (98:2:0.05).

Isomer A having a melting point of 259°–261°, $[\alpha]_D^{20}=+16.2°\pm2.9°$ (c=0.34; DMSO) and $R_f=0.39$ (CHCl$_3$:MeOH=9:1) and isomer B having a melting point of 140°–145°, $[\alpha]_D^{20}=+7.4°\pm1.1°$ (c=0.91, DMSO) and $R_f=0.36$ (CHCl$_3$:MeOH=9:1) are obtained.

2-phenyl-4,5-[3-O-(1-ethoxycarbonyl-2-p-chlorophenylvin-1-yl)-5,6-O-isopropylidene-D-glucofurano]-$\Delta^2$-oxazoline is obtained analogously to Example 23, by the Wittig-Horner reaction of the corresponding phosphonic ester with p-chlorobenzaldehyde, in the form of an E,Z-mixture having a melting point of 54°–56° and $[\alpha]_D^{20}=-1°\pm1°$ (c=1.028; CHCl$_3$), which can be partially separated by being chromatographed again over silica gel (0.04–0.63 mm) with methylene chloride.

The E form, which is pure according to an NMR spectrum ($[\alpha]_D^{20}=+63.5°\pm4.1°$ (c=0.241; CHCl$_3$) and $R_f=0.51$ (CH$_2$Cl$_2$:ethyl acetate=98:2)) and the Z form, which, according to an NMR spectrum, still contains approximately 10% of the E form ($[\alpha]_D^{20}=-32.9°+0.9°$ (c=1.125; CHCl$_3$)) are obtained. For the pure Z form ($R_f=0.43$ (CH$_2$Cl$_2$:ethyl acetate=98:2) there is accordingly calculated $[\alpha]_D^{20}=-44.8°$ (CHCl$_3$).

EXAMPLE 29

In a manner analogous to that described in Example 17, from 1.1 g (1.29 mmol; 1.175 mmol/g) of N-propionyldesmethylmuramyl-L-alanyl-D-isoglutamine-N-hydroxysuccinimide ester, 0.357 g (0.99 mmol) of L-alanine-3-{2-[1-(4-chlorobenzoyl)-5-methoxy-2-methylindol-3-yl]-acetylamino}-2-hydroxypropylamide hydrochloride, containing 0.17 mol of water, and 137.6 µl (0.99 mmol) of triethylamine in 30 ml of dimethylacetamide, there is obtained N-propionyldesmethylmuramyl-L-alanyl-D-isoglutaminyl-L-alanine-3-{2-[1-(4-chlorobenzoyl)-5-methoxy-2-methylindol-3-yl]-acetylamino}-2-hydroxypropylamide (anomeric and diastereoisomeric mixture) in the form of a colourless powder (lyophilisate) containing 2.96 mol of water and 0.4 mol of tert.-butanol. The compound can be crystallised from methanol/chloroform/diethyl ether (5:3:15); melting point 182°–184°, $[\alpha]_D^{20}=-8.6°\pm2.3°$ (c=0.429; water), $R_f=0.31$ (chloroform:methanol=7:3), $R_f=0.70$ (chloroform:methanol:water= 70:30:5).

The starting material is obtained as follows:

Stage 29.1

In a manner analogous to that described in Stage 24.2, from 0.893 g (2.9 mmol) of N-tert.-butoxycarbonyl-L-alanine-3-amino-2-hydroxypropylamide hydrochloride, containing 0.56 mol of water, 403 µl (2.9 mmol) of triethylamine and 1.32 g (2.9 mmol) of 1(4-chlorobenzoyl)-5-methoxy-2-methyl-3-indolylacetic acid N-hydroxysuccinimide ester in a total of 100 ml of tetrahydrofuran/water (4:1), there is obtained N-tert.-butoxycarbonyl-L-alanine-3-{2-[1-(4-chlorobenzoyl)-5-methoxy-2-methylindol-3-yl]-acetylamino}-2-hydroxypropylamide in the form of slightly yellow-coloured crystals having a melting point of 106°–108° (decomposition, from methylene chloride/diethyl ether/petroleum ether [3:4:30]) and containing 0.21 ml of water; $[\alpha]_D^{20}=-7.5°\pm1.7°$ (c=0.574; methylene chloride), $R_f=0.38$ (chloroform:ethanol=9:1), $R_f=0.52$ (chloroform:methanol=9:1), $R_f=0.69$ (chloroform:methanol=4:1).

Stage 29.2

In a manner analogous to that described in Stage 25.3, from 1.44 g (2.38 mmol) of N-tert.-butoxycarbonyl-L-alanine-3-{2-[1-(4-chlorobenzoyl)-5-methoxy-2-methylindol-3-yl]-acetylamino}-2-hydroxypropylamide, containing 0.21 mol of water, in 40 ml of ethyl acetate, with 40 ml of approximately 5N hydrochloric acid in ethyl acetate (2.5 hours, 0°), there is obtained L-alanine-3-{2-[1-(4-chlorobenzoyl)-5-methoxy-2-methylindol-3-yl]-acetylamino}-2-hydroxypropylamide hydrochloride in the form of yellowish crystals that decompose at 153° and above (made into a suspension from hot ethyl acetate) and contain 0.17 mol of water; $[\alpha]_D^{20}=+5.8°\pm1.0°$ (c=1.043; methanol), $R_f=0.22$ (chloroform:methanol =7:3).

EXAMPLE 30

1 g (2.03 mmol) of L-alanine-3-{2-[2-(3-trifluoromethylphenyl-N-methylamino)-phenyl]-acetylamino}-2-hydroxypropylamide hydrochloride and 2.185 g (3.7 mmol) of N-propionyldesmethylmuramyl-L-alanyl-D-isoglutamine-N-hydroxysuccinimide ester are dissolved in a mixture of 25 ml of N,N-dimethylformamide and 25 ml of dimethoxyethane, 0.3 ml of triethylamine is added thereto and the mixture is stirred for 17 hours at room temperature. It is then evaporated to dryness at 1.3 Pa (0.01 torr) and 40° C. and the residue is chromatographed over 140 g of silica gel (Merck; 0.04–0.63 mm) using chloroform/methanol/water (90:10:0.5) as eluant. After concentration by evaporation of the fractions having $R_f=0.24$ (CHCl$_3$:MeOH:H$_2$O=80:20:1) there is obtained an amorphous residue that is triturated with ethyl acetate. Colourless crystalline α,β-N-propionyl desmethylmuramyl-L-alanyl-D-isoglutaminyl-L-alanine-3-{2-[2-(3-trifluoromethylphenyl-N-methylamino)-phenyl]acetylamino}-2-hydroxypropylamide is thus obtained; melting point 135°–138°, $[\alpha]_D^{20} = -11°\pm 2°$ (c=0.515; H$_2$O).

The starting material is obtained as follows:

980 mg of 2-[2-(3-trifluoromethylphenyl-N-methylaminophenyl]-acetic acid are dissolved in a mixture of 10 ml of chloroform and 2 ml of N,N-dimethylformamide and then 540 mg of N-hydroxybenzotriazole and 1.5 g of N,N'-dicyclohexyl carbodiimide are added thereto. After one hour at room temperature, 1.1 g (3.3 mmol) of N-benzyloxycarbonyl-L-alanine-3-amino-2-hydroxypropylamide hydrochloride (see Stage 15.2) and 0.43 ml of triethylamine in 5 ml of chloroform are added thereto at 0°. The mixture is allowed to react for 2 hours at room temperature, evaporated to dryness at 1.3 Pa (0.1 torr) and taken up in 100 ml of methanol and 5 ml of water; the pH is adjusted to 5 with acetic acid, the dicyclohexylurea that has formed is filtered off, the filtrate is concentrated by evaporation in vacuo and the residue is taken up in ethyl acetate. This solution is extracted with saturated NaHCO$_3$ solution and water, dried with Na$_2$SO$_4$ and concentrated by evaporation. The residue is purified by chromatography over silica gel (Type Cr 60, Merck) using the elution mixture chloroform/methanol (95:5). Colourless crystalline N-benzyloxycarbonyl-L-alanine-3-{2-[2-(3-trifluoromethylphenyl-N-methylamino)-phenyl]-acetylamino}-2-hydroxypropylamide is obtained; melting point 129°–130°, $R_f$=0.60 (chloroform:methanol=9:1).

This compound is hydrogenated with 5% palladium-on-carbon in methanol with the addition of 1N methanolic hydrochloric acid to form the hydrochloride of L-alanine-3-{2-[2-(3-trifluoromethylphenyl-N-methylamino)-phenyl]-acetylamino}-2-hydroxypropylamide; $R_f$=0.19 (chloroform:methanol=8:2).

EXAMPLE 31

The following compounds are obtained by the processes described in this Application:
2-benzoylamino-2-desoxy-6-O-{N-<[2-(2,6-dichlorophenylamino) -phenyl]-acetyl>-L-valyl}-D-glucos-3-O-ylvin-1-yl-carbonyl-L-α-aminobutyryl-D-glutamic acid dimethyl ester,
N-acetylmuramyl-L-alanyl-D-(γ-methoxycarbonyl)-isoglutaminyl-L-alanine-3-{2-[2-(2,6-dichlorophenylamino)phenyl]-acetylamino}-2-hydroxypropylamide,
N-propionyldesmethylmuramyl-L-alanyl-D-glutaminyl-L-alanine-2-hydroxy-3-[d-2-(6-methoxy-2-naphthyl)-propionylamino]-propylamide,
1,4,6-tri-O-acetyl-N-propionyldesmethylmuramyl-L-alanyl-D-glutaminyl-L-alanine-2-acetoxy-3-[d-2-(6-methoxy-2-naphthyl)-propionylamino]-propylamide or
N-(N-acetylmuramyl)-O-{2-[2-(2,6-dichlorophenylamino)phenyl]-acetyl}-L-serine-D-isoglutamine.

EXAMPLE 32

Manufacture of 1000 capsules containing 0.1 mg of active ingredient per capsule:

| Composition: | |
| --- | --- |
| N—propionyldesmethylmuramyl-L-alanine-D-isoglutaminyl-L-alanine-3-{2-[2-(2,6-dichlorophenylamino)-phenyl]-acetylamino}-2-hydroxy-propylamide | 0.1 g |
| talc | 72 g |
| wheat starch | 48 g |
| magnesium stearate | 32 g |
| lactose | 8 g |
| | 160.1 g |

Preparation

The substances are forced through a sieve having a mesh width of 0.6 mm and thoroughly mixed. Gelatine capsules are made with 160.1 mg of this mixture (per capsule) using a capsule-filling machine.

We claim:

1. A sugar derivative of the formula I

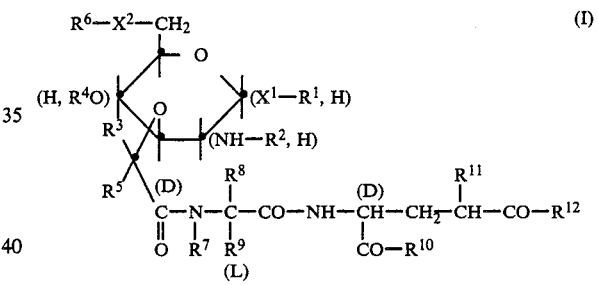

in which the sugar moiety is derived from D-glucose, D-mannose or D-galactose; $X^1$ represents oxygen, sulphur or the group NH; $X^2$ represents oxygen or the group NH; $R^1$, $R^4$ and $R^6$ each represents, independently of the others, (a) hydrogen, (b) lower alkanoyl, (c) a radical of the formula Ia,

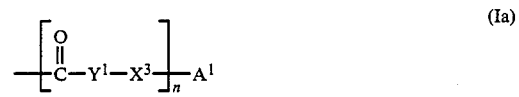

in which n represents 0 or 1; $Y^1$ represents alkylene having up to an including 18 carbon atoms which may be interrupted by carbonylimino or carbonyloxy and which is unsubstituted or substituted by at least one substituent selected from carboxy, benzyloxycarbonyl, lower alkoxycarbonyl, amino, lower alkanoylamino, hydroxy and lower alkanoyloxy; $X^3$ represents oxygen or the group NH; and $A^1$ represents the acyl radical of a carboxylic acid selected from the group consisting of 6-chloro-5-cyclohexylindan-1-carboxylic acid, 2-[4,5-bis-(4-methoxyphenyl)-oxazol-2-yl]-propionic acid, 2-(5-chloro-4-cyclohexyl-2-hydroxyphenyl)-acetic acid, 2-[4,5-bis-(4-methoxyphenyl)-oxazol-2-yl]-2-methyl-propionic acid, 2-(3-fluoro-4-pheylphenyl)-propionic acid, (±)-5-benzoyl-3H-1,2-dihydro-pyrrolo [a]pyrrole-1-carboxylic acid, 2-[4-(1,3-dihydro-1-oxo-2H-isoindol-2-yl)-phenyl]-propionic acid, 2-{2-[(2,6-dichlorophenyl)-amino]-phenyl}-acetic acid, 2-{2-[(2,6-dichloro-4-fluorophenyl)-amino]-5-fluorophenyl}-acetic acid, 2-(2,3-dimethylphenyl)-aminobenzxoic acid, 2-[4,5-bis-(4-methoxyphenyl)-imidazxol-2-yl]-2-methylpropionic acid, 2-{2-[(2,6-dichlorophenyl)-amino]-5-fluorophenyl}-acetic acid, 2-(3-benzxoylphenyl)propionic acid, 2-S-[4,5-bis-(4-methoxyphenyl)-thiazol-2-yl]mercaptoacetic acid, 3-S-[4,5-bis-(4-methoxyphenyl)-thiazol-2-yl]-mercaptopropionic acid, 2-{2-[(2,6-dichloro-4-fluorophey1)-amino]-phenyl}-acetic acid, 5-(2,4-difluorophenyl)-2-hydroxybenzoic acid, 2-(6-chloro-9H-carbaszol-2-yl)-propionic acid, 2-(4-isobutylphenyl)-propionic acid, 1-(4-chlorobenzoyl)-5-methoxy-2-methylindol-3-ylacetic acid, 2-(6-methoxynaphth-2-yl)-propionic acid, 2-[3-chloro-4-(3-pyrrolin-1-yl)-phenyl]-propionic acid, 2-(5H-[1]benzopyrano[2,3-b]-pyridin-7-yl)-propionic acid, 5-(4-methylbenzoyl)-1-methylpyrrol-2-ylacetic acid, 2-[4,5-bis-(4-methoxyphenyl)-oxazol-2-yl]-acetic acid, 1-benzoyl-5-methoxy-2-methylindol-3-ylacetic acid, 2-[3-(hydroxybenzxyl)-phenyl]-propionic acid and 2-[3-chloro-4-(pyrrol-1-yl)-phenyl]-propionic acid, or (d) radical of the formula Ib

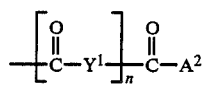
(Ib)

in which n and $Y^1$ have the meanings mentioned above and $A^2$ represents lower alkoxy selected from the group consisting of 2-[4,5-bis-(4-methoxyphenyl)-thiazol-2-ylthiol]-ethoxy, 2-[4,5-bis-(4-methoxyphenyl)-imidazol-2-yl]-2-methylpropoxy and 3-[4,5-bis-(4-methoxyphenyl)-thiazol-2-ylthio]-propoxy; or $R^1$ alternatively represents benzyl which is unsubstituted or substituted in the phenyl moiety by lower alkyl, hydroxy, lower alkoxy or halogen; $R^2$ represents unsubstituted or hydroxy-substituted lower alkanoyl, benzoyl which is unsubstituted or substituted by at least one substituent selected from lower alkyl, lower alakoxy, halogen, lower alkanoyloxy and lower alkanoylamino, or $R^2$ represents one of the above-mentioned radicals of the formulae Ia and Ib; $R^3$ represents hydrogen or lower alllkyl and $R^5$ represents hydrogen, or $R^3$ and $R^5$ together represent lower alkylidene, unsubstituted benzylidene or benzxylidene the phenyl radical of which is halogenated or substituted by lower alkyl; $R^7$ represents hydrogen or lower alkyl, or $R^7$ and $R^9$ together represents trimethylene; $R^8$ represents hydrogen or lower alkyl; $R^9$ represents hydrogen or lower alkyl that is unsubstituted or substituted by hydroxy, mercapto, lower alkylthio, carboxy, lower alkoxycarbonyl, carbamoyl, or by a radical of the formula Ic, Id, Ie or If

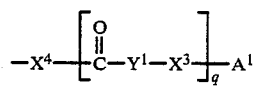
(Ic)

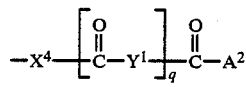
(Id)

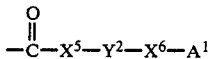
(Ie)

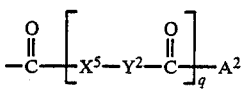
(If)

in which q represents 0 or 1; $X^4$ represents oxygen or sulphur; and $X^5$ and $X^6$ each represents, independently of the other, oxygen or the group NH; $Y^2$ represents alkylene having up to and including 18 carbon atoms in which a methylene group may have been replaced by oxygen, sulphur or sulphinyl or which may be interrupted by carbonylimino or carbonyloxy, said alkylene radical $Y^2$ being unsubstituted or substituted by at least one substituent selected from carboxy, benzyloxycarbonyl, lower alkoxycarbonyl, amino, lower alkanoylamino, hydroxy and lower alkanoyloxy, and the other substituents have the meanings mentioned above; $R^{10}$ and $R^{12}$ each represents, independently of the other, (a) lower alkoxy, (b) hydroxy, (c) amino, (d) lower alkylamino that is substituted by carboxy, by carbamoyl or by lower alkoxycarbonyl and that may be additionally substituted by at least one substituent selected from amino, hydroxy, carboxy, 2-aminomethylthio, 2-aminoethoxy and the sulpho group —$SO_3H$, (e) a radical of the formula Ig,

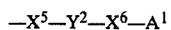
(Ig)

in which the substituents have the meanings mentioned above, or (f) a radical of the formula Ih,

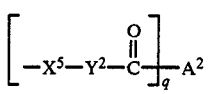
(Ih)

in which q, $X^5$, $Y^2$ and $A^2$ have the meanings mentioned above; and $R^{11}$ represents hydrogen, carboxy, lower alkoxycarbonyl or carbamoyl, said compound of the formula I having a minimum of one and a maximum of three radicals selected from $A^1$ and $A^2$, or a pharmaceutically acceptable salt of such a compound having at least one salt-forming group.

2. A compound according to claim 1, in which $R^1$, $R^4$ and $R^6$ each represents, independently of the others, (a) hydrogen, (b) lower alkanoyl, (c) a radical of the formula Ia,

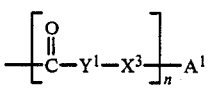
(Ia)

in which n represents 0 or 1; $Y^1$ represents alkylene having up to and including 12 carbon atoms which may be interrupted by carbonylimino or carbonyloxy and which is unsubstituted or substituted by at least one substituent selected from carboxy, benzyloxycarbonyl, lower alkoxycarbonylamino, lower alkanoylamino, hydroxy and lower alkanoyloxy; $X^3$ represents oxygen or the group NH; and $A^1$ represents the acyl radical of a carboxylic acid selected from the group consisting of 6-chloro-5-cyclohexylindan-1-carboxylic acid, 2-[4,5-bis-(4-methoxyphenyl)-oxazol-2-yl]-propionic acid, 2-

(5-chloro-4-cyclohexyl-2-hydroxyphenyl)-aceticacid, 2-[4,5-bis-(4-methoxypheny 1)-oxazol-2-yl]-2-methylpropionic acid, 2-(3-fluoro-4-phenylphenyl)-propionic acid, (±)-5-benzoyl-3H-1,2-dihydro-pyrrolo[a]pyrrole-1-carboxylic acid, 2-[4-(1,3-dihydro-1-oxo-2H-isoindol-2-yl)-phenyl]-propionic acid, 2-{2-[(2,6-dichlorophenyl)-amino]-phenyl}-acetic acid, 2-{2-[(2,6-dichloro-4-fluorophenyl)-amino]-5-fluorophenyl}-acetic acid, 2-(2,3-dimethylphenyl)-aminobenzxoic acid, 2-[4,5-bis-(4-methoxyphenyl)-imidazol-2-yl]-2-methylpropionic acid, 2-{2-[(2,6-dichlorophenyl)-amino]-5-fluorophenyl}-acetic acid, 2-(3-benzoylphenyl)-propionic acid, 2-S-[4,5-bis-(4-methoxyphenyl)-thiazol-2-yl]-marcaptoacetic acid, 3-S-[4,5-bis-(4-methoxyphenyl)-thiazol-2-yl]-mercaptopropionic acid, 2-{2-[(2,6-dichloro-4-fluorophenyl)-amino]-phenyl}-acetic acid, 5-(2,4-difluorophenyl)-2-hydroxybenzoic acid, 2-(6-chloro-9H-carbazol-2-yl)-propionic acid, 2-(4-isobutylphenyl)-propionic acid, 1-(4-chlorobenzoyl)-5-methoxy-2-methylindol-3-ylacetic acid, 2-( 6-methoxynaphth-2-yl)-propionic acid, 2-[3-chloro-4-(3-pyrrolin-1-yl)-phenyl]-propionic acid, 2-(5H-[1]benzopyrano[2,3-b]-pyridin-7-yl)-propionic acid, 5-(4-methuylbenzoyl)-1-methyl-pyrrol-2-ylacetic acid and 2-[4,5-bis-(4-methoxyphenyl)-oxazol-2-yl]-acetic acid; or (d) a radical of the formula Ib

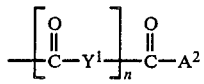

in which n and $Y^1$ have the meanings mentioned above; and $A^2$ represents lower alkoxy selected from the group consisting of 2-[4,5-bis-(4-methoxyphenyl)-thiazol-2-ylthio]-ethoxy, 2-[4,5-bis-(4-methoxyphenyl)-imidazol-2-yl]-2-methylpropoxy and 3-[4,5-bis-(4-methoxyphenyl)-thiazol-2-ylthio]-propoxy; $R^2$ represents unsubstituted or hydroxy-substituted lower alkanoyl or one of the above-mentioned radicals of the formulae Ia and Ib; $R^3$ represents hydrogen or lower alkyl; and $R^5$ represents hydrogen; or $R^3$ and $R^5$ together represent lower alkylidene; $R^{10}$ and $R^{12}$ each represents, independently of the other, (a) lower alkoxy, (b) hydroxy, (c) amino, (d) lower alkylamino that is substituted by carboxy, by carbamoyl or by lower alkoxycarbonyl and that may be additionally substituted by at least one substituent selected from amino, hydroxy, carboxy, 2-aminoethylthio, 2-aminoethoxy a the sulpho group —SO$_3$H, (e) a radical of the formula Ig,

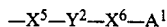

in which $Y^2$ represents alkylene having up to and including 12 carbon atoms in which a methylene group may have been replaced by oxygen or sulphur or which may be interrupted by carbonylimino or carbonyloxy, said alkylene radical $Y^2$ being unsubstituted or substituted by at least one substituent selected from carboxy, benzyloxycarbonyl, lower alkoxycarbonyl, amino, lower alkanoylamino, hydroxy and lower alkanoyloxy, and in which $X^5$, $X^6$, and $A^1$ have the meanings mentioned above; or (f) a radical of the formula Ih,

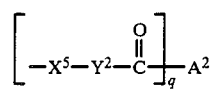

in which q, $X^5$, $Y^2$ and $A^2$ have the meanings mentioned above; and $R^{11}$ represents hydrogen, carboxy or carbamoyl; and the other substituents have the meanings mentioned in claim 1, or a pharmaceutically acceptable salt of such a compound having at least one salt-forming group.

3. Compounds of the formula I according to claim 1, in which the sugar moiety is derived from D-glucose, and pharmaceutically acceptable salts of such compounds having at least one saltforming group.

4. Compounds of the formula I according to claim 3, in which $A^1$ represents the acyl radical of a carboxylic acid selected from the group consisting of 6-chloro-5-cyclohexylindan-1-carboxylic acid (clindanac), 2-[4,5-bis-(4-methoxyphenyl)-oxazol-2-yl]-propionic acid, 2-(5-chloro-4-cyclohexyl-2-hydroxyphenyl)-acetic acid, 2-[4,5-bis-(4-methoxyphenyl)-oxazol-2-yl]-2-methylpropionic acid, 2-(3-fluoro-4-phenylphenyl)-propionic acid (flurbiprofen), (±)-5-benzoyl-3H-1,2-dihydropyrrolo[a]pyrrole-1-carboxylic acid, 2-[4-(1,3-dihydro-1-oxo-2H-isoindol-2-yl)-phenyl]-propionic acid (indoprofen), 2-{2-[(2,6-dichlorophenyl)-amino]-phenyl}-acetic acid (diclofenac), 2-{2-[(2,6-dichloro-4-fluorophenyl)-amino]-5-fluorophenyl}-acetic acid, 2-(2,3-dimethylphenyl)-aminobenzoic acid, 2-[4,5-bis-(4-methoxphenyl)-imidazol- 2-yl]-2-methylpropionic acid, 2-{2-[(2,6-dichlorophenyl)-amino]-5-fluorophenyl}-acetic acid, 2-(3-benzoylphenyl)-propionic acid (ketoprofen), 2-S-[4,5-bis-(4-methoxyphenyl)-thiazol-2-yl]-mercaptoacetic acid, 3-S-[4,5-bis-(4-methoxyphenyl)-thiazol-2-yl]-mercaptopropionic acid, 2-{2-[(2,6-dichloro-4-fluorophenyl)-amino]-phenyl}-acetic acid, 5-(2,4-difluorophenyl)-2-hydroxybenzoic acid (diflunisal), 2-(6-chloro-9H-carbazol-2-yl)-propionic acid (carprofen), 2-(4-isobutylphenyl)-propionic acid (ibuprofen), 1-(4- chlorobenzoyl)-5-methoxy-2-methylindol-3-ylacetic acid (indomethacin), 2-(6-methoxynaphth-2-yl)-propionic acid (naproxen), 2-[3-chloro-4-(3-pyrrolin-1-yl)-phenyl]propionic acid (pirprofen), 2-(5H-[1]benzopyrano[2,3-b]- pyridin-7-yl)-propionic acid (pranoprofen), 5-(4-methyl-benzoyl)-1-methylpyrrol-2-ylacetic acid (tolmetin) and 2-[4,5-bis-(4-methoxyphenyl)-oxazol-2-yl]-acetic acid, and pharmaceutically acceptable salts of such compounds having at least one salt-forming group.

5. A compound of the formula I according to claim 4, in which $X^1$ and $X^2$ represent oxygen; $R^2$ represents unsubstituted or hydroxy-substituted $C_{2-4}$-alkanoyl or a radical of the formula Ia

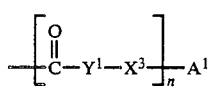

in which n represents 0 or 1; $Y^1$ represents alkylene which may be interrupted by carbonylimino or carbonyloxy and which is unsubstituted or substituted by at least one substituent selected from carboxy, benzyloxycarbonyl, lower alkoxycarbonyl, amino, lower alkanoylamino, hydroxy and lower alkanoyloxy; $X^3$ represents oxygen or the group NH; and $A^1$ represents the acyl radical of a carboxylic acid selected from the group consisting of 6-chloro-5-cyclohexylindan-1-carboxylic acid, 2-[4,5-bis-(4-methoxyphenyl)-oxazol-2-yl]-propionic acid, 2-(5-chloro-4-cyclohexyl-2-hydroxyphenyl)-acetic acid, 2-[4,5-bis-(4-methoxyphenyl)-oxazol-2-yl]-2-methyl-propionic acid, 2-(3-fluoro-4-phenylphenyl)-propionic acid, (±)-5-benzoyl-3H-1,2-dihydropyrrolo [a]pyrrole-1-carboxylic acid, 2-[4-(1,3-dihydro-1-oxo-2H-isoindol-2-yl)- phenyl]-propionic acid, 2-{2-[(2,6-dichlorophenyl)amino]-phenyl}-acetic acid, 2-{2-[2,6-dichloro-4-fluorophenyl)-amino]-5-fluorophenyl}-acetic acid, 2-(2,3-dimethylphenyl)-aminobenzoic acid, 2-[4,5-bis-(4-methoxyphenyl)-imidazol-2-yl]-2-methylpropionic acid, 2-{2-[(2,6-dichlorophenyl)-amino] -5-fluoro-phenyl}-acetic acid, 2-(3-benzoylphenyl)propionic acid, 2-S-[4,5-bis-(4-methoxyphenyl)thiazol-2-yl]-mercaptoacetic acid, 3-S-[4,5-bis-(4-methoxyphenyl)-thiazol-2-yl-mercaptopropionic acid, 2}-2-{(2,6-dichloro-4-fluorophenyl)-amino]-phenyl}-acetic acid, 5-(2,4-difluorophenyl)-2-hydroxybenzoic acid, 2-(6-chloro-9H-carbazol-2-yl)-propionic acid, 2-(4-isobutylphenyl)-propionic acid, 1-(4-chlorobenzoyl)-5-methoxy-2-methylindol-3-ylacetic acid, 2-(6-methoxynaphth-2-yl)-propionic acid, 2-[3-chloro-4-(3-pyrrolin-1-yl)-phenyl]-propionic acid, 2-(5H-[1]benzopyrano[2,3-b]-pyridin-7-yl)-propionic acid, 5-(4-methylbenzoyl)-1-methylpyrrol-2-ylacetic acid and 2-4,5-bis-(4-methoxyphenyl)-oxazxol-2-yl-acetic acid, or $R^2$ represents a radical of the formula Ib

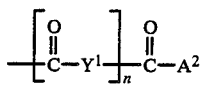  (Ib)

in which n and $Y^1$ have the meanings mentioned above; and $A^2$ represents lower alkoxy selected from the group consisting of 2-[4,5-bis-(4-methoxyphenyl)-thiazol-2-ylthio]-ethoxy, 2-[4,5-bis-(4-methoxyphenyl)-imidazol-2-yl]-2-methylpropoxy and 3-[4,5-bis-(4-methoxyphenyl)-thiazol-2-ylthio]-propoxy; $R^3$ represents hydrogen or lower alkyl; $R^5$, $R^7$ and $R^8$ represents hydrogen; $R^9$ represents lower alkyl that is unsubstituted or substituted by hydroxy, mercapto, methylthio or by a radical of the formula Ic, Id, Ie of If

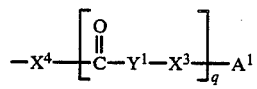  (Ic)

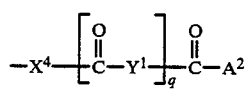  (Id)

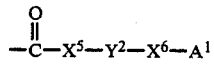  (Ie)

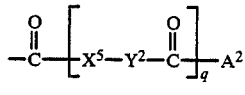  (If)

in which q represents 0 or 1; $X^4$ represents oxygen or sulphur; and $X^5$ and $X^6$ each represents, independently of the other, oxygen or the group NH; $Y^2$ represents alkylene in which a methylene group may have been replaced by oxygen, sulphur or sulphinyl and which may be interrupted by carbonylimino or carbonyloxy, said alkylene radical $Y^2$ being unsubstituted or substituted by at least one substituent selected from carboxy, benzyloxycarbonyl, lower alkoxycarbonyl, amino, lower alkanoylamino, hydroxy and lower alkanoyloxy, and the other substituents have the meanings mentioned above; $R^{10}$ represents hydroxy or amino; $R^{11}$ represents hydrogen; $R^{12}$ represents lower alkoxy, hydroxy, amino or a radical of the formula Ig or Ih as defined above, it being necessary for said compound of the formula I to have radical $A^1$ or $A^2$, or a pharmaceutically acceptable salt of such a compound having at least one salt-forming group.

6. A compound of the formula I according to claim 4, in which $X^1$ is oxygen or sulfur and $X^2$ represents oxygen, $R^2$ represents unsubstituted or hydroxy-substituted $C_{2-4}$-alkanoyl or a radical of the formula Ia or Ib as defined in accordance with claim 4, $R^3$ represents hydrogen or lower alkyl, $R^5$, $R^7$ and $R^8$ represent hydrogen, $R^9$ represents lower alkyl that is unsubstituted or substituted by hydroxy, mercapto, methylthio or by a radical of the formula Ic, Id, Ie or If as defined in accordance with claim 4, $R^{10}$ represents hydroxy or amino, $R^{11}$ represents hydrogen, $R^{12}$ represents lower alkoxy, hydroxy, amino or a radical of the formula Ig or Ih as defined in accordance with claim 4, it being necessary for the compounds of the formula I to have a radical $A^1$ or $A^2$, and pharamceutically acceptable salts of such compounds having at least one salt-forming group.

7. Compounds of the formula I according to claim 6 that have a radical of the formula Ia, Ib, Ic, Id, Ie, If, Ig or Ih in which $Y^1$ or $Y^2$ represents unsubstituted or hydroxy- or carboxy-substituted alkylene that has up to 12 carbon atoms and may be interrupted by carbonylimino or carbonyloxy, and pharmaceutically acceptable salts of such compounds having a salt-forming group.

8. Compounds of the formula I according to claim 7 that have a radical of the formula Ia, Ic, Ie or Ig in which $A^1$ represents the acyl radical of ketoprofen, naproxen or ibuprofen, and pharmaceutically acceptable salts of such compounds having a salt-forming group.

9. Compounds of the formula I according to claim 7 that have a radical of the formula Ia, Ic, Ie or Ig in which $A^1$ represents the acyl radical of diclofenac, and pharmaceutically acceptable salts of such compounds having a salt-forming group.

10. A compound according to claim 1, in which $X^1$ is oxygen or sulfur, $R^3$ represents hydrogen, lower alkyl or, together with $R^5$, optionally $C_{1-3}$-alkyl-substituted methylene, unsubstituted benzylidene or benzylidene that is halogenated or substituted by lower alkyl in the phenyl radical, or a pharmaceutically acceptable salt of such a compound having at least one salt-forming group.

11. Compounds according to claim 1, in which $R^2$ represents benzoyl and $R^3$ together with $R^5$ represents unsubstituted or $C_{1-3}$-alkyl-substituted methylene or unsubstituted or in the phenyl moiety halo-substituted benzylidene, and pharmaceutically acceptable salts of such compounds having at least one salt-forming group.

12. Compounds according to claim 4, in which $R^2$ represents benzoyl and $R^3$ together with $R^5$ represents unsubstituted or $C_{1-3}$-alkyl-substituted methylene or unsubstituted or in the phenyl moiety halo-substituted benzylidene, and pharmaceutically acceptable salts of such compounds having at least one salt-forming group.

13. Compounds of the formula I according to claim 1, in which the sugar moiety is derived from D-glucose, $X^1$ and $X^2$ represent oxygen, $R^1$ represents hydrogen or lower alkanoyl, $R^2$ represents lower alkanoyl or benzoyl, $R^3$ represents hydrogen or lower alkyl or together with $R^5$, unsubstituted or $C_{1-3}$-alkyl substituted methylene or unsubstituted or in the phenyl moiety halo-substituted benzylidene, $R^4$ presents hydrogen or lower alkanoyl, $R^5$ represents hydrogen or, together with $R^3$, unsubstituted or $C_{1-3}$-alkyl-substituted methylene or unsubstituted or in the phenyl moiety halo-substituted benzylidene, $R^6$ is hydrogen, lower alkanoyl or a radical of formula Ia in which n represents 1; $Y^1$ represents unsubstituted or carboxy-substituted lower alkylidene, $X^3$ represents NH and $A^1$ represents 2-[2-[(2,6-dichlorophenyl)-amino]-phenyl]-acetyl, $R^7$ and $R^8$ represent hydrogen;

$R^9$ represents lower alkyl, $R^{10}$ represents amino, lower alkoxy or a radical of formula Ig, in which $X^5$ represents NH, $Y^2$ represents a lower alkylene radical which may be interrupted by carbonylimino an substituted by hydroxy; $X^6$ represents NH and $A^1$ represents 2-(6-methoxynaphth-2-yl)-propionyl, $R^{11}$ represents hydrogen or lower alkoxycarbonyl, and $R^{12}$ represents lower alkoxy, hydroxy, amino, a radical of the formula Ig in which $X^5$ represents NH, $Y^2$ represents $C_{2-10}$-alkylene that is unsubstituted or substituted by at least one substituent selected from hydroxy, lower alkanoyloxy, amino, carboxy and benzyloxycarbonyl, and in which a methylene group may have been replaced by oxygen, sulphur, or sulphinyl

or which may be interrupted by carbonylimino

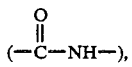

$X^6$ represents NH or oxygen and $A^1$ represents 2-{2-[(2,6-dichlorophenyl)-amino[phenyl}-acetyl, 1-benzoyl-5-methoxy-2-methylindol-3-ylacetyl, 2-(6-methoxynaphth-2-yl)-propionyl, 2-(4-isobutylphenyl)-propionyl, 2-[3-(hydroxybenzyl)phenyl]-propionyl, 2-(3benzoylphenyl)-propionyl, 2-[3-chloro-4-(pyrrol-1-yl)-phenyl]-propionyl, 1-(4-chlorobenzoyl)-5-methoxy-2-methylindol-3-ylacletyl, 2-[3-chloro-4-(3-pyrrolin-1-yl)-phenyl]propionyl or 2-[4,5-bis-(4-methoxyphenyl)-oxazol-2-yl]-propionyl, or $R^{10}$ represents a radical of the formula Ih in which q represents 1, $X^5$ represents NH, $Y^2$ represents lower alkylene and $A^2$ represents 2-[4,5-bis-(4-methoxyphenyl)-thiazol-2-ylthio]ethoxy, with the proviso that the compounds contain one and only one radical $A^1$ or $A^2$, and pharmaceutically acceptable salts of such compounds having at least one salt-forming group.

14. Compounds of the formula I according to claim 13, in which $Y^1$ represents 2-carboxyethylidene or 2-methylpropylidene and $Y^2$, in accordance with the definitions given in claim 13, represents di- or tetra-methylene, ethylidene, 1-carboxydimethylene, 1-carboxytetramethylene, 1-carboxypentamethylene, 2-hydroxytrimethylene, 1-carboxy-3-oxapentamethylene

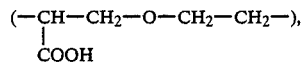

1-benzyloxycarbonyl-3-thiapentamethylene, 4-(ethyldienecarbonylimino)-n-butyl [—CH(CH$_3$)—CONH—(CH$_2$)$_4$—], 3-(ethylidenecarbonylimino) -2-hydroxypropyl, 2-acetoxy-3-ethylidenecarbonylimino)propyl, 3-[(4-aminopentylidene-carbonylimino]-2-hydroxypropyl or 1-benzyloxycarbonyl-2-(ethylene-1-sulphinyl)-dimethylene

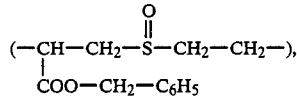

and pharmaceutically acceptable salts of such compounds having at least one salt-forming group.

15. A compound of the formula I according to claim 13 wherein $R^{10}$ represents amino or lower alkoxy and the other substituents have the meanings given in claim 13, or a pharamceutically acceptable salt of such a compound having at least one salt-forming group.

16. A compound according to claim 1, in which $X^1$ is NH, $R^3$ represents hydrogen, lower alkyl, or, together with $R^5$, optionally $C_{1-3}$-alkyl-substituted methylene, unsubstituted benzylidene or benzylidene that is halogenated or substituted by lower alkyl in the phenyl radical, or a pharamceutically acceptable salt of such a compound having at least one salt-forming group.

17. A compound of the formula 1 according to claim 1 selected from N-acetyl-6-0-{N-<[2-(2,6-dichlorophenylamino)phenyl]-acetyl >-asparagin-β-yl}-desmethylmuramyl-L-alanyl-D-isoglutamine, N-acetylmuramyl-L-alanyl-D-isoglutaminyl-L-alanine-2-{2-[2-(2,6-dichlorophenylamino)-phenyl]-acetoxy}ethylamide, Nα-(N-acetylmuramyl-L-alanyl-D-isoglutaminyl) -Nβ-{-2-[2-(2,6-dichlorophenylamino)-phenyl]-acetyl}-L-α,β-diaminopropionic acid, N-(N-acetylmuramyl-L-alanyl-D-isoglutaminyl-0-[ 2-(6-methoxy-naphth-2-yl)-propionyl]-DL-serine, (1α,β). 4,6-tri-O-acetyl-N-propionyldesmethylmuramyl-L-alanyl-D-isoglutaminyl-L-alanine-3-[d-2-(6-methoxy -2-naphthyl]-propionylamino]-2 acetoxypropyl-amide, N-propionyldesmethylmuramyl-L-alanyl-D-isoglutaminyl-L-alanine-3-[2-(3-hydroxybenzylphenyl)propionylaminol]-2-hydroxypropylamide, and N-propionyldesmethylmuramyl-L-alanyl-D-isoglutaminyl-L-alanine-3-{2-[1-(4-chlorobenzoyl)-5-methoxy-2-methylindol-3-yl]-acetylamino}-2-hydroxypropylamide, or a pharmaceutically acceptable salt of such a compound having a salt-forming group.

18. N-acetylmuramyl-L-alanyl-D-isoglutaminyl-L-alanine-3-{2-[1-benzoyl-5-methoxy-2-methylindol-3-yl]acetylamino}-2-hydroxypropylamide according to claim 1.

19. N-proprionyldesmethylmuramyl-L-alanyl-D-isoglutaminyl-L-alanine-2-[4,5-di-(4-methoxyphenyl)-thiazol-2-ylthio]-ethyl ester according to claim 1.

20. N-(N-acetylmuramyl-L-alanyl-D-isoglutaminyl-S-{2-(2,6-dichlorophenylamino)-phenylacetylamino}-ethyl-L-cysteine-benzyl ester according to claim 1.

21. N-propionyldesmethyl-muramyl-L-alanyl-D-isoglutaminyl-L-alanine-3-[2-(3-chloro-4-[pyrrol-1-yl]phenyl)propionylamino]-2-hydroxypropylamide according to claim 1.

22.

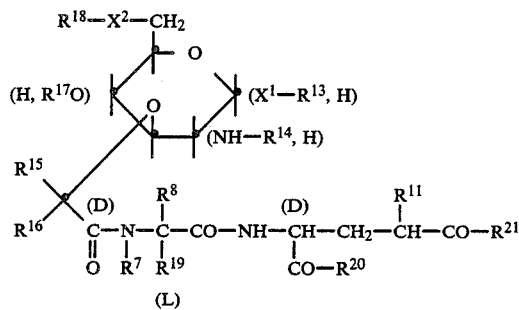

(II)

(L)

in which the sugar moiety is derived from D-glucose, D-mannose or D-galactose, $X^1$ represents oxygen, sulphur or the group NH;

$X^2$ represents oxygen or the group NH; $R^7$ represents hydrogen or lower alkyl; $R^8$ represents hydrogen or lower alkyl; $R^{11}$ represents hydrogen, carboxy, lower alkoxycarbonyl or carbamoyl;

$R^{13}$, $R^{17}$ and $R^{18}$ each represents, independently of the others, hydrdogen or lower alkanoyl, or $R^{13}$ alternatively represents benzyl which is unsubstituted or substituted in the phenyl moiety by lower alkyl, hydroxy, lower alkoxy or by halogen, $R^{14}$ represents unsubstituted or hydroxy-substituted lower alkanoyl or benzoyl which is unsubstituted or substituted by at least one substituent selected from lower alkyl, lower alkoxy, halogen, lower alkanoyloxy and lower alkanoylamino, $R^{15}$ and $R^{16}$ together represent lower alkylidene, unsubstituted benzylidene or benzylidene the phenyl radical of which is halogenated or substituted by lower alkyl, $R^{19}$ represents hydrogen or lower alkyl that is unsubstituted or substituted by hydroxy, mercapto, lower alkylthio, carboxy, lower alkoxycarbonyl or by carbamoyl, $R^{20}$ and $R^{21}$ each represents, independently of the other, lower alkoxy, hydroxy, amino, or lower alkylamino that is substituted by carboxy, carbamoyl or by lower alkoxycarbonyl and that may be additionally substituted by at least one substituent selected from amino, hydroxy, carboxy, 2-aminoethylthio, 2-aminoethoxy and the sulpho group —SO$_3$H, or a salt of such a compound having at least one salt-forming group.

23. A compound according to claim 22, in which $R^{13}$, $R^{17}$ and $R^{18}$ each represents independently of the others, hydrogen or lower alkanoyl, $R^{14}$ represents unsubstituted or hydroxy-substituted lower alkanoyl, and $R^{15}$ and $R^{16}$ together represent unsubstituted or $C_{1-3}$ alkyl substituted methylene, or a salt of such a compound having at least one salt-forming group.

24. Pharmaceutical preparations for stimulating the immune system of warm-blooded animals including humans, which preparations contain a pharmaceutically effective amount of a compound of the formula I according to claim 1 or a pharmaceutically acceptable salt of such a compound having at least one salt-forming group together with a significant amount of a pharmaceutical carrier.

25. Method for stimulating the immune resistance of warm-blooded animals including humans, characterised in that an immune resistance stimulating effective amount of a compound of the formula I according to claim 1 or a pharmaceutically acceptable salt of such a compound having at least one salt-forming group is administered.

* * * * *